US010988523B2

(12) United States Patent
Brasseur et al.

(10) Patent No.: US 10,988,523 B2
(45) Date of Patent: Apr. 27, 2021

(54) MODIFIED LIPIDATED RELAXIN B CHAIN PEPTIDES AND THEIR THERAPEUTIC USE

(71) Applicant: Sanofi, Paris (FR)

(72) Inventors: Denis Brasseur, Paris (FR); Olivier Duclos, Paris (FR); Stéphane Illiano, Paris (FR); Sergio Mallart, Paris (FR); Claire Minoletti-Hochepied, Paris (FR); Frank Marguet, Paris (FR); Elisabetta Bianchi, Pomezia (IT); Raffaele Ingenito, Pomezia (IT); Paola Magotti, Vanløse (DK); Alessia Santoprete, Pomezia (IT)

(73) Assignee: SANOFI, Paris (FR)

(*) Notice: Subject to any disclaimer, the term of this patent is extended or adjusted under 35 U.S.C. 154(b) by 0 days.

(21) Appl. No.: 16/264,547

(22) Filed: Jan. 31, 2019

(65) Prior Publication Data
US 2019/0233493 A1    Aug. 1, 2019

(30) Foreign Application Priority Data
Jan. 31, 2018 (EP) ................................. 18305093

(51) Int. Cl.
| A61K 38/00 | (2006.01) |
| A61K 47/54 | (2017.01) |
| A61P 13/12 | (2006.01) |
| A61P 1/16 | (2006.01) |
| A61P 9/10 | (2006.01) |
| A61P 9/12 | (2006.01) |
| A61P 9/14 | (2006.01) |
| C07K 14/64 | (2006.01) |
| A61K 9/00 | (2006.01) |

(52) U.S. Cl.
CPC ............ *C07K 14/64* (2013.01); *A61K 9/0019* (2013.01); *A61K 47/543* (2017.08); *A61P 1/16* (2018.01); *A61P 9/10* (2018.01); *A61P 9/12* (2018.01); *A61P 9/14* (2018.01); *A61P 13/12* (2018.01); *A61K 38/00* (2013.01)

(58) Field of Classification Search
CPC ...... A61K 38/00; A61K 47/543; A61K 47/54; A61K 9/0019; A61P 13/12; A61P 1/16; A61P 9/10; A61P 9/12; A61P 9/14; C07K 14/64
USPC ............................................. 514/1.1; 530/300
See application file for complete search history.

(56) References Cited

U.S. PATENT DOCUMENTS

| 10,081,662 B2* | 9/2018 | Bathgate .................. A61P 9/00 |
| 2017/0037106 A1* | 2/2017 | Bathgate ................. C07K 14/64 |
| 2019/0233494 A1* | 8/2019 | Duclos ....................... A61P 9/14 |
| 2019/0233495 A1* | 8/2019 | Illiano ...................... C07K 14/64 |

FOREIGN PATENT DOCUMENTS

| WO | WO2013177529 A1 | 11/2013 |
| WO | WO2015157829 A1 | 10/2015 |
| WO | WO2019149781 A1 | 8/2019 |

OTHER PUBLICATIONS

Different fibrosis diseases from Merck Manual, pp. 1-3. Accessed Apr. 28, 2020. (Year: 2020).*
Idiopathic Pulmonary Fibrosis from Merck Manual, pp. 1-3. Accessed Apr. 28, 2020. (Year: 2020).*
Pulmonary Hypertension from Merck Manual, pp. 1-11. Accessed Apr. 28, 2020. (Year: 2020).*
Acute Kidney Injury from Merck Manual, pp. 1-14. Accessed Apr. 28, 2020. (Year: 2020).*
Del Borgo, M.P. et al. (Sep. 2005). "Conformationally Constrained Single-Chain Peptide Mimics of Relaxin B-Chain Secondary Structure," J. Pept. Sci. 11(9):564-571.
Eigenbrot, C. et al. (Sep. 5, 1991). "X-Ray Structure of Human Relaxin at 1.5 A. Comparison to Insulin and Implications for Receptor Binding Determinants," J. Mol. Biol. 221(1):15-21.
Hossain, M.A. et al. (Jun. 1, 2016, e-pub. Feb. 26, 2016). "A Single-Chain Derivative of the Relaxin Hormone is a Functionally Selective Agonist of the G Protein-Coupled Receptor, RXFP1," Chem. Sci. 7(6):3805-3819.
Hossain, M.A. et al. (Oct. 2014, e-pub. Oct. 1, 2014). "Synthetic Relaxins," Curr. Opin. Chem. Biol. 22:47-55.
Hossain, M.A. et al. (Oct. 28, 2011). "The Minimal Active Structure of Human Relaxin-2", J. Biol. Chem. 286(43):37555-37565.
International Search Report dated Mar. 28, 2019, for PCT Patent Application No. PCT/EP2019/052297, filed Jan. 30, 2019, 5 pages.
Written Opinion of the International Searching Authority dated Mar. 28, 2019, for PCT Patent Application No. PCT/EP2019/052297, filed Jan. 30, 2019, 8 pages.
Bruell, S. et al. (Nov. 11, 2013). "Chimeric RXFP1 and RXFP2 Receptors Highlight the Similar Mechanism of Activation Utilizing Their N-Terminal Low-Density Lipoprotein Class A Modules," Frontiers in Endocrinology 4:171, 8 pages.
Chen, S.A. et al. (Jun. 1993). "The Pharmacokinetics of Recombinant Human Relaxin in Nonpregnant Women After Intravenous, Intravaginal, and Intracervical Administration," Pharmaceutical Research 10(6):834-838.

(Continued)

*Primary Examiner* — Julie Ha
(74) *Attorney, Agent, or Firm* — Goodwin Procter LLP

(57) ABSTRACT

Provided is a biologically active single chain Relaxin peptide having the following formula (I):

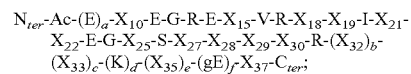

or a salt or solvate thereof. Also provided is a pharmaceutical composition comprising at least one peptide of the invention, and the peptide or the pharmaceutical composition for its use as a medicament.

20 Claims, 4 Drawing Sheets

Specification includes a Sequence Listing.

(56) References Cited

OTHER PUBLICATIONS

Ferraiolo, B.L. et al. (Aug. 2001). "The Pharmacokinetics and Metabolism of Human Relaxins in Rhesus Monkeys," Pharmaceutical Research 8(8):1032-1038.
Huang, Z. et al. (2015). "Activation of Relaxin Family Receptor 1 From Different Mammalian Species by Relaxin Peptide and Small Molecule Agonist ML290," Front. in Endo. 6: 12 pages.
Remington's Pharmaceutical Science (1975). 15th ed., Mack Publishing Company, Easton:PA, 65(6):933, (Abstract only), 1 page.
Suhadolnik, R. et al. (1968). "Nucleoside Antibiotics," The Journal of Biological Chemistry 243(12):3532-3537.

\* cited by examiner

MODIFIED LIPIDATED RELAXIN B CHAIN PEPTIDES AND THEIR THERAPEUTIC USE

CROSS REFERENCE TO RELATED APPLICATIONS

This application claims the priority benefit of E.P. Application No. EP18305093.9, filed Jan. 31, 2018, which is hereby incorporated by reference in its entirety.

Submission of Sequence Listing on Ascii Text File

The content of the following submission on ASCII text file is incorporated herein by reference in its entirety: a computer readable form (CRF) of the Sequence Listing (file name: 183952031400subseqlist.txt, date recorded: Apr. 1, 2019, size: 289 KB).

FIELD OF THE INVENTION

The present invention relates to peptide analogues of the B-chain of Relaxin-2 able to activate the RXFP1 receptor.

In particular, provided herein are lipidated peptide analogues of the B-chain of Relaxin-2 able to activate the RXFP1 receptor.

Moreover, the present invention provides pharmaceutical compositions comprising at least said peptides, and a peptide or pharmaceutical composition thereof according to the invention for its use as a medicament, and in particular for its use in the treatment and/or prevention of various diseases or conditions implicating RXFP1 receptor, more particularly a disease or condition selected from:

- the group consisting of fibrosis; fibrotic diseases, in particular systemic sclerosis, scleroderma and fibromyalgia; idiopathic pulmonary fibrosis; kidney diseases involving fibrosis;
- pulmonary hypertension and preeclampsia;
- the group consisting of heart and vascular diseases, in particular from the group consisting of acute or chronic heart failure, systolic or diastolic heart failure, coronary artery disease, atherosclerosis, microvascular angina and cardiovascular complication of diabetes; and
- the group consisting of renal failures in particular renal dysfunction in cirrhosis, chronic kidney disease and acute kidney injury.

BACKGROUND OF THE INVENTION

Human Relaxin-2 (H2 Relaxin) is a 6-kDa peptidic hormone of 53 amino acids. Its structure consists of two separate polypeptide chains, i.e. H2 Relaxin chain A (SEQ ID NO: 194) and H2 Relaxin chain B (SEQ ID NO: 195) cross-linked by two disulfide (S-S) bonds, with a third S-S intra-chain bond located in the A chain as follows:

```
H2 Relaxin A chain:
                                    (SEQ ID NO: 194)
H-Gln-Leu-Tyr-Ser-Ala-Leu-Ala-Asn-Lys-Cys*-Cys**-

His-Val-Gly-Cys*-Thr-Lys-Arg-Ser-Leu-Ala-Arg-Phe-

Cys***-OH

H2 Relaxin B chain:
                                    (SEQ ID NO: 195)
H-Asp-Ser-Trp-Met-Glu-Glu-Val-Ile-Lys-Leu-Cys**-

Gly-Arg-Glu-Leu-Val-Arg-Ala-Gln-Ile-Ala-Ile-

Cys***-Gly-Met-Ser-Thr-Trp-Ser-OH
``` wherein Cys*, Cys and Cys* indicate the disulfide bonds between Cysteines with same label.

Relaxin-2 is a naturally occurring peptide hormone produced by corpus luteum with a peak in the circulation during the first trimester of pregnancy of a woman. Relaxin-2 belongs to the insulin-like peptide family which members exert numerous effects after binding to different kinds of receptors, classified as Relaxin family peptide (RXFP) receptors (RXFP1, RXFP2, RXFP3, and RXFP4).

RXFP1 is the main receptor for Relaxin. RXFP1 contains a large extracellular domain with a single low-density lipoprotein class A (LDLa) module at the amino terminus and 10 extracellular leucine-rich repeat domains (LRRs), followed by 7 transmembrane (7TM) helical domains. The LDLa module of RXFP1 is joined to the LRR domain via a 32-residue linker.

Activation of RXFP1 is a complex multistep process. Previous studies have demonstrated that Arg13, Arg17 and Ile20, of the arginine cassette (RxxxRxxI/V, where x is any residue (SEQ ID NO: 201)) of the H2 Relaxin B-chain bind to Asp231, Asp279, Glu233 and Glu277 located on LRR4-8 of the LRR domain of RXFP1. Ligand binding alone is not sufficient to activate the receptor. Truncation or substitution of the LDLa module results in an inactive receptor despite binding to the extracellular domain. A study (Bruell, S. et al., Front. Endocrinol. (Lausanne) 4, 171 (2013)), swapping the LDLa modules of RXFP1 and RXFP2 highlighted the role of the linker in receptor activation. The LRRs (high affinity site) and the first exoloops (low affinity sites) of the transmembrane domains participate in Relaxin binding, whereas the LDLa module is required for receptor activation involving exoloop 2 (Sethi A. et al. Nature Communications (2016)).

In some species, Relaxin can also activate RXFP2, the native leucine-rich repeat containing GPCR for the insulin-like peptide 3 (INSL3). This suggests that a potential cross reactivity might be associated with Relaxin various biological activities, even though there is currently no evidence of a physiological role for Relaxin acting solely through RXFP2.

Recent published data showed that there are interspecies differences in the capacity of agonists to activate RXFP1 with a specific difference in the ECL3 domain between human and rodent (Huang et al. Frontiers in Endocrinology 2015 Aug. 17; 6:128). In parallel, biased agonist activity was described for some Relaxin-derived single chain mimetics (Hossain et al. Chem. Sci., 2016, 7, 3805). However based on IUPHAR nomenclature, RXFP1 is a Gs coupled receptor and the main signalling pathway of RXFP1 leads to cAMP (cyclic adenosine monophosphate) accumulation.

Relaxin has been identified first as a pregnancy hormone involved not only in uterus remodelling and embryo implantation but also in the hemodynamic adaptation of pregnant women. This includes decrease vascular resistance, increase in cardiac output and increase GFR, a combination of effect aiming to improve cardiac afterload. These properties have led to the use of recombinant human Relaxin 2 in several clinical trials in the context of acute heart failure.

Beneficial cardiovascular effects of Relaxin, which are attributed to alterations in the renal and systemic vasculature, have also been demonstrated in congestive and acute heart failure patients in preclinical studies and phase II clinical trials. In conscious normotensive and hypertensive male and female rats, acute intravenous and chronic subcutaneous administration of Relaxin increases cardiac output and global arterial compliance and reduces systemic vascular resistance, without affecting mean arterial pressure.

Relaxin has also been shown to reduce mean arterial pressure in rat models of hypertension. The vascular actions of Relaxin extend to modification of passive wall compliance. Chronic subcutaneous Relaxin infusion in rats and mice increases arterial compliance in small renal, mesenteric, uterine and carotid arteries. In addition Relaxin has anti-fibrotic properties in animal model of cardiac and kidney fibrosis.

Thus Relaxin could benefit to patients with chronic heart failure by decreasing after load and relieving heart activity as well as to patients with pulmonary hypertension, with heart failure with reduced or preserved ejection fraction and to patients with fibrotic diseases including systemic sclerosis, idiopathic pulmonary fibrosis and any kidney disease involving fibrosis.

Relaxin-2 is thus clearly of high therapeutic interest.

Nevertheless, H2-Relaxin complex heterodimeric structure makes its chemical synthesis and purification difficult which leads to low yields of final product (Curr. Opin. Chem. Biol. 2014, 22, 47-55).

Accordingly, there is an interest in obtaining stable Relaxin peptides that possess the ability of Relaxin to activate the RXFP1 receptors, and more particularly peptides that retain the biological activity of Relaxin, while being structurally simpler than the native Relaxin.

Peptides with simpler structures could require less complex and more efficient syntheses than H2-Relaxin thereby potentially reducing the costs of treatment linked to H2-Relaxin synthesis.

Furthermore, due to their simpler and smaller structure, such peptides may exhibit an improved uptake compared to native Relaxin, leading to an improved in vivo therapeutic activity.

Several simplified H2-Relaxin analogues have been described in the literature. M. A. Hossain et al. (J. Biol. Chem. (2011), 43, 3755) identified the minimal structure of H2-Relaxin showing that its B-chain could be truncated by up to 6 or 7 amino acids at the N-terminus with minimal loss of potency. The structures described in this publication are double chain Relaxin analogues that are still difficult to synthesize and offer no advantage compared to native H2-Relaxin.

Further attempts were made to simplify Relaxin family peptides. Recently, M. A. Hossain et al. in Chem. Sci. (2016), 7, 3805-3819 and WO2015/157829 proposed RXFP1 agonist peptides that comprise only the H2-Relaxin B chain. However, as illustrated in the present text, the peptides of WO2015/157829 present an insufficient capacity to activate the RXFP1 receptor.

There is thus a need for new peptides analogues of the B-chain of Relaxin-2 able to activate the RXFP1 receptor, in particular having an improved ability to activate the RXFP1 receptor.

There is also a need for new modified Relaxin peptides having a simple structure, in particular a simpler structure than the already known Relaxin-peptides, and that possess an improved ability to activate the RXFP1 receptor.

All references cited herein, including patent applications and publications, are incorporated by reference in their entirety.

SUMMARY OF THE INVENTION

The present invention aims to meet the here-above indicated needs.

The inventors indeed provide new modified Relaxin peptides, and in particular lipidated peptides, demonstrating a significantly improved capacity to activate the RXFP1 receptor compared to first simplified Relaxin family peptides proposed in the prior art, as demonstrated in the following examples.

As described here-after, several deletions and modifications have been brought by the inventors to the native Relaxin B-chain amino acid sequence, leading to shorter peptides having improved properties compared to the native Relaxin and to the Relaxin peptides already proposed in the prior art. In particular, the enclosed experiments demonstrate that while peptide B7-33 C11.23S (SEQ ID NO: 196) and analogous peptide from WO2015/157829, AcB7-33 C11.23S (SEQ ID NO: 197) and KKKK(AcB7-29 C11.23S) (SEQ ID NO: 198) have a 50% activation concentration (EC$_{50}$) of RXFP1 of 1641 nM, 929 nM and 206 nM respectively, in the cellular assay used to select the peptides of this invention, the EC$_{50}$ values obtained with the lipidated peptides according to the invention go from 110 nM down to 0.01 nM. Moreover, the majority of the tested peptides of the invention have an EC$_{50}$ value lower or equal to 50 nM, and in particular lower or equal to 10 nM.

Moreover, while the prior art below suggested that the B-Chain of relaxin could not be truncated by more than 7 amino-acids (J. Biol. Chem. (2011), 43, 3755; WO2015/157829) without significant reduction in potency, peptides of this invention are truncated by 9 amino-acids at the N-Terminus (Nter) and still show high activity on the RXFP1 receptor.

Compared to RXFP1 agonist peptides of WO2015/157829, peptides of the invention display improved solubility at pH 4.5 or pH 7.5, improved rat and human plasma or blood stability and in-vivo half-lives.

These properties will allow to formulate the peptides of this invention in broad concentration ranges for use as medicament that will retain their in-vivo efficacy for longer period of time, permitting for example once a day administration by the intravenous or subcutaneous route.

Accordingly, one of the objects of the present invention relates to a peptide having the following formula (I) (SEQ ID NO: 199):

$N_{ter}$-Ac-(E)$_a$-X$_{10}$-E-G-R-E-X$_{15}$-V-R-X$_{18}$-X$_{19}$-I-X$_{21}$-X$_{22}$-E-G-X$_{25}$-S-X$_{27}$-X$_{28}$-X$_{29}$-X$_{30}$-X$_{31}$-(X$_{32}$)$_b$-(X$_{33}$)$_c$-(K)$_d$-(X$_{35}$)$_e$-(gE)$_f$-X$_{37}$-C$_{ter}$ wherein:
N$_{ter}$ represents the N-terminal end of the peptide;
C$_{ter}$ represents the C-terminal end of the peptide;
a, b, c and d independently represent 0 or 1;
e and f independently represents 0, 1, 2, 3 or 4;
Ac represents acetyl group;
E represents glutamic acid (Glu);
X$_{10}$ represents an amino acid selected from the group consisting of leucine (Leu), 2-amino-isobutyric acid (Aib), Nε-acetyl-lysine (K(Ac)) and α-methyl-leucine (MeL);
G represents glycine (Gly);
R represents arginine (Arg);
X$_{15}$ represents an amino acid selected from the group consisting of lysine (Lys), homolysine (Hly), arginine (Arg), homoarginine (Har) and ornithine (Orn);
V represents valine (Val);
X$_{18}$ represents an amino acid selected from the group consisting of alanine (Ala), 2-amino-isobutyric acid (Aib), leucine (Leu), Nε-acetyl-lysine (K(Ac)) and glutamine (Gln);

$X_{19}$ represents an amino acid selected from the group consisting of glutamine (Gln), Nε-acetyl-lysine (K(Ac)), citruline (Cit), alanine (Ala) and 2-amino-isobutyric acid (Aib);

I represents isoleucine (Ile);

$X_{21}$ represents an amino acid selected from the group consisting of alanine (Ala) and 2-amino-isobutyric acid (Aib);

$X_{22}$ represents an amino acid selected from the group consisting of isoleucine (Ile) and 2-amino-isobutyric acid (Aib);

$X_{25}$ represents an amino acid selected from the group consisting of methionine (Met), norleucine (Nle), leucine (Leu), alanine (Ala), glutamine (Gln), Nε-acetyl-lysine (K(Ac)) and glutamic acid (Glu);

S represents serine (Ser);

$X_{27}$ represents an amino acid selected from the group consisting of threonine (Thr), lysine (Lys), arginine (Arg) and glutamine (Gln);

$X_{28}$ represents an amino acid selected from the group consisting of tryptophan (Trp), 5-fluoro-tryptophan (Trp(5F)), 5-chloro-tryptophan (Trp(5Cl)), 5-methoxy-tryptophan (Trp(5OMe)), tyrosine (Tyr), phenylalanine (Phe), 4-fluoro-phenylalanine (Pfp), 1-naphtylalanine (1-Nal), 2-naphtylalanine (2-Nal), α-methyl-tryptophane (Mtr), α-methyl-phenylalanine (Mph) and 5-hydroxy-tryptophane (Wox);

$X_{29}$ represents an amino acid selected from the group consisting of serine (Ser), threonine (Thr), α-methyl-serine (Mse), Nε-acetyl-lysine (K(Ac)) and valine (Val);

$X_{30}$ represents an amino acid selected from the group consisting of lysine (Lys), 2-amino-isobutyric acid (Aib), α-methyl-lysine (Mly), arginine (Arg) and α-methyl-arginine (Mar);

$X_{31}$ represents an amino acid selected from the group consisting of arginine (Arg), Nω-methyl-arginine (Rme), alanine (Ala), Nω,Nω'-dimethyl-arginine (Rds, symmetrical dimethyl arginine) and citruline (Cit);

$X_{32}$ represents an amino acid selected from the group consisting of lysine (Lys), Nε-acetyl-lysine (K(Ac)), arginine (Arg), alanine (Ala) and Nε,Nε,Nε-tri-methyl-lysine (Tml);

$X_{33}$ represents an amino acid selected from the group consisting of leucine (Leu), lysine (Lys), Nε-acetyl-lysine (K(Ac)), alanine (Ala) and arginine (Arg);

K represents lysine (Lys);

$X_{35}$ represents a polyethylene glycol derivative selected from the group consisting of $PEG_2$, $PEG_4$, $PEG_8$, $PEG_2DGA$, TTDS, $PEG_{12}$, $PEG_{24}$ and $PEG_{28}$;

gE represents gamma-glutamic acid (γGlu, glutamic acid connected by its gamma carboxylic acid);

and $X_{37}$ represents the following structure:

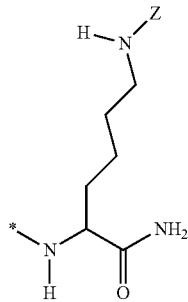

in which:

-* represents a covalent bond: with $(gE)_f$ when f is different from 0; with $(X_{35})_e$ when f is 0 and e is different from 0; with $(K)_d$ when e and f are 0 and d is 1; with $(X_{33})_c$ when d, e and f are 0 and c is 1; with $(X_{32})_b$ when c, d, e and f are 0 and b is 1; or with $X_{31}$ when b, c, d, e and f all are 0; and Z represents a group of formula (II):

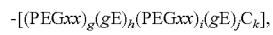

in which:

g and i independently represent 0, 1, 2, 3, 4 or 5;
h and j independently represent 0, 1, 2, 3, 4 or 5;
PEGxx independently represents a polyethylene glycol derivative selected from the group consisting of $PEG_2$, $PEG_2DGA$, TTDS and $PEG_{12}$; and
$C_k$ represents a linear saturated $C_{12}$-$C_{22}$ acyl group;
or a salt or solvate thereof.

A particular embodiment of the invention is a peptide having the formula (I) or a pharmaceutically acceptable salt or a solvate thereof wherein the peptide is able to activate the RXFP1 receptor.

Another embodiment of the present invention is a pharmaceutical composition comprising at least one peptide according to the invention, or a pharmaceutically acceptable salt or solvate thereof, together with at least one pharmaceutically acceptable carrier.

A further embodiment of the present invention relates to a peptide of the invention, a pharmaceutically acceptable salt or solvate thereof, or a pharmaceutical composition thereof according to the invention, for its use as a medicament.

Accordingly, the present invention further relates to a peptide of the invention, a pharmaceutically acceptable salt or solvate thereof or a pharmaceutical composition thereof according to the invention, for its use in the treatment and/or prevention of various diseases or conditions implicating the RXFP1 receptor, more particularly in the treatment and/or prevention of diseases or conditions selected from:

the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia;

the group consisting of heart and vascular diseases, in particular from the group consisting of acute or chronic heart failure, systolic or diastolic heart failure, coronary artery disease, atherosclerosis, microvascular angina and cardiovascular complication of diabetes; and/or the group consisting of renal failures in particular renal dysfunction in cirrhosis, chronic kidney disease and acute kidney injury.

In one embodiment, said disease or condition can be selected from the group consisting of heart and vascular diseases, in particular from the group consisting of acute or chronic heart failure, systolic or diastolic heart failure, coronary artery disease, atherosclerosis, microvascular angina and cardiovascular complication of diabetes.

DETAILED DESCRIPTION OF THE INVENTION

Definitions

Figure 1:
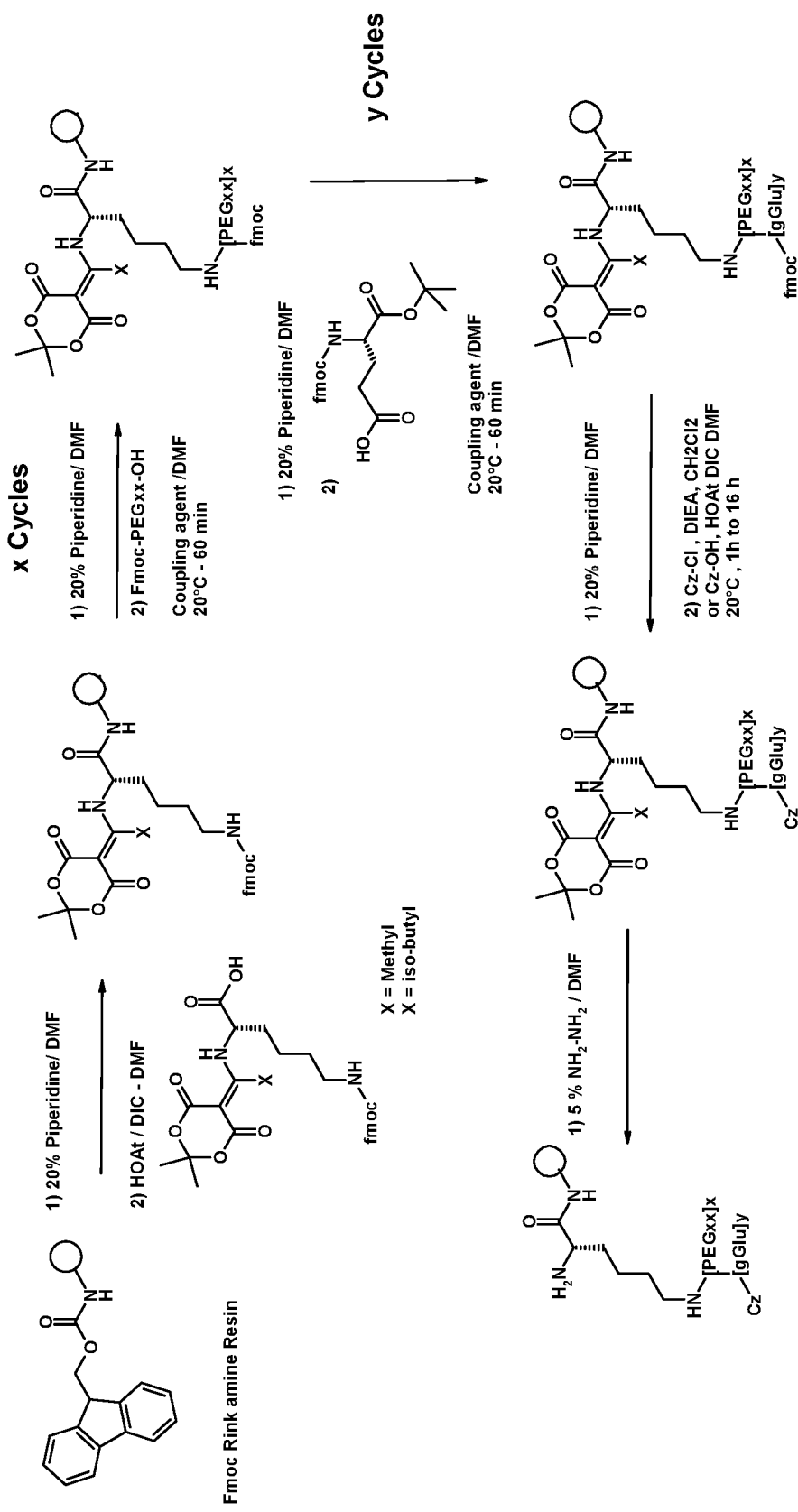
FIGS. 1 and 2 are the two parts of a schema representing a first general method used for synthesizing the peptides of the invention. With this method, the peptides are assembled with the above mentioned Z group already installed.

As used herein:

"$X_y$" used in the formulae of the invention with y having different values represents an amino acid as defined in the definition of said formulae. y indicates the position of said amino acid in the native B-chain of Relaxin-2. For example, $X_{10}$ represents the amino acid in position 10 of the amino acid sequence of the native B-chain of Relaxin-2.

"pharmaceutically acceptable carrier" is intended for a fluid, especially a liquid comprising a peptide of the invention, such that the pharmaceutical composition is physiologically tolerable, i.e. can be administered to the individual body without toxicity or undue discomfort.

a "biologically active" peptide according to the invention is a peptide able to activate the RXFP1 receptor.

When applicable, amino acids in the peptides of the invention can each independently be L-amino acids or D-amino acids. In a particular embodiment, amino acids according to the present invention are L-amino acids. In the present text, if no information is indicated regarding the L- or D-form of a given amino acid, then this amino acid is an L-amino acid.

$N_{ter}$ and $C_{ter}$ are conventional labels used to indicate, respectively, the N-terminal end of the peptide and the C-terminal end of the peptide of the invention.

A "peptide" or "Relaxin peptide" according to the invention is a modified lipidated Relaxin B chain peptide in accordance with the present invention. In particular, such "peptide" or "Relaxine peptide" means a peptide which is biologically active, i.e. that displays a biological activity typically associated with Relaxin and in particular which is as indicated here-above able to activate the RXFP1 receptor. The level of such Relaxin biological activity displayed by the modified peptides according to the invention may be equivalent or advantageously enhanced when compared with the activity of a naturally occurring or native Relaxin, or even when compared to already disclosed Relaxin peptides different from the one of the present invention.

The term "native" as used in the present text in connection with Relaxin refers to naturally occurring or wild type molecules.

"Preventing" is intended to mean reducing the risk of manifestation of the phenomenon under consideration. This reduction may be total or partial, i.e. results in a degree of risk that is lower than that pre-existing the use according to the invention.

"Treating" is intended to mean reducing or even eliminating the undesirable condition or disease under consideration.

"individual" or "patient" is intended to mean a human or non-human mammal affected or likely to be affected with a condition considered according to the invention. Said individual is in particular a human being.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

The present inventors have designed new modified peptides, in particular lipidated peptides.

The inventors have unexpectedly found herein that a shorter and strongly amended peptide according to the invention, i.e. amino acids sequence according to the invention, has a superior biological activity, in particular a superior capacity to activate the RXFP1 receptor in comparison to single B-chain Relaxin known in the art.

Peptides of the Invention

Peptides according to the invention are characterized in that they are of formula (I) (SEQ ID NO. 199):

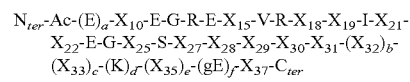

wherein:

$N_{ter}$ represents the N-terminal end of the peptide;
$C_{ter}$ represents the C-terminal end of the peptide;
a, b, c and d independently represent 0 or 1;
e and f independently represents 0, 1, 2, 3 or 4;
Ac represents acetyl group;
E represents glutamic acid;
$X_{10}$ represents an amino acid selected from the group consisting of leucine, 2-amino-isobutyric acid, Nε-acetyl-lysine and α-methyl-leucine;
G represents glycine;
R represents arginine;
$X_{15}$ represents an amino acid selected from the group consisting of lysine, homolysine, arginine, homoarginine and ornithine;
V represents valine;
$X_{18}$ represents an amino acid selected from the group consisting of alanine, 2-amino-isobutyric acid (Aib), leucine, Nε-acetyl-lysine (K(Ac)), and glutamine;
$X_{19}$ represents an amino acid selected from the group consisting of glutamine, Nε-acetyl-lysine (K(Ac)), citruline (Cit), alanine and 2-amino-isobutyric acid (Aib);
I represents an isoleucine;
$X_{21}$ represents an amino acid selected from the group consisting of alanine and 2-amino-isobutyric acid (Aib);
$X_{22}$ represents an amino acid selected from the group consisting of isoleucine and 2-amino-isobutyric acid (Aib);
$X_{25}$ represents an amino acid selected from the group consisting of methionine, norleucine (Nle), leucine, alanine, glutamine, Nε-acetyl-lysine (K(Ac)) and glutamic acid;
S represents serine;
$X_{27}$ represents an amino acid selected from the group consisting of threonine, lysine, arginine and glutamine;
$X_{28}$ represents an amino acid selected from the group consisting of tryptophan, 5-fluoro-tryptophan, 5-chloro-tryptophan, 5-methoxy-tryptophan, tyrosine, phenylalanine, 4-fluoro-phenylalanine (Pfp), 1-naphtylalanine (1-Nal), 2-naphtylalanine (2-Nal), α-methyl-tryptophane (Mtr), α-methyl-phenylalanine (Mph) and 5-hydroxy-tryptophane (Wox);
$X_{29}$ represents an amino acid selected from the group consisting of serine, threonine, α-methyl-serine (Mse), Nε-acetyl-lysine (K(Ac)) and valine;
$X_{30}$ represents an amino acid selected from the group consisting of lysine, 2-amino-isobutyric acid (Aib), α-methyl-lysine (Mly), arginine and α-methyl-arginine;

$X_{31}$ represents an amino acid selected from the group consisting of arginine, Nω-methyl-arginine (Rme), alanine, Nω,Nω'-dimethyl-arginine (Rds, symmetrical dimethyl arginine) and citruline (Cit);

$X_{32}$ represents an amino acid selected from the group consisting of lysine, Nε-acetyl-lysine (K(Ac)), arginine, alanine and Nε,Nε,Nε-tri-methyl-lysine (Tml);

$X_{33}$ represents an amino acid selected from the group consisting of leucine, lysine, Nε-acetyl-lysine (K(Ac)), alanine and arginine;

K represents lysine;

$X_{35}$ represents a polyethylene glycol derivative selected from the group consisting of $PEG_2$, $PEG_4$, $PEG_8$, $PEG_2DGA$, TTDS, $PEG_{12}$, $PEG_{24}$ and $PEG_{28}$;

gE represents gamma-glutamic acid (γGlu); and $X_{37}$ represents the following structure:

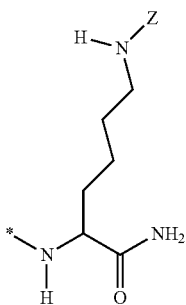

in which:
- * represents a covalent bond: with $(gE)_f$ when f is different from 0; with $(X_{35})_e$ when f is 0 and e is different from 0; with $(K)_d$ when e and f are 0 and d is 1; with $(X_{33})_e$ when d, e and f are 0 and c is 1; with $(X_{32})_b$ when c, d, e and f are 0 and b is 1; or with $X_{31}$ when b, c, d, e and f all are 0; and Z represents a group of formula (II):

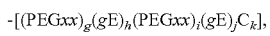

-[$(PEGxx)_g(gE)_h(PEGxx)_i(gE)_jC_k$], in which:
g and i independently represent 0, 1, 2, 3, 4 or 5;
h and j independently represent 0, 1, 2, 3, 4 or 5;
PEGxx independently represents a polyethylene glycol derivative selected from the group consisting of $PEG_2$, $PEG_2DGA$, TTDS and, $PEG_{12}$; and
$C_k$ represents a linear saturated $C_{12}$-$C_{22}$ acyl group;
or a salt or solvate thereof.

The present invention also includes salts of the peptides of the formulae (I) or (Ia) defined herein, in one embodiment pharmaceutically acceptable salts, for example salts as acid adduct with inorganic acids such as hydrochloric acid, sulphuric acid, nitric acid, hydrobromic acid, phosphoric acid, perchloric acid, thiocyanic acid and boric acid; or with organic acid such as formic acid, acetic acid, trifluoroacetic acid, propionic acid, glycolic acid, citric acid, tartaric acid, succinic acid, gluconic acid, lactic acid, malonic acid, fumaric acid, anthranilic acid, benzoic acid, cinnamic acid, benzenesulfonic acid, p-toluenesulfonic acid, naphthalenesulfonic acid and sulfanilic acid; and salts with metals such as alkali metal, e.g. sodium, potassium, lithium, zinc, and aluminium.

In one embodiment the salts of the peptides are pharmaceutically acceptable salts, for example acid adducts with hydrochloric acid, sulphuric acid, phosphoric acid, formic acid, acetic acid, propionic acid, glycolic acid, citric acid, tartaric acid, succinic acid, gluconic acid, lactic acid, malonic acid, fumaric acid, anthranilic acid, benzoic acid, cinnamic acid, benzenesulfonic acid, p-toluenesulfonic acid, naphthalenesulfonic acid and sulfanilic acid; and salts with metals such as alkali metal, e.g. sodium, potassium, lithium and zinc.

The present invention also includes solvates and in one embodiment pharmaceutically acceptable solvates, of the peptides of the above formulae (I) or (Ia).

Solvates mean complexes of the compounds of the invention or salts thereof with solvent molecules, e.g. organic solvent molecules and/or water.

According to an embodiment of the invention, the invention also includes pharmaceutically acceptable salt or solvate of the peptides of the invention.

As illustrated, a peptide according to the invention is an amino acid sequence.

In keeping with standard polypeptide nomenclature (J. Biol. Chem., 243:3552-59 (1969)) abbreviations for α-amino acid residues used in the present invention are as follows:

| One letter code | Three letter code | Amino acid |
|---|---|---|
| A | Ala | Alanine |
| C | Cys | Cysteine |
| D | Asp | Aspartic acid or aspartate |
| E | Glu | Glutamic acid or glutamate |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

For non natural or modified amino acids the following abbreviations are used:

| | |
|---|---|
| Aib | 2-amino-isobutyric acid |
| Cit | Citruline |
| Har | Homoarginine |
| Hly | Homolysine |
| Hph | Homophenylalanine |
| gE | γ-Glutamic acid (glutamic acid connected by its γ-carboxylic acid function) |
| Nle | Norleucine, 2-amino hexanoic acid |
| K(Ac) | Nε-Acetyl-lysine, 2-amino-4-acetamido-hexanoic acid |
| Mar | α-Methyl-arginine |
| Mel | α-Methyl-leucine |
| Mly | α-Methyl-lysine |
| Mph | α-Methyl-phenylalanine |
| Mse | α-Methyl-serine |
| Mtr | α-Methyl-tryptophane |
| 1-Nal | 1-Naphtylalanine |
| 2-Nal | 2-Naphtylalanine |
| Orn | Ornithine |
| Pfp | 4-Fluoro-phenylalanine |
| Rds | Nω,Nω'-dimethyl-arginine (symmetrical) |
| Rme | Nω-methyl-arginine |
| Tml | Nε,Nε,Nε-trimethyl-lysine |
| Trp(5-Cl) | 5-Chlorotryptophan |

| | |
|---|---|
| Trp(5-F) | 5-Fluorotryptophan |
| Trp(5-OMe) | 5-Methoxytryptophan |
| Wox | 5-Hydroxy-tryptophane |

In all the formulae according to the invention, where the amino acid sequence is represented by using the above mentioned abbreviations and $X_y$ representations such as $X_{18}$ for example, the left and right orientation is in the conventional direction of amino-terminus to carboxy-terminus.

Accordingly, for example, with $X_{28}$ representing an amino acid selected from the group of tryptophan, 5-fluoro-tryptophan, 5-chloro-tryptophan, 5-methoxy-tryptophan, tyrosine, phenylalanine, 4-fluoro-phenylalanine, 1-naphtylalanine, 2-naphtylalanine, α-methyl-tryptophane, α-methyl-phenylalanine and 5-hydroxy-tryptophane, the N-terminus or amine group of said amino acid is linked to the amino acid represented by $X_{27}$ and the C-terminus or carboxyl group of said amino acid is linked to the amino acid represented by $X_{29}$.

As indicated previously, gE, which can also be represented as γE, gGlu or γGlu, represents a gamma-glutamic acid. This amino acid has the following structure:

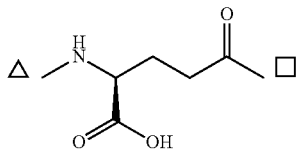

in which:

when gE is represented by $X_{36}$ in the formulae of the invention, Δ represents a covalent bond with the group in $N_{ter}$ of this $X_{36}$ group and □ represents a covalent bond with the group in $C_{ter}$ of this $X_{36}$ group, on the basis of the $N_{ter}$-$C_{ter}$ orientation represented in the formulae according to the invention; and when these groups are represented in formula (II):
  (i) for $(gE)_h$ when h is different from 0, Δ represents a covalent bond with the (PEGxx)i group if i is different from 0, or with $(gE)_j$ when i is 0 and j is different from 0, or with $C_k$ when i and j are 0, and □ represents a covalent bond with the (PEGxx)g group if g is different from 0, or a covalent bond linking the group of formula (II) with the structure $X_{37}$ when g is 0; and, independently,
  (ii) for $(gE)_j$ when j is different from 0, Δ represents a covalent bond with $C_k$, and □ represents a covalent bond with (PEGxx)i when i is different from 0, or with the (gE)h group if i is different from 0, or with $(PEGxx)_g$ if i and h are 0 and g is different from 0, or represents a covalent bond linking the group of formula (II) with the nitrogen atom of lateral chain of the lysine structure in $X_{37}$ if g, h and i are 0.

On its N-terminal ($N_{ter}$) extremity, a peptide of the invention is substituted with an acetyl group (Ac):$CH_3C(O)$—.

On its C-terminal ($C_{ter}$) extremity, a peptide of the invention is substituted with a $X_{37}$ group having the structure:

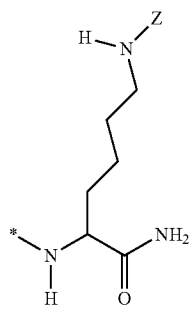

This structure corresponds to a lysine amino acid wherein:
  the alpha (α) nitrogen atom (*) is bound to the previous part of the peptide, i.e. with the group in $N_{ter}$ of $X_{37}$ on the basis of the $N_{ter}$-$C_{ter}$ orientation represented in the formulae according to the invention, through a covalent bond, in particular through a peptide bond, i.e. with $(gE)_f$ when f is different from 0; with $(X_{35})_e$ when f is 0 and e is different from 0; with $(K)_d$ when e and f are 0 and d is 1; with $(X_{33})_c$ when d, e and f are 0 and c is 1; with $(X_{32})_b$ when c, d, e and f are 0 and b is 1; or with $X_{31}$ when b, c, d, e and f are 0;
  the carboxyl group has been transformed in an amide function; and
  the nitrogen atom of its lateral chain is bound to a Z group.

This Z group is defined as being of formula (II):

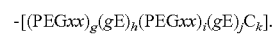

-[(PEGxx)$_g$(gE)$_h$(PEGxx)$_i$(gE)$_j$C$_k$].

In formula (II), the - represents a covalent bound with the nitrogen atom of the lateral chain of the lysine structure in $X_{37}$.

g and i independently represent 0, 1, 2, 3, 4 or 5. h and j also independently represent 0, 1, 2, 3, 4 or 5.

When g is different from 0, the nitrogen atom of the lateral chain of the lysine in $X_{37}$ is bound to $(PEGxx)_g$.

When g is 0 and h is different from 0, the nitrogen atom of the lateral chain of the lysine in $X_{37}$ is bound to $(gE)_h$.

When g and h represent 0 and i is different from 0, the nitrogen atom of the lateral chain of the lysine in $X_{37}$ is bound to $(PEGxx)_i$.

When g, h and i represent 0 and j is different from 0, the nitrogen atom of the lateral chain of the lysine in $X_{37}$ is bound to $(gE)_j$.

When g, h, i and j represent 0, the nitrogen atom of the lateral chain of the lysine in $X_{37}$ is bound to $C_k$.

$C_k$ represents a linear saturated $C_{12}$-$C_{22}$ acyl group, in particular a linear saturated acyl group selected from the group consisting of $C_{12}$ (Lau), $C_{14}$ (Myr), $C_{15}$ (Penta), $C_{16}$ (Palm), $C_{17}$ (Hepta), $C_{18}$ (Stea), $C_{20}$ (Eico) and $C_{22}$ (Doco) acyl group. In one embodiment $C_k$ represents a linear saturated acyl group selected from the group consisting of $C_{12}$ (Lau), $C_{14}$ (Myr), $C_{15}$ (Penta), $C_{16}$ (Palm), $C_{17}$ (Hepta) or $C_{18}$ (Stea) acyl group, in particular a linear saturated $C_{14}$, $C_{16}$ or $C_{18}$ acyl group, and even more particularly a linear $C_{16}$ or $C_{18}$ acyl group.

In a particular embodiment, $C_k$ represents a linear saturated $C_{12}$ acyl group. A linear saturated $C_{12}$ acyl group of the invention is a lauroyl group (also represented as "Lau" in the present text).

In a particular embodiment, $C_k$ represents a linear saturated $C_{14}$ acyl group. A linear saturated $C_{14}$ acyl group of the invention is a Myristoyl group (also represented as "Myr" in the present text).

In a particular embodiment, $C_k$ represents a linear saturated $C_{15}$ acyl group. A linear saturated $C_{15}$ acyl group of the invention is a pentadecanoyl group (also represented as "Penta" in the present text).

In a particular embodiment, $C_k$ represents a linear saturated $C_{16}$ acyl group. A linear saturated $C_{16}$ acyl group of the invention is a palmitoyl group (also represented as "Palm" in the present text).

In a particular embodiment, $C_k$ represents a linear saturated $C_{17}$ acyl group. A linear saturated $C_{17}$ acyl group of the invention is a heptadecanoyl group (also represented as "Hepta" in the present text).

In another particular embodiment, $C_k$ represents a linear saturated $C_{18}$ acyl group. A linear saturated $C_{18}$ acyl group of the invention is a stearoyl group (also represented as "Stea" in the present text).

In another particular embodiment, $C_k$ represents a linear saturated $C_{20}$ acyl group. A linear saturated $C_{20}$ acyl group of the invention is a Eicosanoyl group (also represented as "Eico" in the present text).

In another particular embodiment, $C_k$ represents a linear saturated $C_{22}$ acyl group. A linear saturated $C_{22}$ acyl group of the invention is a Docosanoyl group (also represented as "Doco" in the present text).

PEGxx in the formulae of the invention independently represents a polyethylene glycol derivative selected from the group consisting of $PEG_2$, $PEG_2DGA$, TTDS and $PEG_{12}$.

$X_{35}$ is defined in formula (I) according to the invention as representing a polyethylene glycol derivative selected from the group consisting of $PEG_2$, $PEG_4$, $PEG_8$, $PEG2DGA$, TTDS, $PEG_{12}$, $PEG_{24}$, and $PEG_{28}$.

Said groups are defined as follows:

| Abbreviation | Structure | IUPAC name |
|---|---|---|
| $PEG_2$ | 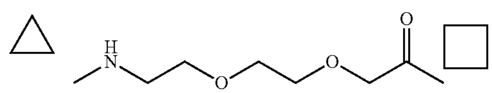 | 2-[2-(2-aminoethoxy)ethoxy]acetyl |
| $PEG_2DGA$ | 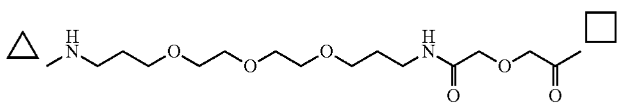 | 2-[2-[3-[2-[2-(3-aminopropoxy)ethoxy]ethoxy]propylamino-2-oxo-ethoxy]acetyl |
| TTDS | 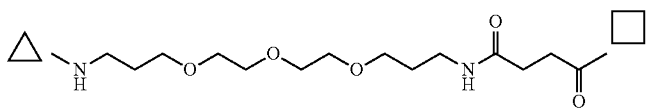 | 4-[3-[2-[2-(3-aminopropoxy)ethoxy] ethoxy] propylamino]-4-oxo-butanoyl |
| $PEG_4$ | 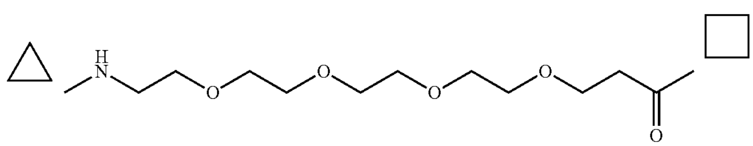 | 2-[2-[2-[2-aminoethoxy]ethoxy]ethoxy] propanoyl |
| $PEG_8$ | 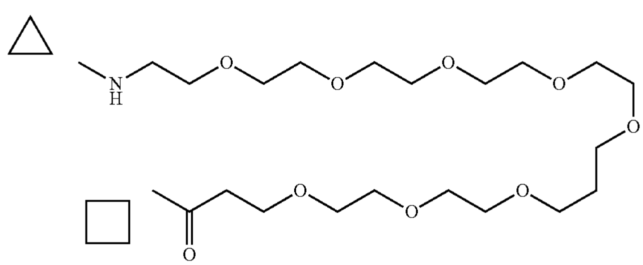 | 2-[2-[2-[2-[2-[2-[2-[2-aminoethoxy]ethoxy]ethoxy]ethox]ethoxy]ethoxy]ethoxy]ethoxy] ethoxy] propanoyl |
| $PEG_{12}$ | 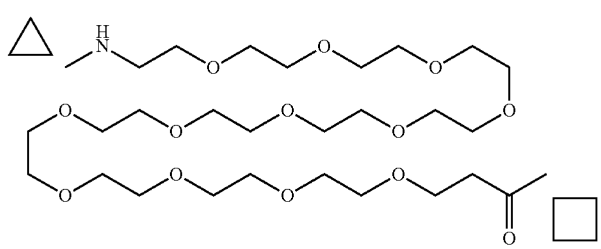 | [3-[2-[2-[2-[2-[2-[2-[2-[2-[2-(2-aminoethoxy)ethoxy]ethoxy]ethoxy]ethoxy]ethoxy]ethoxy]ethoxy]ethoxy]ethoxy]ethoxy]ethoxy] propanoyl |

| Abbreviation | Structure | IUPAC name |
|---|---|---|
| PEG$_{24}$ | 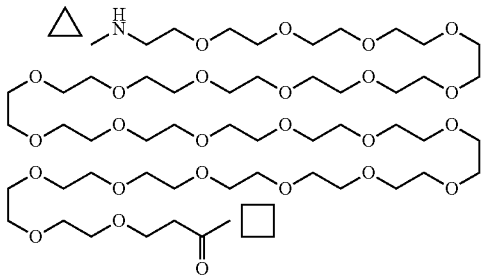 | 3-[2-[2-[2-[2-[2-[2-[2-[2-[2-[2-[2-[2-[2-[2-[2-[2-[2-[2-[2-[2-[2-(2-aminoethoxy)ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]etthoxy]ethoxy]ethoxy]ethoxy]ethoxy]ethoxy]ethoxy] propanoyle |
| PEG$_{28}$ | | 3-[2-[2-[2-[2-[2-[2-[2-[2-[2-[2-[2-[2-[2-[2-[2-[2-[2-[2-[2-[2-[2-[2-[2-[2-(2-aminoethoxy)ethoxy] ethoxy] ethoxy] ethoxy] ethoxy] ethoxy] ethoxy] ethoxy] ethoxy]ethoxy] ethoxy] ethoxy] ethoxy]ethoxy] ethoxy] ethoxy] ethoxy] ethoxy] ethoxy] ethoxy] ethoxy] ethoxy] ethoxy] ethoxy] ethoxy] ethoxy] ethoxy] propanoyle | in which:

when these groups are represented by $X_{35}$ in the formulae of the invention, Δ represents a covalent bond with the group in $N_{ter}$ of this $X_{35}$ group and □ represents a covalent bond with the group in $C_{ter}$ of this $X_{35}$ group, on the basis of the $N_{ter}$-$C_{ter}$ orientation represented in the formulae according to the invention; and when these groups are represented by PEGxx in formula (II):

(i) for (PEGxx)$_g$ when g is different from 0, Δ represents a covalent bond with the (gE)$_h$ group if h is different from 0, or with (PEGxx)$_i$ if h is 0 and i is different from 0, or with (gE)$_j$ when h and i are 0 and j is different from 0, or with $C_k$ when g, h, i and j are 0, and □ represents a covalent bond linking the group of formula (II) with the nitrogen atom of lateral chain of the lysine structure in $X_{37}$; and, independently, (ii) for (PEGxx)$_i$ when i is different from 0, Δ represents a covalent bond with (gE)$_j$ when j is different from 0, or with $C_k$ when j is 0, and □ represents a covalent bond with the (gE)h group if h is different from 0, or with (PEGxx)$_g$ if h is 0 and g is different from 0, or represents a covalent bond linking the group of formula (II) with the structure $X_{37}$ if g and h are 0.

In formula (I) of the invention, it is more particularly indicated $(X_{35})_e$ and (PEGxx)$_g$ or (PEGxx)$_i$, with e, g and i representing, independently, 0 or values different from 0 indicated here-above.

Accordingly, it is important to note that, for example, when $X_{35}$ represents PEG$_2$ and e represents 2, which can be represented (PEG$_2$)$_2$, this is completely different from PEG$_4$.

Indeed, while PEG$_4$ is structurally as defined in the Table above:

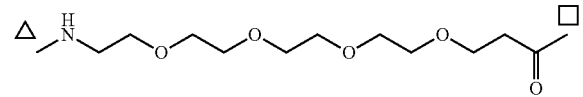

the structure of (PEG$_2$)$_2$ corresponds to a PEG$_2$ group following another PEG$_2$ group (i.e. PEG$_2$-PEG$_2$) and can be represented as follows:

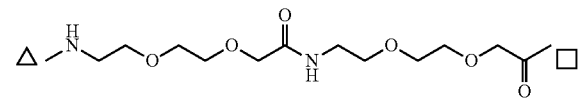

When a represents 0, the glutamic acid E in position 9 is not present. Accordingly, when a represents 0, the Acetyl group (Ac) is directly bound to $X_{10}$.

Similarly when b represents 0, $X_{31}$ is directly linked:
to $(X_{33})_c$ if c represents 1;
to $(K)_d$ if c represents 0 and d represents 1;
to $(X_{35})_e$ if c and d represent 0 and e is different from 0;
to (gE)$_f$ if c, d and e represent 0 and f is different from 0;
or
to $X_{37}$ if c, d, e and f represent 0.

When c represents 0 and b represents 1, $(X_{32})_b$ is directly linked:
to the lysine $(K)_d$ if d represents 1;
to $(X_{35})_e$ if d represents 0 and e is different from 0;
to (gE)$_f$ if d and e represent 0 and f is different from 0; or
to $X_{37}$ if d, e and f represent 0.

When d represents 0 and c represents 1, $(X_{33})_c$ is directly linked:
- to $(X_{35})_e$ if e is different from 0;
- to $(gE)_f$ if e represents 0 and f is different from 0; or
- to $X_{37}$ if e and f represent 0.

When e represents 0 and d represents 1, $(K)_d$ is directly linked:
- to $(gE)_f$ if f is different from 0; or
- to $X_{37}$ if f represents 0.

When f represents 0 and e is different from 0, $(X_{35})_e$ is directly linked to $X_{37}$.

According to a particular embodiment, a peptide according to the invention is of formula (Ia) (SEQ ID NO: 200):

$N_{ter}$-Ac-$(E)_a$-L-E-G-R-E-K-V-R-$X_{18}$-$X_{19}$-I-Aib-Aib-E-G-$X_{25}$-S-T-$X_{28}$-$X_{29}$-$X_{30}$-$X_{31}$-$(X_{32})_b$-$(X_{33})_c$-$(K)_d$-$(X_{35})_e$-$(gE)_f$-$X_{37}$-$C_{ter}$ wherein:
$N_{ter}$ represents the N-terminal end of the peptide;
$C_{ter}$ represents the C-terminal end of the peptide;
a, b, c and d independently represent 0 or 1;
e represents 0, 1, 2, 3 or 4;
f represents 0, 2 or 3;
Ac represents acetyl group;
E represents glutamic acid;
L represents leucine;
G represents glycine;
R represents arginine;
K represents lysine;
V represents valine;
$X_{18}$ represents an amino acid selected from the group consisting of alanine, 2-amino-isobutyric acid and leucine;
$X_{19}$ represents an amino acid selected from the group consisting of glutamine, Nε-acetyl-lysine and alanine;
I represents isoleucine;
Aib represents 2-amino-isobutyric acid;
$X_{25}$ represents an amino acid selected from the group consisting of methionine, norleucine, glutamine, Nε-acetyl-lysine and glutamic acid;
S represents serine;
T represents threonine;
$X_{28}$ represents an amino acid selected from the group consisting of tryptophan, 1-naphtylalanine, phenylalanine, tyrosine, α-methyl-tryptophane, α-methyl-phenylalanine and 5-hydroxy-tryptophane;
$X_{29}$ represents an amino acid selected from the group consisting of serine, threonine and α-methyl-serine;
$X_{30}$ represents an amino acid selected from the group consisting of lysine, 2-amino-isobutyric acid and α-methyl-lysine;
$X_{31}$ represents an amino acid selected from the group consisting of arginine, Nω-methyl-arginine, alanine, Nω,Nω'-dimethyl-arginine and citruline;
$X_{32}$ represents an amino acid selected from the group consisting of lysine, alanine, Nε-acetyl-lysine and Nε,Nε,Nε-tri-methyl-lysine;
$X_{33}$ represents an amino acid selected from the group consisting of leucine, lysine and Nε-acetyl-lysine (K(Ac));
$X_{35}$ represents a polyethylene glycol derivative selected from the group consisting of $PEG_2$, $PEG_4$, $PEG_8$, $PEG_2DGA$, TTDS, $PEG_{12}$, $PEG_{24}$ and $PEG_{28}$;
gE represents gamma-glutamic acid;
and
$X_{37}$ represents the following structure:

in which:
-* is as defined in above; and
Z is selected from the group consisting of a -palmitoyl (-Palm), -gamma glutamic acid-palmitoyl (-gE-Palm), -gamma glutamic acid-stearoyl (-gE-Stea), -(gamma glutamic acid)$_2$-palmitoyl (-$(gE)_2$-Palm), -(gamma glutamic acid)$_3$-palmitoyl (-$(gE)_3$-Palm), -(gamma glutamic acid)$_3$-stearoyl (-$(gE)_3$-Stea), -(gamma glutamic acid)$_4$-stearoyl (-$(gE)_4$-Stea), -(gamma glutamic acid)$_4$-plamitoyl (-$(gE)_4$-Palm), -stearoyl (-stea), -$PEG_2$-Palmitoyl (-$PEG_2$-Palm), -$(PEG_2)_2$-Stearoyl (-$(PEG_2)_2$-Stea), -$(PEG_2)_3$-Stearoyl (-$(PEG_2)_3$-Stea), -$PEG_2$-(gamma glutamic acid)-Palmitoyl (-$PEG_2$-gE-Palm), -$PEG_2$-(gamma glutamic acid)$_2$-Palmitoyl (-$PEG_2$-$(gE)_2$-Palm), -$PEG_2$-(gamma glutamic acid)$_3$-Palmitoyl (-$PEG_2$-$(gE)_3$-Palm), -$(PEG_2)_2$-(gamma glutamic acid)-Stearoyl (-$(PEG_2)_2$-gE-Stea), -$(PEG_2)_2$-(gamma glutamic acid)$_2$-Palmitoyl (-$(PEG_2)_2$-$(gE)_2$-Palm), -$(PEG_2)_2$-(gamma glutamic acid)$_3$-Palmitoyl (-$(PEG_2)_2$-$(gE)_3$-Palm), -$(PEG_2)_3$-(gamma glutamic acid)$_3$-Palmitoyl (-$(PEG_2)_3$-$(gE)_3$-Palm), -$(PEG_2)_4$-(gamma glutamic acid)$_3$-Palmitoyl (-$(PEG_2)_4$-$(gE)_3$-Palm), -$(PEG_2)_3$-(gamma glutamic acid)$_4$-Palmitoyl (-$(PEG_2)_3$-$(gE)_4$-Palm), -$PEG_{12}$-(gamma glutamic acid)$_3$-Palmitoyl (-$PEG_{12}$-$(gE)_3$-Palm), -$(PEG_2)_2$-(gamma glutamic acid)$_3$-Stearoyl (-$(PEG_2)_2$-$(gE)_3$-Stea), -$(PEG_2)_3$-(gamma glutamic acid)$_3$-Stearoyl (-$(PEG_2)_3$-$(gE)_3$-Stea), -$(PEG_2)_3$-(gamma glutamic acid)$_4$-Stearoyl (-$(PEG_2)_3$-$(gE)_4$-Stea), -$(PEG_2)_4$-(gamma glutamic acid)$_3$-Stearoyl (-$(PEG_2)_4$-$(gE)_3$-Stea), -$(PEG_2)_5$-(gamma glutamic acid)$_3$-Stearoyl (-$(PEG_2)_5$-$(gE)_3$-Stea), -($PEG_2DGA$)-(gamma glutamic acid)$_3$-Stearoyl (-($PEG_2DGA$)-$(gE)_3$-Stea), -($PEG_2DGA$)$_2$-(gamma glutamic acid)$_3$-Stearoyl (-($PEG_2DGA$)$_2$-$(gE)_3$-Stea), -($PEG_2DGA$)$_3$-(gamma glutamic acid)$_3$-Stearoyl (-($PEG_2DGA$)$_3$-$(gE)_3$-Stea), -$PEG_{12}$-(gamma glutamic acid)$_3$-Stearoyl (-($PEG_{12}$)-$(gE)_3$-Stea), -$(PEG_2)_2$-(gamma glutamic acid)$_3$-$PEG_2$-Stearoyl (-$(PEG_2)_2$-$(gE)_3$-$PEG_2$-Stea), -$(PEG_2)_2$-(gamma glutamic acid)$_2$-$PEG_2$-(gamma glutamic acid)-Stearoyl (-$(PEG_2)_2$-$(gE)_2$-$PEG_2$-(gE)-Stea), -$(PEG_2)_2$-(gamma glutamic acid)$_3$-$PEG_2$-(gamma glutamic acid)-Stearoyl (-$(PEG_2)_2$-$(gE)_3$-$PEG_2$-(gE)-Stea), -(gamma glutamic acid)$_2$-$(PEG_2)_2$-(gamma glutamic acid)-Stearoyl (-$(gE)_2$-$(PEG_2)_2$-(gE)-Stea), -(gamma glutamic acid)$_2$-$(PEG_2)_3$-(gamma glutamic acid)-Stearoyl (-$(gE)_2$-$(PEG_2)_3$-(gE)-Stea), -$(PEG_2)_3$-(gamma glutamic acid)$_5$-Stearoyl (-$(PEG_2)_3$-$(gE)_5$-Stea), -$(PEG_2)_3$-(gamma glutamic acid)$_3$-Lauroyl (-$(PEG_2)_3$-$(gE)_3$-Lau), -(gamma glutamic acid)$_5$-stearoyl (-$(gE)_5$-Stea), -$(PEG_2)_4$-(gamma glutamic acid)$_4$-Palmitoyl (-$(PEG_2)_4$-$(gE)_4$-Palm), -(gamma glutamic acid)$_4$-Lauroyl (-$(gE)_4$-Lau), -$(PEG_2)_3$-(gamma glutamic acid)$_3$-Pentadecanoyl (-$(PEG_2)_3$-$(gE)_3$-Penta), -$(PEG_2)_3$-(gamma glutamic acid)$_3$-Heptadecanoyl (-$(PEG_2)_3$-$(gE)_3$-Hepta), -$(PEG_2)_2$-(gamma glutamic acid)$_2$-PEG$_2$-(gamma glutamic acid)-Palmitoyl (-(PEG$_2$)$_2$-(gE)$_2$-PEG$_2$-(gE)-Palm), -(TTDS)$_2$-(gamma glutamic acid)$_3$-Palmitoyl (-(TTDS)$_2$-(gE)$_3$-Palm), -(gamma glutamic acid)$_4$-Pentadecanoyl (-(gE)$_4$-Penta), -(gamma glutamic acid)$_2$-Pentadecanoyl (-(gE)$_2$-Penta), -(gamma glutamic acid)$_4$-Myristoyl (-(gE)$_4$-Myr), -(PEG$_2$)$_3$-(gamma glutamic acid)$_3$-Myristoyl (-(PEG$_2$)$_3$-(gE)$_3$-Myr), -(PEG$_2$)$_4$-(gamma glutamic acid)$_4$-Stearoyl (-(PEG$_2$)$_4$-(gE)$_4$-Stea), -(TTDS)$_3$-(gamma glutamic acid)$_3$-Palmitoyl (-(TTDS)$_3$-(gE)$_3$-Palm), -(gamma glutamic acid)$_3$-Pentadecanoyl (-(gE)$_3$-Penta), -(TTDS)$_3$-(gamma glutamic acid)$_3$-Pentadecanoyl (-(TTDS)$_3$-(gE)$_3$-Penta), -(PEG$_2$)$_3$-(gamma glutamic acid)$_3$-Eicosanoyl ((-PEG$_2$)$_3$-(gE)$_3$-Eico) and -(PEG$_2$)$_3$-(gamma glutamic acid)$_3$-docosanoyl ((-PEG$_2$)$_3$-(gE)$_3$-Doco);

or a salt or solvate thereof.

In all these Z groups, the first - symbol represents the covalent bond between the Z group and nitrogen atom of the lateral chain of the lysine X$_{37}$ structure.

Accordingly, when the Z group is for example represented as being -PEG$_2$-(gamma glutamic acid)-Palmitoyl (also represented as -PEG$_2$-gE-Palm), PEG$_2$ is bound to the nitrogen atom of the lateral chain of the X$_{37}$ structure. A covalent bond also binds the PEG$_2$ group with the gamma-glutamic acid (gE). The gE group is further linked by a covalent bond to a palmitoyl (Palm) group.

Similarly, when the Z group is for example represented as being -(gamma glutamic acid)$_2$-(PEG$_2$)$_3$-(gamma glutamic acid)-Stearoyl (-(gE)$_2$-(PEG$_2$)$_3$-(gE)-Stea), a first gE group from the two gE groups (represented as (gE)$_2$) is bound to the nitrogen atom of the lateral chain of the X$_{37}$ structure. A covalent bond also binds this gE group to the second gE group represented in (gE)$_2$. This second gE group is also bound to the first PEG$_2$ group from the three PEG$_2$ groups (represented as (PEG$_2$)$_3$). The two other PEG$_2$ groups represented by the (PEG$_2$)$_3$ then follow and are linked by covalent bonds. A covalent bond then links the third PEG$_2$ group to the gE group represented as (gE). This gE group is further linked by a covalent bond to a stearoyl (Stea) group.

Furthermore, it must be understood from the present application that a Z group according to the invention represented for example as -(PEG$_2$)$_2$-(gamma glutamic acid)$_3$-PEG$_2$-Stearoyl (also represented as -(PEG$_2$)$_2$-(gE)$_3$-PEG$_2$-Stea) could also have been represented -PEG$_2$-PEG$_2$-gE-gE-gE-PEG$_2$-Stea.

The same applies mutatis mutandis for the other represented Z groups according to the invention.

According to a particular embodiment, a peptide according to the invention has an amino acid sequence selected from the group consisting of the amino acid sequences of reference SEQ ID NO: 1-193.

In a particular embodiment, (X$_{35}$), represents a polyethylene glycol derivative selected from the group consisting of PEG$_2$, (PEG$_2$)$_2$, (PEG$_2$)$_3$, (PEG$_2$)$_4$, PEG$_2$DGA, (PEG$_2$DGA)$_2$, (PEG$_2$DGA)$_3$, (TTDS)$_2$, (TTDS)$_3$, PEG$_4$, (PEG$_4$)$_2$, PEG$_8$, PEG$_{12}$, PEG$_{24}$ and PEG$_{28}$ In a particular embodiment, Z is selected from the group consisting of -gamma glutamic acid-palmitoyl (-gE-Palm), -(gamma glutamic acid)$_2$-palmitoyl (-(gE)$_2$-Palm), -(gamma glutamic acid)$_3$-palmitoyl (-(gE)$_3$-Palm), -(gamma glutamic acid)$_3$-stearoyl (-(gE)$_3$-Stea), -(gamma glutamic acid)$_4$-stearoyl (-(gE)$_4$-Stea), -(gamma glutamic acid)$_4$-palmitoyl (-(gE)$_4$-Palm), -(PEG$_2$)$_2$-(gamma glutamic acid)-Stearoyl (-(PEG$_2$)$_2$-gE-Stea), -(PEG$_2$)$_2$-(gamma glutamic acid)$_2$-Palmitoyl (-(PEG$_2$)$_2$-(gE)$_2$-Palm), -(PEG$_2$)$_2$-(gamma glutamic acid)$_2$-Palmitoyl (-(PEG$_2$)$_2$-(gE)$_2$-Palm), -(PEG$_2$)$_3$-(gamma glutamic acid)$_3$-Palmitoyl (-(PEG$_2$)$_3$-(gE)$_3$-Palm), -(PEG$_2$)$_4$-(gamma glutamic acid)$_3$-Palmitoyl (-(PEG$_2$)$_4$-(gE)$_3$-Palm), -(PEG$_2$)$_3$-(gamma glutamic acid)$_4$-Palmitoyl (-(PEG$_2$)$_3$-(gE)$_4$-Palm), -PEG$_{12}$-(gamma glutamic acid)$_3$-Palmitoyl (-PEG$_{12}$-(gE)$_3$-Palm), -(PEG$_2$)$_2$-(gamma glutamic acid)$_3$-Stearoyl (-(PEG$_2$)$_2$-(gE)$_3$-Stea), -(PEG$_2$)$_3$-(gamma glutamic acid)$_3$-Stearoyl (-(PEG$_2$)$_3$-(gE)$_3$-Stea), -(PEG$_2$)$_3$-(gamma glutamic acid)$_4$-Stearoyl (-(PEG$_2$)$_3$-(gE)$_4$-Stea), -(PEG$_2$)$_4$-(gamma glutamic acid)$_3$-Stearoyl (-(PEG$_2$)$_4$-(gE)$_3$-Stea), -(PEG$_2$)$_5$-(gamma glutamic acid)$_3$-Stearoyl (-(PEG$_2$)$_5$-(gE)$_3$-Stea), -(PEG$_2$DGA)-(gamma glutamic acid)$_3$-Stearoyl (-(PEG$_2$DGA)-(gE)$_3$-Stea), -(PEG$_2$DGA)$_2$-(gamma glutamic acid)$_3$-Stearoyl (-(PEG$_2$DGA)$_2$-(gE)$_3$-Stea), -(PEG$_2$DGA)$_3$-(gamma glutamic acid)$_3$-Stearoyl (-(PEG$_2$DGA)$_3$-(gE)$_3$-Stea), -PEG$_{12}$-(gamma glutamic acid)$_3$-Stearoyl (-(PEG$_{12}$)-(gE)$_3$-Stea), -(PEG$_2$)$_2$-(gamma glutamic acid)$_3$-PEG$_2$-Stearoyl (-(PEG$_2$)$_2$-(gE)$_3$-PEG$_2$-Stea), -(PEG$_2$)$_2$-(gamma glutamic acid)$_2$-PEG$_2$-(gamma glutamic acid)-Stearoyl (-(PEG$_2$)$_2$-(gE)$_2$-PEG$_2$-(gE)-Stea), -(PEG$_2$)$_2$-(gamma glutamic acid)$_3$-PEG$_2$-(gamma glutamic acid)-Stearoyl (-(PEG$_2$)$_2$-(gE)$_3$-PEG$_2$-(gE)-Stea), -(gamma glutamic acid)$_2$-(PEG$_2$)$_2$-(gamma glutamic acid)-Stearoyl (-(gE)$_2$-(PEG$_2$)$_2$-(gE)-Stea), -(gamma glutamic acid)$_2$-(PEG$_2$)$_3$-(gamma glutamic acid)-Stearoyl (-(gE)$_2$-(PEG$_2$)$_3$-(gE)-Stea), -(PEG$_2$)$_3$-(gamma glutamic acid)$_5$-Stearoyl (-(PEG$_2$)$_3$-(gE)$_5$-Stea), -(gamma glutamic acid)$_5$-Stearoyl (-(gE)$_5$-Stea), -(PEG$_2$)$_4$-(gamma glutamic acid)$_4$-Palmitoyl (-(PEG$_2$)$_4$-(gE)$_4$-Palm); -(gamma glutamic acid)$_4$-Lauroyl (-(gE)$_4$-Lau), -(PEG$_2$)$_3$-(gamma glutamic acid)$_3$-Pentadecanoyl (-(PEG$_2$)$_3$-(gE)$_3$-Penta), -(PEG$_2$)$_3$-(gamma glutamic acid)$_3$-Heptadecanoyl (-(PEG$_2$)$_3$-(gE)$_3$-Hepta), -(PEG$_2$)$_2$-(gamma glutamic acid)$_2$-PEG$_2$-(gamma glutamic acid)-Palmitoyl (-(PEG$_2$)$_2$-(gE)$_2$-PEG$_2$-(gE)-Palm), -(TTDS)$_2$-(gamma glutamic acid)$_3$-Palmitoyl (-(TTDS)$_2$-(gE)$_3$-Palm), -(gamma glutamic acid)$_4$-Pentadecanoyl (-(gE)$_4$-Penta), -(gamma glutamic acid)$_2$-Pentadecanoyl (-(gE)$_2$-Penta), -(gamma glutamic acid)$_4$-Myristoyl (-(gE)$_4$-Myr), -(PEG$_2$)$_4$-(gamma glutamic acid)$_4$-Stearoyl (-(PEG$_2$)$_4$-(gE)$_4$-Stea), -(TTDS)$_3$-(gamma glutamic acid)$_3$-Palmitoyl (-(TTDS)$_3$-(gE)$_3$-Palm), -(gamma glutamic acid)$_3$-Pentadecanoyl (-(gE)$_3$-Penta), -(TTDS)$_3$-(gamma glutamic acid)$_3$-Pentadecanoyl (-(TTDS)$_3$-(gE)$_3$-Penta), -(PEG$_2$)$_3$-(gamma glutamic acid)$_3$-Eicosanoyl ((-PEG$_2$)$_3$-(gE)$_3$-Eico) and -(PEG$_2$)$_3$-(gamma glutamic acid)$_3$-docosanoyl ((-PEG$_2$)$_3$-(gE)$_3$-Doco).

In a particular embodiment, a peptide according to the invention of formula (Ia) is such that N$_{ter}$ represents the N-terminal end of the peptide;

C$_{ter}$ represents the C-terminal end of the peptide;

a, b, c and d independently represent 0 or 1;

e represents 0, 1, 2, 3 or 4;

f represents 0, 2 or 3;

Ac represents acetyl group;

E represents glutamic acid;

L represents leucine;

G represents glycine;

R represents arginine;

K represents lysine;

V represents valine;

X$_{18}$ represents an amino acid selected from the group consisting of alanine, 2-amino-isobutyric acid (Aib) and leucine;

X$_{19}$ represents an amino acid selected from the group consisting of glutamine, Nε-acetyl-lysine (K(Ac)) and alanine;

I represents isoleucine;

Aib represents 2-amino-isobutyric acid;

$X_{25}$ represents an amino acid selected from the group consisting of methionine, norleucine (Nle), glutamine, Nε-acetyl-lysine (K(Ac)) and glutamic acid;
S represents serine;
T represents threonine;
$X_{28}$ represents an amino acid selected from the group consisting of tryptophan, 1-naphtylalanine (1-Nal), phenylalanine, tyrosine, α-methyl-tryptophane (Mtr), α-methyl-phenylalanine (Mph) and 5-hydroxy-tryptophane (Wox);
$X_{29}$ represents an amino acid selected from the group consisting of serine, threonine and α-methyl-serine (Mse);
$X_{30}$ represents an amino acid selected from the group consisting of lysine, 2-amino-isobutyric acid (Aib) and α-methyl-lysine (Mly);
$X_{31}$ represents an amino acid selected from the group consisting of arginine, Nω-methyl-arginine (Rme), Nω,Nω'-dimethylmethyl-arginine (Rds), alanine and citruline (Cit);
$X_{32}$ represents an amino acid selected from the group consisting of lysine, alanine and Nε,Nε,Nε-tri-methyl-lysine (Tml);
$X_{33}$ represents an amino acid selected from the group consisting of leucine, lysine and Nε-acetyl-lysine (K(Ac));
$(X_{35})_e$, represents a polyethylene glycol derivative selected from the group consisting of $PEG_2$, $(PEG_2)_2$, $(PEG_2)_3$, $(PEG_2)_4$, $PEG_2DGA$, $(PEG_2DGA)_2$, $(PEG_2DGA)_3$, $(TTDS)_2$, $(TTDS)_3$, $PEG_4$, $(PEG_4)_2$, $PEG_8$, $PEG_{12}$, $PEG_{24}$ and $PEG_{28}$;
gE represents gamma-glutamic acid;
$X_{37}$ represents the following structure:

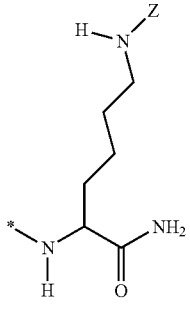

in which:
-* is as defined previously; and
Z is selected from the group consisting of -gamma glutamic acid-palmitoyl (-gE-Palm), -(gamma glutamic acid)$_2$-palmitoyl (-(gE)$_2$-Palm), -(gamma glutamic acid)$_3$-palmitoyl (-(gE)$_3$-Palm), -(gamma glutamic acid)$_3$-stearoyl (-(gE)$_3$-Stea), -(gamma glutamic acid)$_4$-stearoyl (-(gE)$_4$-Stea), -(gamma glutamic acid)$_4$-plamitoyl (-(gE)$_4$-Palm), -(PEG$_2$)$_2$-(gamma glutamic acid)-Stearoyl (-(PEG$_2$)$_2$-gE-Stea), -(PEG$_2$)$_2$-(gamma glutamic acid)$_2$-Palmitoyl (-(PEG$_2$)$_2$-(gE)$_2$-Palm), -(PEG$_2$)$_2$-(gamma glutamic acid)$_3$-Palmitoyl (-(PEG$_2$)$_2$-(gE)$_3$-Palm), -(PEG$_2$)$_3$-(gamma glutamic acid)$_3$-Palmitoyl (-(PEG$_2$)$_3$-(gE)$_3$-Palm), -(PEG$_2$)$_4$-(gamma glutamic acid)$_3$-Palmitoyl (-(PEG$_2$)$_4$-(gE)$_3$-Palm), -(PEG$_2$)$_3$-(gamma glutamic acid)$_4$-Palmitoyl (-(PEG$_2$)$_3$-(gE)$_4$-Palm), -PEG$_{12}$-(gamma glutamic acid)$_3$-Palmitoyl (-PEG$_{12}$-(gE)$_3$-Palm), -(PEG$_2$)$_2$-(gamma glutamic acid)$_3$-Stearoyl (-(PEG$_2$)$_2$-(gE)$_3$-Stea), -(PEG$_2$)$_3$-(gamma glutamic acid)$_3$-Stearoyl (-(PEG$_2$)$_3$-(gE)$_3$-Stea), -(PEG$_2$)$_3$-(gamma glutamic acid)$_4$-Stearoyl (-(PEG$_2$)$_3$-(gE)$_4$-Stea), -(PEG$_2$)$_4$-(gamma glutamic acid)$_3$-Stearoyl (-(PEG$_2$)$_4$-(gE)$_3$-Stea), -(PEG$_2$)$_5$-(gamma glutamic acid)$_3$-Stearoyl (-(PEG$_2$)$_5$-(gE)$_3$-Stea), -(PEG$_2$DGA)-(gamma glutamic acid)$_3$-Stearoyl (-(PEG$_2$DGA)-(gE)$_3$-Stea), -(PEG$_2$DGA)$_2$-(gamma glutamic acid)$_3$-Stearoyl (-(PEG$_2$DGA)$_2$-(gE)$_3$-Stea), -(PEG$_2$DGA)$_3$-(gamma glutamic acid)$_3$-Stearoyl (-(PEG$_2$DGA)$_3$-(gE)$_3$-Stea), -PEG$_{12}$-(gamma glutamic acid)$_3$-Stearoyl (-(PEG$_{12}$)-(gE)$_3$-Stea), -(PEG$_2$)$_2$-(gamma glutamic acid)$_3$-PEG$_2$-Stearoyl (-(PEG$_2$)$_2$-(gE)$_3$-PEG$_2$-Stea), -(PEG$_2$)$_2$-(gamma glutamic acid)$_2$-PEG$_2$-(gamma glutamic acid)-Stearoyl (-(PEG$_2$)$_2$-(gE)$_2$-PEG$_2$-(gE)-Stea), -(PEG$_2$)$_2$-(gamma glutamic acid)$_3$-PEG$_2$-(gamma glutamic acid)-Stearoyl (-(PEG$_2$)$_2$-(gE)$_3$-PEG$_2$-(gE)-Stea), -(gamma glutamic acid)$_2$-(PEG$_2$)$_2$-(gamma glutamic acid)-Stearoyl (-(gE)$_2$-(PEG$_2$)$_2$-(gE)-Stea), -(gamma glutamic acid)$_2$-(PEG$_2$)$_3$-(gamma glutamic acid)-Stearoyl (-(gE)$_2$-(PEG$_2$)$_3$-(gE)-Stea), -(PEG$_2$)$_3$-(gamma glutamic acid)$_5$-Stearoyl (-(PEG$_2$)$_3$-(gE)$_5$-Stea), -(gamma glutamic acid)$_5$-Stearoyl (-(gE)$_5$-Stea), -(PEG$_2$)$_4$-(gamma glutamic acid)$_4$-Palmitoyl (-(PEG$_2$)$_4$-(gE)$_4$-Palm); -(gamma glutamic acid)$_4$-Lauroyl (-(gE)$_4$-Lau), -(PEG$_2$)$_3$-(gamma glutamic acid)$_3$-Pentadecanoyl (-(PEG$_2$)$_3$-(gE)$_3$-Penta), -(PEG$_2$)$_3$-(gamma glutamic acid)$_3$-Heptadecanoyl (-(PEG$_2$)$_3$-(gE)$_3$-Hepta), -(PEG$_2$)$_2$-(gamma glutamic acid)$_2$-PEG$_2$-(gamma glutamic acid)-Palmitoyl (-(PEG$_2$)$_2$-(gE)$_2$-PEG$_2$-(gE)-Palm), -(TTDS)$_2$-(gamma glutamic acid)$_3$-Palmitoyl (-(TTDS)$_2$-(gE)$_3$-Palm), -(gamma glutamic acid)$_4$-Pentadecanoyl (-(gE)$_4$-Penta), -(gamma glutamic acid)$_2$-Pentadecanoyl (-(gE)$_2$-Penta), -(gamma glutamic acid)$_4$-Myristoyl (-(gE)$_4$-Myr), -(PEG$_2$)$_4$-(gamma glutamic acid)$_4$-Stearoyl (-(PEG$_2$)$_4$-(gE)$_4$-Stea), -(TTDS)$_3$-(gamma glutamic acid)$_3$-Palmitoyl (-(TTDS)$_3$-(gE)$_3$-Palm), -(gamma glutamic acid)$_3$-Pentadecanoyl (-(gE)$_3$-Penta), -(TTDS)$_3$-(gamma glutamic acid)$_3$-Pentadecanoyl (-(TTDS)$_3$-(gE)$_3$-Penta), -(PEG$_2$)$_3$-(gamma glutamic acid)$_3$-Eicosanoyl ((-PEG$_2$)$_3$-(gE)$_3$-Eico) and -(PEG$_2$)$_3$-(gamma glutamic acid)$_3$-docosanoyl ((-PEG$_2$)$_3$-(gE)$_3$-Doco);
or a salt or solvate thereof.

In a special embodiment, $(X_{35})$, represents a polyethylene glycol derivative selected from the group consisting of $(PEG_2)_3$, $(PEG_2)_4$, $(TTDS)_2$ and $(TTDS)_3$.

In a special embodiment, Z is selected from the group consisting of (-(PEG$_2$)$_3$-(gE)$_3$-Stea), -((PEG$_2$)$_3$-(gE)$_3$-Palm), -((gE)$_2$-Stea), -((gE)$_2$-Palm), -((gE)$_3$-Stea), -((gE)$_3$-Palm), -((gE)$_4$-Stea) and -((gE)$_4$-Palm).

In a particular embodiment of the invention, a peptide of the invention has an amino acid sequence selected from the group consisting of SEQ ID NO: 9, 11, 13-20, 23-43, 45-49, 56-58, 60-119, 121-177 and 180-193.

As indicated here-above and illustrated in the enclosed examples, these peptides are particularly advantageous in that they all have an $EC_{50}$ lower or equal to 15 nM.

In particular, a peptide of the invention has an amino acid sequence selected from the group consisting of SEQ ID NO: 14-20, 23-43, 45-49, 56, 57, 60-119, 121-125, 127-133, 135-160, 162, 164-177 and 180-193.

As illustrated in the enclosed examples, the peptides according to this embodiment are particularly advantageous in that they all have an $EC_{50}$ lower or equal to 5 nM.

In another particular embodiment of the invention, a peptide of the invention has an amino acid sequence selected from the group consisting of SEQ ID NO: 14-20, 26, 27, 30, 31, 33, 36, 38-43, 45, 46, 48, 56, 60, 61, 63-76, 79-86, 88-93, 98-113, 115, 116, 121-125, 128-131, 133, 135-143, 145, 146, 148-154, 156-160, 162, 164-174, 182-189 and 191-193.

As illustrated in the enclosed examples, the peptides according to this embodiment are particularly advantageous in that they all have an $EC_{50}$ lower or equal to 1 nM.

In another particular embodiment of the invention, a peptide of the invention has an amino acid sequence selected from the group consisting of SEQ ID NO: 14-20, 27, 38-43, 48, 60, 61, 64, 65, 67, 70, 72-75, 79, 81, 82, 84, 88-93, 99-106, 108-112, 115, 122-125, 128, 130, 131, 133, 136-143, 145, 146, 148-154, 156-160, 162, 165-171, 173, 174, 182-187, 189, 191, and 193.

As illustrated in the enclosed examples, the peptides according to this embodiment are particularly advantageous in that they all have an EC50 lower or equal to 0.5 nM.

In another particular embodiment of the invention, a peptide of the invention has an amino acid sequence selected from the group consisting of SEQ ID NO: 14, 16, 39-42, 74, 75, 82, 84, 89-91, 99, 102, 103, 105, 122, 125, 133, 136, 138, 142, 146, 150, 152, 156, 157, 159, 167-170, 183 and 185.

As illustrated in the enclosed examples, the peptides according to this embodiment are particularly advantageous in that they all have an $EC_{50}$ lower or equal to 0.1 nM.

In a particular embodiment, a peptide of the invention has the amino acid sequence of reference SEQ ID NO: 81, 150 or 170.

A peptide of the invention may be produced by any technique known per se in the art, such as, without limitation, any chemical, biological, genetic or enzymatic technique, either alone or in combination. Knowing the amino acid sequence of the desired sequence, one skilled in the art can readily produce said polypeptides, by standard techniques for production of polypeptides, even if non-natural amino acids are used.

For instance, the peptides of the invention can be synthesized using well-known solid phase method, in particular using a commercially available peptide synthesis apparatus (such as that made by Applied Biosystems, Foster City, Calif., Gyros Protein technologies, Tucson, Ariz. or CEM corporation, Matthews, N.C.) and following the manufacturer's instructions.

Examples of appropriate methods are illustrated in the enclosed examples.

A peptide of the invention can be labelled with at least one detectable molecule or substance, in particular selected from the group consisting of enzymes, prosthetic groups, fluorescent materials, luminescent materials, bioluminescent materials and radioactive materials.

However, it is important that said label does not alter or prevent said peptide from having its biological activity of interest as defined previously, i.e. does not prevent or alter the peptide ability to bind and activate the RXFP1 receptor.

Preferred detectable molecules or substances for the nanomaterial support are those which can be detected externally in a non-invasive manner following in vivo administration.

Detectable molecules or substances are well known to the man skilled in the art.

Such labelled peptide of the invention can be used in a diagnosis and/or imaging method.

The inventors have moreover observed that the half-life, and in particular the in-vivo half-life of the peptides of the invention is significantly superior to the one of Relaxin.

Indeed, Relaxin is rapidly cleared by the kidney and cannot be used in chronic setting. The recombinant hormone has a very short half-life in vivo (as illustrated in the monkey and human in B. L. Ferraiolo et al. Pharm. Res. (1991), 8, 1032 and in S. A. Chen et al. Pharm. Res. (1993), 10, 834) and requires intravenous delivery. The half-life of Relaxin is indeed so short that continuous infusion might be required for several hours in an hospital setting for its administration to an individual in need thereof, in particular an individual suffering from an acute disease or disorder, such as for example an acute heart failure. Replacement of Relaxin in this treatment by Relaxin-peptides having an improved in vivo half-life advantageously allows the replacement of this constraining treatment by a simpler one, such as a single daily administration by, for example, the intravenous or subcutaneous route.

Accordingly, the Relaxin peptides of the invention, that possess the ability of Relaxin to activate RXFP1, and more particularly peptides that are long lasting agonists of RXFP1, have the potential for wider therapeutic applications including acute or chronic heart failure.

Compositions and Medicaments

The present application also relates to a medicament or a pharmaceutical composition comprising at least one peptide of the invention as described above, or one of its pharmaceutically acceptable salt or solvate thereof, and at least one pharmaceutically acceptable carrier.

At least one peptide of the invention is present in a medicament or pharmaceutical composition of the invention as active principle.

A composition or a medicament of the invention is in a form suitable for mammalian administration.

A composition or a medicament of the invention can be administered, for example, orally, parenterally, intravenously, rectally, transdermally, topically or by inhalation. In particular, a composition according to the invention is administered by the intravenous or subcutaneous route.

According to a particular embodiment, the pharmaceutically acceptable carrier of a composition of the invention is suitably selected from the group consisting of an injectable carrier liquid such as sterile water for injection; and an aqueous solution such as saline.

A composition or a medicament of the invention can comprise a content of peptides of the invention comprised between 0.01 mg/mL and 30 mg/mL, in particular between 0.3 mg/mL and 3 mg/mL.

A medicament or a pharmaceutical composition of the invention can comprise at least one peptide of the invention as sole active principle or can also comprise at least one other active principles, as long as said other active principle does not prevent the biological activity of the peptide according to the invention.

A pharmaceutical composition or a medicament according to the invention can further comprise at least one antioxidant, dispersant, emulsifier, antifoam, flavouring, preservative, solubilizer and/or colour, as long as this/these additional substances do not prevent the biological properties of the peptides according to the invention.

Sterile compositions of the invention for parenteral administration may in particular be aqueous or non-aqueous solutions, suspensions or emulsions. Solvents or vehicles that can be used include water, propylene glycol, a polyethylene glycol, plant oils, in particular olive oil, injectable organic esters, for example ethyl oleate, or other suitable organic solvents. These compositions may also comprise adjuvants, in particular wetting agents, tonicity agents, emulsifiers, dispersants and stabilisers. The sterilisation may be performed in several ways, for example by aseptic filtration, by incorporating sterilising agents into the composition, by irradiation or by heating. They may also be prepared in the form of sterile solid compositions that may be dissolved at the time of use in sterile water or any other injectable sterile medium.

The compositions for topical administration may be, for example, nasal drops or aerosols.

For subcutaneous, intramuscular or intravenous administration, the peptides of the invention used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

In a particular embodiment, a composition of the invention, a medicament of the invention, or a peptide of the invention, or one of its pharmaceutically acceptable salt or solvate thereof, is administered to an individual by the parenteral route, and is in particular transdermaly, intravenously, subcutaneously or intramuscularly, in particular intravenously or subcutaneously administered.

Methods for preparing parenterally administrable compositions are apparent to those skilled in the art, and are for example described in more detail in Remington's Pharmaceutical Science, $15^{th}$ ed., Mack Publishing Company, Easton, Pa.

The administration of a composition of the invention or of a peptide of the invention to an individual can be a systemic administration or an administration localized to a tissue, organ and/or site of the individual organism where the presence of, for example a fibrosis, is known, expected or needs to be determined.

Use of the Peptides and Compositions

The present invention relates to a peptide according to the invention, its pharmaceutically acceptable salt or solvate thereof, according to the invention, for its use as a medicament.

Moreover, the invention also relates to a pharmaceutical composition according to the invention for its use as a medicament.

Furthermore, the present invention relates to a peptide of the invention, its pharmaceutically acceptable salt or solvate thereof, or a pharmaceutical composition of the invention for its use in the treatment and/or prevention of various diseases or conditions implicating the RXFP1 receptor, more particularly in the treatment and/or prevention of diseases or conditions selected from:
 the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia;
 the group consisting of heart and vascular diseases, in particular from the group consisting of acute or chronic heart failure, systolic or diastolic heart failure, coronary artery disease, atherosclerosis, microvascular angina and cardiovascular complication of diabetes; and/or
 the group consisting of renal failures in particular renal dysfunction in cirrhosis, chronic kidney disease and acute kidney injury.

In one aspect, such peptide, pharmaceutically acceptable salt or solvate thereof, or pharmaceutical composition according to the invention, is administered once a day, in particular by the intravenous or subcutaneous route.

The dosage of the peptide, or of its pharmaceutically acceptable salt or solvate thereof, to be administered, and the frequency of administration, depend on the desired effect, the potency and duration of action of the compounds used; additionally also on the nature and severity of the disease or condition to be treated and on the sex, age, weight and individual responsiveness of the mammal to be treated. In general, the physician will determine the appropriate dosage as a function of the age and weight and all the other factors specific to the individual to be treated.

Also provided herein is a method for preventing and/or treating a disease or condition implicating the Relaxin receptor RXFP1 comprising administering to an individual in need of said prenvention and/or treatment at least one peptide of the invention, a pharmaceutically acceptable salt or solvate thereof or a pharmaceutical composition of the invention comprising at least one peptide according to the invention or a therapeutically effective amount of least one peptide of the invention, a pharmaceutically acceptable salt or solvate thereof or a pharmaceutical composition of the invention comprising at least one peptide according to the invention.

As previously indicated, said disease or condition is in particular selected from:
 the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia;
 the group consisting of heart and vascular diseases, in particular from the group consisting of acute or chronic heart failure, systolic or diastolic heart failure, coronary artery disease, atherosclerosis, microvascular angina and cardiovascular complication of diabetes; and/or
 the group consisting of renal failures in particular renal dysfunction in cirrhosis, chronic kidney disease and acute kidney injury.

In particular, said disease or condition is selected from:
 the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia; and/or
 the group consisting of heart and vascular diseases, in particular from the group consisting of acute or chronic heart failure, systolic or diastolic heart failure, coronary artery disease, atherosclerosis, microvascular angina and cardiovascular complication of diabetes.

It is further described the use of at least one peptide according to the invention, its pharmaceutically acceptable salt or solvate thereof, or of a pharmaceutical composition according to the invention for treating and/or preventing a disease or condition selected from:
 the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia;
 the group consisting of heart and vascular diseases, in particular from the group consisting of acute or chronic heart failure, systolic or diastolic heart failure, coronary artery disease, atherosclerosis, microvascular angina and cardiovascular complication of diabetes; and/or
 the group consisting of renal failures in particular renal dysfunction in cirrhosis, chronic kidney disease and acute kidney injury;
and in particular for treating and/or preventing a disease or condition selected from:
 the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia; and/or
 the group consisting of heart and vascular diseases, in particular from the group consisting of acute or chronic heart failure, systolic or diastolic heart failure, coronary artery disease, atherosclerosis, microvascular angina and cardiovascular complication of diabetes.

The present invention is illustrated by the following examples, given purely for illustrative purposes.

EXAMPLES

Example 1: Synthesis of the Peptides of the Invention

Material Used

Various rink amide resins were used for the synthesis of C-terminal amides peptides of the invention:
- 4-(2',4'-Dimethoxyphenyl-Fmoc-aminomethyl)phenoxy resin, sold by Chem-Impex; or
- 4-(2',4'-Dimethoxyphenyl-Fmoc-aminomethyl)phenoxy acetamido methyl resin, sold by Millipore Merck;

They were loaded in the range of 0.2 to 0.4 mmol/g.

Fmoc (fluorenylmethyloxycarbonyl) protected natural amino acids were purchased from different sources, i.e. Protein Technologies Inc., Merck Biosciences, Novabiochem, Iris Biotech, Bachem, Chem-Impex International or MATRIX Innovation.

The following standard amino acids were used throughout the syntheses: Fmoc-L-Ala-OH, Fmoc-L-Arg(Pbf)-OH, Fmoc-L-Gln(Trt)-OH, Fmoc-L-Glu(OtBu)-OH, Fmoc-L-Glu-OtBu, Fmoc-Gly-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Ser(tBu)-OH, Fmoc-L-Thr(tBu)-OH, Fmoc-L-Trp(Boc)-OH, Fmoc-L-Tyr(tBu)-OH and Fmoc-L-Val-OH.

In addition, the following special amino acids were purchased from the same suppliers as above: Fmoc-L-hArg(Pbf)-OH, Fmoc-L-Cit-OH, Nα-Fmoc-Nω,Nω'-dimethyl-L-Arg-OH (symmetrical) hydrochloride, Fmoc-L-Arg(Me,Pbf)-OH, Fmoc-L-hLys(Boc)-OH, Fmoc-L-Orn(Boc)-OH, Fmoc-L-Lys(Me)3-OH Chloride, Dde-L-Lys(Fmoc)-OH, ivDde-L-Lys(Fmoc)-OH, Fmoc-L-Lys(Dde)-OH, Fmoc-L-Lys(ivDde)-OH, Fmoc-L-Lys(Mmt)-OH, Fmoc-L-Lys(Mtt)-OH, Fmoc-L-Lys(aloc)-OH, Fmoc-L-Lys(Ac)-OH, Fmoc-Aib-OH, Fmoc-L-α-Me-Ser(tBu)-OH, Fmoc-L-α-Me-Lys(Boc)-OH, Fmoc-L-α-Me-Arg(Pbf)-OH, Fmoc-L-α-Me-Leu-OH, Fmoc-L-Nle-OH and Fmoc-L-1-Nal-OH, Fmoc-L-2-Nal-OH Fmoc-5-Wox-OH, Fmoc-Pfp-OH, Fmoc-L-α-Me-Trp-OH, Fmoc-L-α-Me-Phe-OH.

| | |
|---|---|
| Ac | Acetyl |
| Aloe | Allyloxycarbonyl |
| Boc | Tert-Butyloxycarbonyl |
| tBu | Tert-Butyl |
| cAMP | Cyclic adenosine monophosphate |
| Dde | 1-(4,4-Dimethyl-2,6-dioxocyclohex-1-ylidene)ethyl |
| ivDde | 1-(4,4-dimethyl-2,6-dioxocyclohex-1-ylidene)-3-methylbutyl |
| DCM | Dichloromethane |
| DIC | N,N'-Diisopropylcarbodiimide |
| DIEA | N,N-Diisopropyl ethylamine |
| DMF | N,N-Dimethylformamide |
| DODT | 2,2'-(Ethylenedioxy)diethanethiol |
| EDT | 1,2-ethanedithiol |
| Fmoc | Fluorenylmethyloxycarbonyl |
| TFA | Trifluoroacetic acid |
| TIS, TIPS | Tri-isopropyl Silane |
| HATU | (2-(7-Aza-1H-benzotriazol-1-yl)-N,N,N',N'-tetramethylaminium hexafluorophosphate) |
| HPLC | High Performance Liquid Chromatography |
| HTRF | HTRF Homogenous Time Resolved Fluorescence |
| LC/MS | Liquid Chromatography/Mass Spectrometry |
| Laur | Lauroyl |
| Mmt | Monomethoxy-trityl |
| Mtt | 4-Methyl-trityl |
| Myr | Myristoyl |
| NMP | 1-methylpyrrolidin-2-one |
| Oxyma | Ethyl 2-cyano-2-(hydroximino)acetate (oxyma pureTM) |
| Pbf | 2,2,4,6,7-pentamethyldihydrobenzofuran-5-sulfonyl |
| RP-HPLC | Reversed-phase high performance liquid chromatography |
| RT | Retention Time |
| TFA | Trifluoroacetic acid |
| Trt | Trityl, Triphenylmethyl |
| UV | Ultraviolet |
| UPLC | Ultra high Performance Chromatography |

For synthesizing the C-terminally lipidated peptides of the invention, orthogonally protected lysine was used as indicated here-after.

1.A. First General Method Used for Synthesizing the Peptides of the Invention

Figure 2:
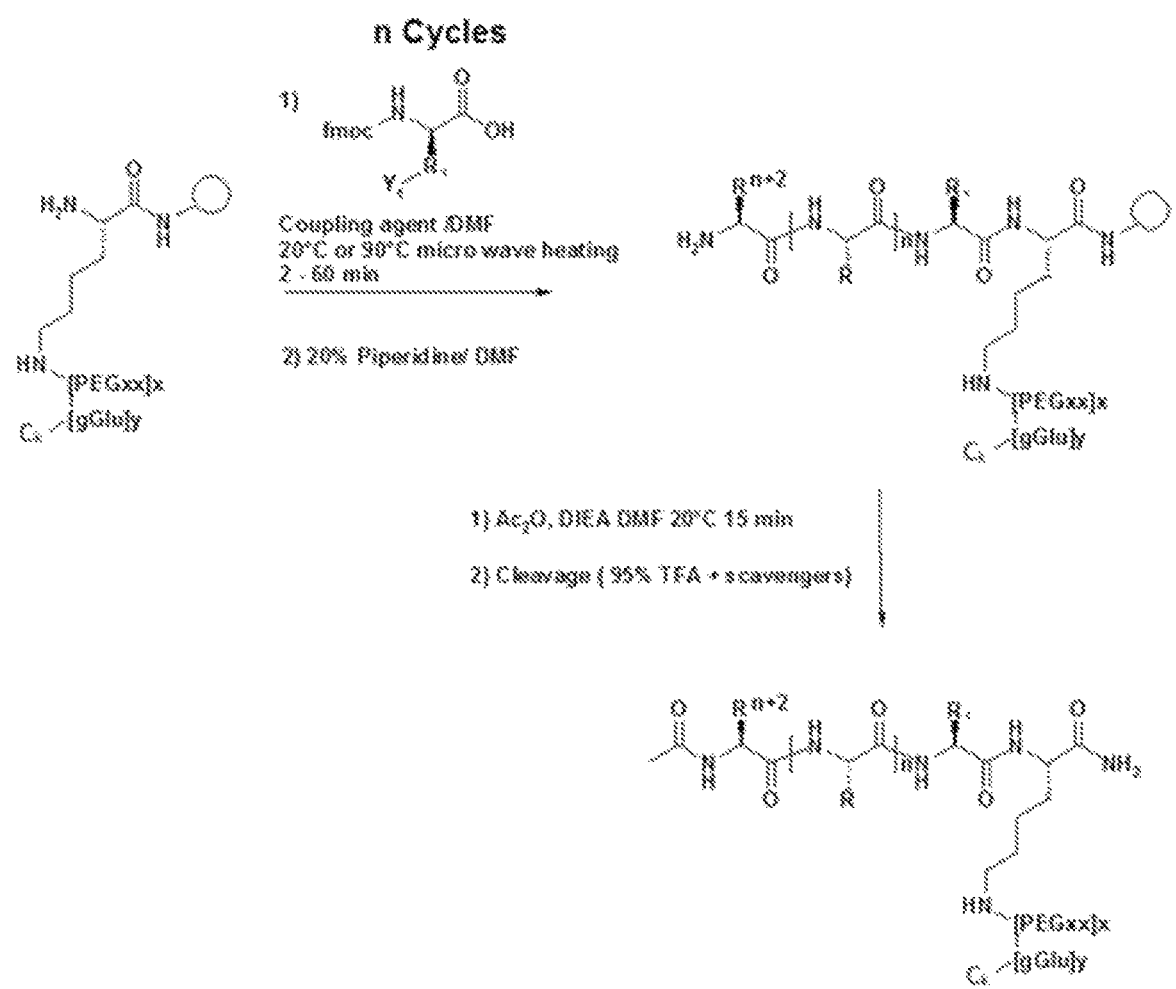

Several of the peptides according to the invention of sequence SEQ ID NO: 1-193 have been synthesized on the basis of the method represented in FIGS. 1 and 2.

Dde-Lys(Fmoc)-OH (or ivDde-Lys(Fmoc)-OH) was coupled to 0.2 mmol of Rink amide AM resin using 3eq DIC (N,N'-Diisopropylcarbodiimide) and 3 eq HOAt (1-Hydroxy-7-aza-1H-benzotriazole) in DMF (N,N-Dimethylformamide) at 20° C. overnight.

The acylation reaction was monitored by ninhydrin (Kaiser) test. Negative test: no color on and/or above the resin, indicating complete acylation.

The resin was treated with 20% v/v piperidine in DMF to remove Ne-Fmoc protecting group (2×30 min) and washed 3 times with DMF.

The PEGxx group of the Z group, if present in the peptide of the invention, was introduced by single acylation with 3 eq of Fmoc-PEGxx-OH for 1 h with 3 eq of DIC (N,N'-Diisopropyl carbodiimide) and 3 eq of HOAt monitoring the reactions by ninhydrin (Kaiser) Test. The Fmoc removal and Fmoc-PEGxx-OH coupling steps were repeated x times (x=0-5), i.e. as many times as necessary depending of the peptide of the invention.

Then resin was treated with 20% v/v piperidine in DMF as to remove amino-PEGxx protecting group (2×30 min) and washed 3 times with DMF.

Then, Fmoc-Glu-OtBu ((4S)-5-tert-butoxy-4-(9H-fluoren-9-ylmethoxycarbonylamino)-5-oxo-pentanoic acid), if gE is present in the Z group of the peptide of the invention, was introduced by performing single coupling with 3 eq. of amino acid for 1 h with 3 eq. of DIC and 3 eq. of HOAt monitoring the reactions by Kaiser Test.

The Fmoc removal and Fmoc-Glu-OtBu coupling steps were repeated y times (y=1-5)

Then, after removal of the Fmoc protecting group, the side chain was lipidated using 3 eq. of Ck lauric acid ($C_{12}$), myristic acid ($C_{14}$), pentadecanoic acid ($C_{15}$), palmitic acid ($C_{16}$), hepatdecanoic acid ($C_{17}$), stearic acid ($C_{18}$), eicosanoic acid ($C_{20}$) or docosanoic acid ($C_{22}$), 3eq. DIC and 3 eq. HOAt in NMP (1-methylpyrrolidin-2-one). The reaction was monitored by Kaiser Test and left overnight.

Alternative acylation method included the use the corresponding acyl chlorides and DIEA (N,N-diisopropyl ethylamine) as a base in dichloromethane or the use of N-succinimidyl esters of the above acids and DIEA (N,N-diisopropyl ethylamine) as a base in DMF. The latter are prepared separatelly by activating the acids with N-hydroxysuccinimide and DIC in ethyl acetate.

Deprotection of Dde (or ivDde) was performed percolating 80 ml of a solution of hydrazine 5% in DMF followed by DMF wash (×3). The reaction was monitored by Kaiser Test.

Once the $X_{37}$ group was assembled, the resin was transferred into the CEM Liberty microwave peptide synthesizer to perform the rest of the sequence assembly (see FIG. 2).

The peptide was synthesized using the standard protocol for 0.1 to 0.2 mmol scale.

The entire synthesis was run in DMF as solvent.

Standard heating protocol: irradiation at 170 watts, 75° C., 15 sec. then irradiation at 30 watts, 90° C., 120 sec.

Deprotection was performed with 20% v/v piperidine in DMF, followed by 3 DMF washing steps.

Heating protocol for deprotection: irradiation at 170 watts, 75° C., 15 sec. then irradiation at 30 watts, 90° C., 50 sec.

Amino acid couplings were performed using 5 eq. of Fmoc-AA as 0.2 M solutions in DMF using 5 eq. N,N'-Diisopropylcarbodiimide (DIC) 0.5M and 5 eq. Oxyma (Ethyl 2-cyano-2-(hydroximino)acetate (oxyma Pure™)) 1M as coupling reagents.

For better final yield, each amino-acid required double couplings at 90° C. for 120 seconds. For 2-aminoisobutyric acid at position $X_{21}$ of the formula (I) according to the invention, a triple coupling at 90° C. for 2 minutes was used.

At the end of the synthesis, Fmoc deprotection was performed manually with 20% V/V piperidine in DMF two times 30 minutes.

Acetylation was performed at N-terminus by treatment with 5-10 eq. of acetic anhydride and 5-10 eq. DIEA in DMF for 15 min. Then the resin containing the fully protected peptide was washed with DCM/DMF/DCM, 3 times each and dried under vacuum.

1.B. Second General Method Used for Synthesizing the Peptides of the Invention

Figure 3:
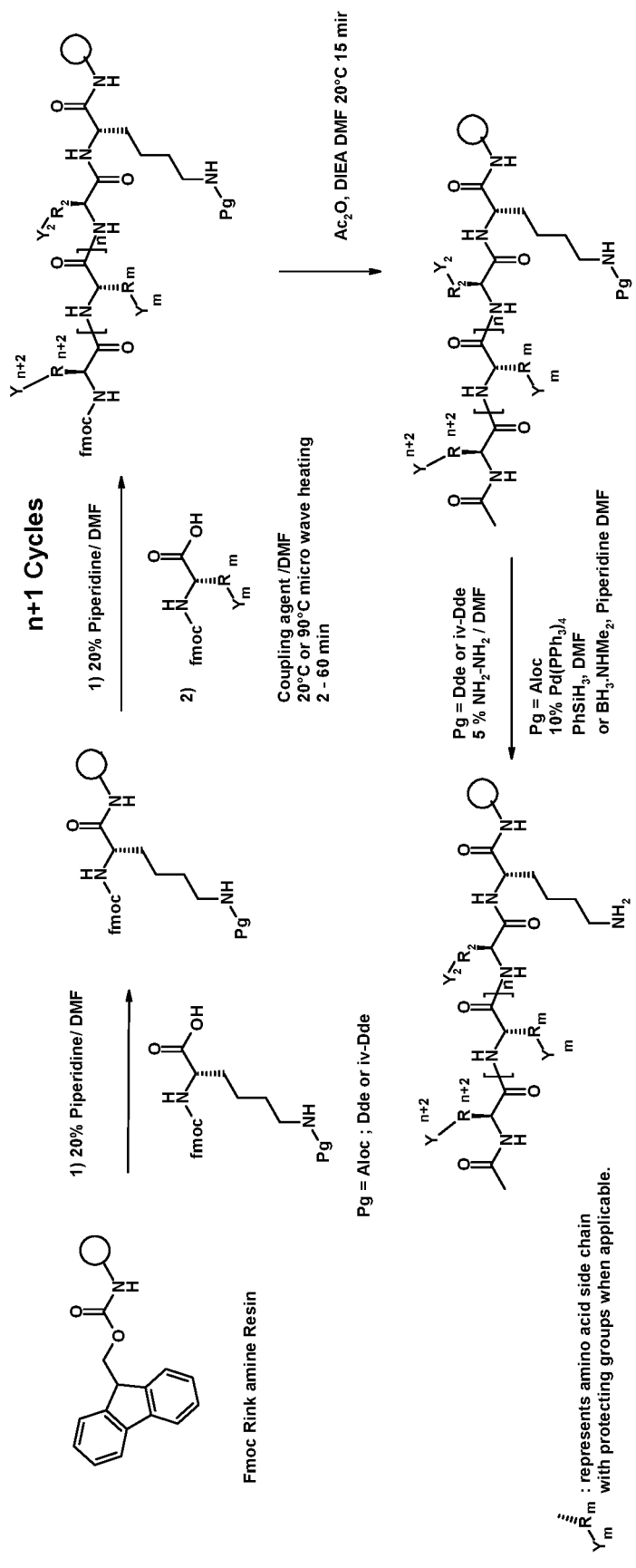
FIGS. 3 and 4 are the two parts of a schema representing a second general method used for synthesizing the peptides of the invention. With this method, the above mentioned Z group is installed after the peptides assembly.
Figure 4:
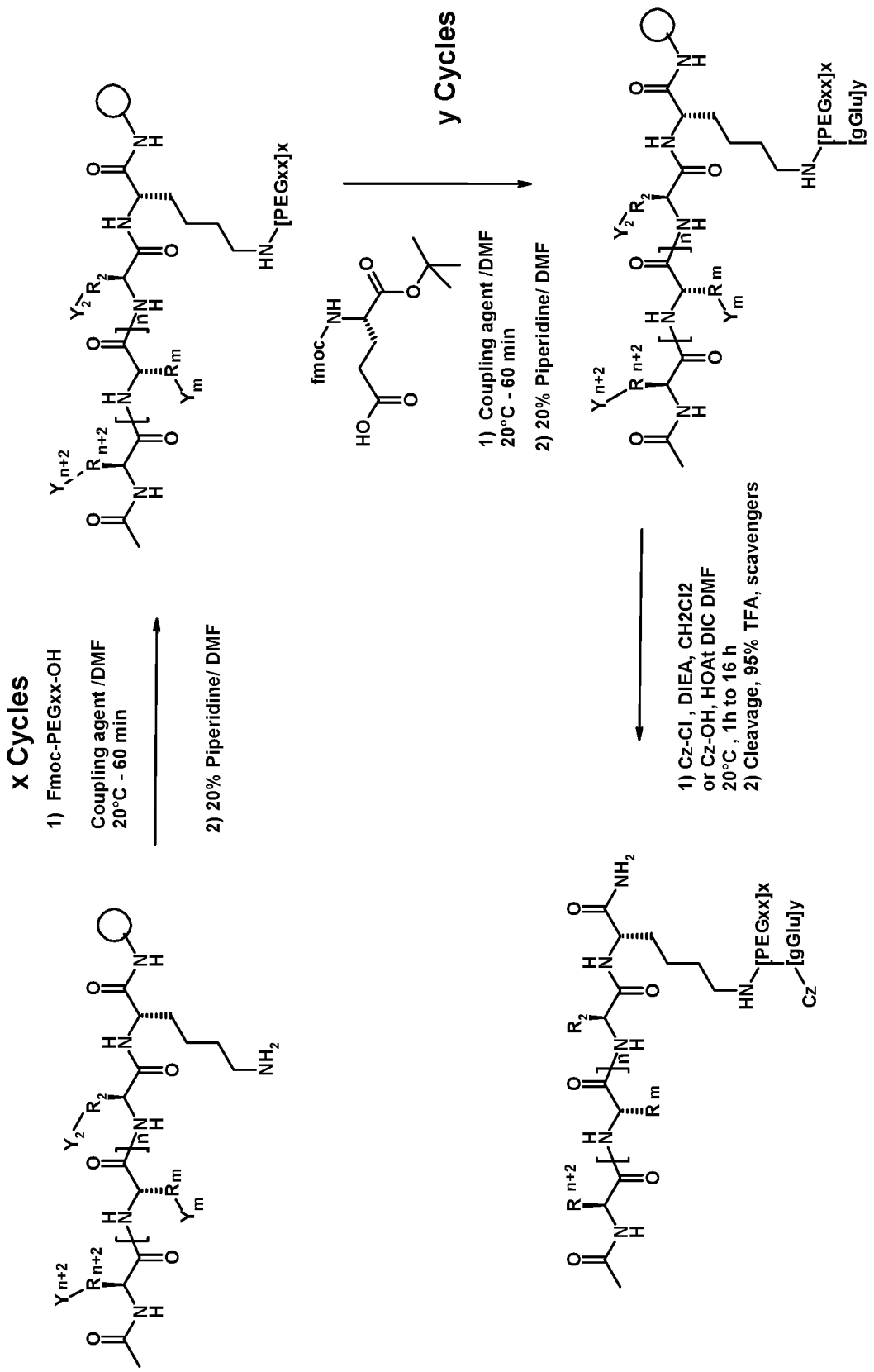

Several of the peptides according to the invention of sequence SEQ ID NO: 1-193 have been synthesized on the basis of the method represented in FIGS. 3 and 4.

In this second option, the Z group according to the formulae of the invention was installed after the peptide assembly.

Fmoc-Lys(Dde)-OH, Fmoc-Lys(ivDde)-OH, Fmoc-Lys(aloc)-OH, Fmoc-Lys(Mtt)-OH or Fmoc-Lys(Mmt)-OH were first attached to the resin. Then the peptide sequence was constructed using the standard Fmoc chemistry protocol described in Example 1.A. here-above.

Then the C-terminal Lysine ($X_{37}$) NE-protecting group (Dde, ivDde, aloc, MTT or MIVIT) were removed using diluted hydrazine in DMF (Dde, ivDde), Phenylsilane or dimethyl amino borane in the presence of Palladium(0) catalyst in DCM (aloc) or 1% TFA in DCM (Mtt or Mmt).

Then the Z groups were attached to the side chain nitrogen of the $X_{37}$ lysine on solid support according to the following steps:

First part of the steps are represented in FIG. 3.

Second part of the steps are represented in FIG. 4.

Rink amide AM resin was manually acylated with 3 eq of Fmoc-Lys(Dde)-OH, Fmoc-Lys(ivDde)-OH, Fmoc-Lys(Mtt)-OH, Fmoc-Lys(Mmt)-OH or Fmoc-Lys(Aloc)-OH using 3 eq DIC and 3 eq HOAt in DMF as coupling agents at 20° C. overnight.

The acylation reaction was monitored by ninhydrin (Kaiser) test. Negative test: no color on the resin, indicating complete acylation.

Afterwards, the resin was transferred into the CEM Liberty microwave peptide synthesizer for the sequence assembly as indicated in Example 1.A. The standard protocol was used for 0.1 to 0.2 mmol scale.

The entire synthesis was run in DMF as solvent.

Standard heating protocol: irradiation at 170 watts, 75° C., 15 sec. then irradiation at 30 watts, 90° C., 120 sec.

Deprotection was performed with 20% v/v piperidine in DMF, followed by 3 DMF washing steps.

Heating protocol for deprotection: irradiation at 170 watts, 75° C., 15 sec. then irradiation at 30 watts, 90° C., 50 sec.

Amino acid couplings were performed using 5 eq. of Fmoc-AA as 0.2 M solutions in DMF using 5 eq. N,N'-diisopropylcarbodiimide (DIC) 0.5M and 5 eq. Oxyma (ethyl 2-cyano-2-(hydroximino)acetate (oxyma Pure™)) 1M as coupling reagents.

For better final yield, each amino-acid required double couplings at 90° C. for 120 seconds. For 2-aminoisobutyric acid at position $X_{21}$ of the formula (I) according to the invention, a triple coupling at 90° C. for 2 minutes was used.

At the end of the synthesis, Fmoc deprotection was performed manually with 20% V/V piperidine in DMF two times 30 minutes.

Acetylation was performed at N-terminus by treatment with 10 eq. of acetic anhydride in DMF for 15 min. Then the resin containing the fully protected peptide was washed with DCM/DMF/DCM 3 times each and dried under vacuum.

When the lysine in position $X_{37}$ is protected on its side chain by Dde or iv-Dde, resin-peptide was transferred into a 50 ml polypropylene syringe. 80 ml of a solution of hydrazine 5% in DMF was percolated through the resin followed by DMF wash (3 times). The reaction was monitored by Kaiser Test.

When the lysine in position $X_{37}$ is protected on its side chain by the allyl-oxy-carbonyl group (aloc), resin-peptide was transferred into a 50 ml polypropylene syringe and swelled in dichloromethane and treated with 20 eq. phenylsilane ($PhSiH_3$) or borane dimethylamine complex (($CH_3$)$_2$NH.BH$_3$), piperidine and 10% (mol/mol) tetrakis-(triphenylphosphine)palladium ($Pd(PPh_3)_4$) for 1 h under argon. This treatment was repeated until no starting aloc protected peptide could be detected by UPLC/MS analysis after cleavage of an aliquot part of the resin.

When the reaction is complete, the resin was washed with dichloromethane, 1% DIEA in DMF, 5% diethyl-dithio-carbamate in DMF, DMF and dichloromethane (3 times each).

The PEGxx group(s) of the Z group was introduced, if applicable for a given peptide of the invention, by single acylation with 3 eq. of Fmoc-PEGxx-OH for 1 h with 3 eq. of DIC and 3 eq. of HOAt monitoring the reactions by ninhydrin (Kaiser) Test. Then the resin was treated with 20% v/v piperidine in DMF to remove Fmoc protecting group (2×30 min) and washed 3 times with DMF. The Fmoc-PEGxx-OH coupling, Fmoc removal and washing steps were repeated x times (x=0-5).

Then Fmoc-Glu-OtBu ((4S)-5-tert-butoxy-4-(9H-fluoren-9-ylmethoxycarbonylamino)-5-oxo-pentanoic acid), if gE present in the Z group of the peptide of the invention, was introduced by performing single coupling with 3 eq. of amino acid for 1 h with 3 eq. of DIC and 3 eq of HOAt monitoring the reactions by Kaiser Test.

Then resin was treated with 20% v/v piperidine in DMF as to remove Fmoc protecting group (2×30 min) and washed 3 times with DMF. The Fmoc removal and Fmoc-Glu-OtBu coupling steps were repeated y times (y=1-5).

Then, the side chain was lipidated using 3 eq. of Ck lauric acid ($C_{12}$), myristic acid ($C_{14}$), pentadecanoic acid ($C_{15}$), palmitic acid ($C_{16}$), hepatdecanoic acid ($C_{17}$), stearic acid ($C_{18}$), eicosanoic acid ($C_{20}$) or docosanoic acid ($C_{22}$) using 3eq. DIC and 3 eq. HOAt in NMP, using the corresponding acyl chlorides and DIEA as a base in dichloromethane or using the corresponding N-succinimidyl esters and DIEA as base in DMF.

The reaction was monitored by Kaiser Test and left overnight.

Then the resin containing the fully protected peptide was washed with DCM/DMF/DCM 3 times each and dried under vacuum.

1.C. Synthesis Particularity for Certain Peptides of the Invention

For peptides for which e and/or f are difference from 0 in the general formulae of the invention, the synthesis was performed as described in examples 1.A. or 1.B. above. Fmoc-PEGxx- and/or Fmoc-L-Glu-OtBu building blocks were introduced in the main peptide chain, or amino acid chain, as any regular amino-acid using the same coupling procedures, i.e. peptide coupling.

1.D. Peptide-Resin Cleavage

Upon completion of solid phase synthesis, the peptide was cleaved from the solid support by treatment with cleavage reagent B: TFA/phenol/$H_2O$/TIPS (87.5%/5%/5%/2.5%/25 ml) for 3 h. (TIPS stands for Tri-isopropylsilane)

In certain instances, addition of a dithiol such as 1,2-ethane dithiol or DODT (2,2'-(ethylenedioxy)diethanethiol) may be advantageous (e.g. cleavage reagent K). The TFA solution containing the peptide was filtered and concentrated under reduced pressure at T<30° C.

The desired product was precipitated with ice-cold MTBE (methyl tert-butyl ether) or diethyl ether and centrifuged at 3000 rpm for 30 min. The centrifuged pellet was then washed with ice-cold diethyl ether and centrifuged. This process was repeated three times.

In some instances it may be necessary to process the crude peptide to remove undesired by-products such as TFA esters, $CO_2$ adduct on indole nitrogen of tryptophan (carbamic acid) and 2-t-butyl-sulfanylethyl adduct on methionine residues.

To remove $CO_2$ adduct on indole nitrogen of tryptophan, the crude peptide was taken up in water containing 10-20% $CH_3CN$, 5 mg/ml and lyophilized.

To remove 2-t-butyl-sulfanylethyl adduct on Met, the crude peptide was dissolved (2 mg/ml) in a solution of $H_2O$/$CH_3CN$ (50:50 v/v) containing 0.1% formic acid.

The mixture was gently stirred at 37° overnight.

To remove TFA esters, the crude peptide was dissolved (2 mg/ml) in a solution of $H_2O$/$CH_3CN$ (50:50 v/v) containing 0.1% formic acid. The mixture was gently stirred at 37° for 1-4 h.

In both cases, the crude peptide solution thus obtained was partially concentrated under reduced pressure and at T<30° C. and lyophilized.

1.E. Purification Step

Following any of the above methods indicated for synthesizing a peptide of the invention, said peptide was purified before being used.

80 mg of peptide were dissolved in 1.5 mL DMSO and purified by Reverse Phase High Pressure Liquid Chromatography (RP-HPLC). The RP-HPLC is described hereunder.

A GX271 Liquid Handler, 333/334 pumps, and UV/VIS 151 Gilson system was used.

Two different systems were used in order to purify said peptides:

System A
Column Reprosil C4 5 µm 120 Å. 250×40 mm;
Solution A: 0.1% Trifluoroacetic acid (TFA) in $H_2O$;
Solution B: 0.1% TFA in Acetonitrile;
Gradient: 30% B for 5 min; 30% B to 50% B in 20 min;
Flow rate: 60 ml/min.

System B
Column Waters CSH C18 5 µm 250×50 mm, or Waters Sunfire C18 10 µM 250×50 mm;
Solution A=0.1% TFA in water;
Solution B=0.1% TFA in acetonitrile;
Gradient: from 1% B to 18% B in 5 min; from 18% B to 28% B in 10 min; 28% B for 15 min; from 28% B to 48% B in 10 min; then column wash from 48% B to 90% B in 10 min;
Flow rate: 150 ml/min.

The peptide of interest eluted in the 35-40 min time window.

The gradient was slightly adjusted according to the polarity of each peptide as characterized by its retention time on an analytical UHPLC System.

The fractions containing the pure peptide were then partially concentrated under reduced pressure at T<35° C. and lyophilized until constant weight.

For certain uses (eg in-vivo testing), it is advantageous to exchange the TFA salt to the acetate salt. Three corresponding methods were used and are described in the following part 1.F.

1.F. Acetate Exchange (i) Acetate Exchange with TOYOPEARL® DEAE 650 C (Tosoh Corporation)

The ion exchange was performed using a TOYOPEARL® DEAE 650 C grade resin (a weak anion exchange resin).

120 ml of resin was washed sequentially with 15 volumes of NaOH 1M, 5 volumes of $H_2O$, 5 volumes of acetic acid 1.6M, 5 volumes of acetic acid 0.16M and finally 5 volumes of $H_2O$.

41.8 mg of peptide was then dissolved in 4 ml of distilled water, downloaded to the resin and gently mixed for 2 h.

Finally the peptide was collected by elution and washed with water and lyophilized.

Peptide Recovery: 35 mg (as acetate salt by F19 NMR (400 MHz) ns 1028).

(ii) Acetate Exchange with Sepharose HiTrap Q HP Column (Strong Anionic Exchange Comun)

In this second method, the ion exchange was performed using a HiTrap Q HP.

The column (5 ml bed volume) was connected to a peristaltic pump set at 48 (4.5 ml/min) and before loading the peptide it was washed with 50 ml (10 column volumes) of $H_2O$, 100 ml (20 column volumes) of a 1M solution of sodium acetate, 150 ml (30 column volumes) of $H_2O$ and with 50 ml (10 column volumes) of 0.16 M solution of acetic acid.

The pure peptide was dissolved in a 0.16 M acetic acid solution at 2 mg/ml, slowly loaded on the column and eluted at 4.5 ml/min.

The collected solution was freeze-dried.

The effectiveness of the ion exchange was attested by F19 NMR (400 MHz) ns 1028.

(iii) Acetate Exchange by RP-HPLC

The material used was the following:
Column Waters CSH C18 5 µm 250×50 mm, or Waters Sunfire C18 10 µM 250×50 mm;
Solution A=1% Acetic Acid in water;
Solution B=1% Acetic Acid in Acetonitrile;

After, previously purified peptide injection on the column, a 10 mM Ammonium Acetate solution in water was run for 10 minutes. Then the solvent system was switched to the following AB gradient:

Gradient: from 1% B to 7% B for 5 min; from 7% B to 17% B in 10 min; 17% B for 15 min; from 17% B to 27% B in 10 min; then column wash from 27% B to 95% B in 10 min.

Flow rate: 150 ml/min.

The peptide of interest was eluted in the 35-40 min time windows. The gradient was slightly adjusted according to the polarity of each peptide as characterized by its retention time on an analytical UHPLC System.

The fractions containing the pure peptide were then partially concentrated under reduced pressure at T<35° C. and lyophilized until constant weight.

The effectiveness of the ion exchange was attested by F19 NMR (400 MHz). ns 1028.

Example 2: Illustrative Synthesis of Specific Peptides of the Invention

2.A. Synthesis of Peptide Having the SEQ ID NO: 33

In a 20 mL syringe equipped with a filter 500 mg of Rink Amide AM LL resin (NovaBiochem cat #8.55 120); 0.2 mmol of active Fmoc amino function were swelled in 10 ml DMF mixture for 30 min. The solvent was filtered off and replaced by 12 mL of 20% v/v of piperidine in DMF. The syringe was agitated on an orbital table for 20 min. This deprotection procedure was repeated a second time and the resin was washed with DMF (2×10 ml) and dichloromethane (3×10 ml).

The resin was then suspended in 12 mL NMP and Fmoc-L-Lys(ivDDE)-OH) (344 mg, 0.6 mmol) was added as a solid followed by HOAt (82 mg, 0.6 mmol) and N,N'-Diisopropylcarbodiimide (DIC) (188 µL, 1.2 mmol). The syringe was agitated on an orbital table for 4 h and the acylation controlled by Kaiser Test. The resin was washed with DMF (2×10 ml) and dichloromethane (10 ml). Afterwards, the resin was transferred into the CEM Liberty Blue microwave peptide synthesizer.

Peptide synthesis was performed by using DIC 0.5M/Oxyma 1M in DMF.

All amino acids were introduced with double couplings at 90° C. for 2 minutes, with the exception of aminoisobutyrric acid for which a triple coupling at 90° for 2 minutes was performed. Fmoc-PEG$_{12}$-OH was introduced in the main peptide chain as any amino acid using the same coupling deprotection cycles.

At the end of the synthesis, the resin-peptide was transferred into a 50 mL polypropylene syringe and the peptide was acetylated at N-terminus with of acetic anhydride (472 µL, 5 mmol) in DMF (10 mL) for 20 minutes, repeating the cycle twice.

Then, the ivDDE protecting group on C-terminus lysine side chain was removed by percolating 100 mL of a solution of hydrazine 5% w/v in DMF, followed by DMF washes (5×20 ml). The reaction was monitored by Kaiser Test.

The three gamma-glutamic acids spacers were introduced by performing a double coupling of each Fmoc-Glu-OtBu.

Thus the following procedure was applied three times:

To the resin 12 ml of NMP were added followed by (4S)-5-tert-butoxy-4-(9H-fluoren-9-ylmethoxycarbonylamino)-5-oxo-pentanoic acid (Fmoc-Glu-OtBu) (283 mg, 0.8 mmol), HOAt (112 mg, 0.8 mmol) and DIC (250 µL, 1.6 mmol).

The syringe was agitated on an orbital table for 2 h. The resin was washed with DMF (2×20 mL) and the coupling was repeated a second time. The reaction was monitored by Kaiser Test. When needed, a triple coupling was performed. The resin was washed with DMF (2×20 mL) and dichloromethane (3×10 mL). Then to the resin, 12 mL of 20% v/v of piperidine in DMF was added. The syringe was agitated on an orbital table for 20 min. This deprotection procedure was repeated a second time and the resin was washed with DMF (2×20 mL) and dichloromethane (3×10 mL).

Finally, the peptide was acylated with stearic acid (284 mg, 1 mmol), HOAt (136 mg, 1 mmol) and DIC (252 mg, 2 mmol) activation in NMP (15 mL) for 2.5 h. The resin was washed with DMF (2×20 ml) and dichloromethane (3×10 mL) and dried under vacuum.

The cleavage of the peptide from the resin was performed using a solution phenol (1.25 g), water (1.25 mL) and TIPS (0.75 mL) in TFA (QSP 25 mL) for 2.5 hours at room temperature.

The resin was filtered off, and washed with 2×20 mL TFA. The combined filtrates were transferred to a 250 ml round bottom flask and partially concentrated under vacuum at T<30° C. and the peptide was precipitated by the addition of 100 mL cold MTBE and centrifuged at 3600 rpm for 30 minutes.

The centrifuged pellet was then washed with ice-cold diethyl ether and centrifuged. This process was repeated three times.

645 mg of crude peptide are obtained.

The crude peptide was dissolved (2 mg/mL) in a solution of $H_2O/CH_3CN$ (50:50 v/v) containing 0.1% formic acid and the mixture was gently stirred at 37° for 1 h, partially concentrated and lyophilized.

Purification was performed using purification system A and the fractions containing pure desired peptide were lyophilized. The peptide as trifluoroacetate salt was obtained as a white solid.

m=96 mg (10%);

UPLC/MS:

RT: 3.68 min. (Analytical condition E);

purity 91% (UV)

Observed mass m/z (ion type): 1412.2 (M+3H); 1059.4 (M+4H); 848.0 (M+5H).

2.B. Synthesis of Peptide Having the SEQ ID NO: 58

In a 20 mL syringe equipped with a filter 500 mg of Rink Amide AM LL resin (NovaBiochem cat #8.55 120), 0.2 mmol of active Fmoc amino function were swelled in 10 mL DMF mixture for 30 min.

The solvent was filtered off and replaced by 12 mL of 20% v/v of piperidine in DMF. The syringe was agitated on an orbital table for 20 min. This deprotection procedure repeated a second time and the resin was washed with DMF (2×10 mL) and dichloromethane (3×10 mL).

The resin was then suspended in 6 mL DMF and (S)-6-allyloxycarbonylamino-2-(9H-fluoren-9-ylmethoxycarbonylamino)-hexanoic acid (Fmoc-L-Lys(Aloc)-OH) (271 mg, 0.6 mmol) was added as a solid followed by HOAt (82 mg, 0.6 mmol) and N,N'-Diisopropylcarbodiimide (DIC) (94 µL, 0.6 mmol). The syringe was agitated on an orbital table for 4 h. The resin was washed with DMF (2×10 mL) and dichloromethane (10 mL).

The resin was placed in the CEM Liberty Blue reactor and the programmed sequence was run as described above.

Then the resin was transferred to a 50 mL syringe equipped with a filter and washed with 3×10 mL DCM and dried under vacuum. The resin weighed 1.2 g.

The resin was swelled in 10 mL DMF, DIEA (200 µl, 1.15 mmol) and acetic anhydride (104 µl, 1.1 mmol) were added and the syringe was agitated on an orbital table for 1.5 h. The solvent was filtered off and the resin was washed with DMF (10 mL) and 3×10 mL DCM and dried under vacuum. The resin weighed 1.2 g.

A solution of 45 mg (38.94 µmol) of tetrakis (triphenylphosphine) palladium (Pd(PPh$_3$)$_4$) in 100 mL degased DCM is prepared in a round bottom flask under argon.

To the syringe containing the resin 20 mL degased DCM and phenyl silane (0.256 mL, 2.1 mmol) were added under argon followed by 6 mL of the Pd(PPh$_3$)$_4$) solution. The syringe was agitated on an orbital table for 30 min.

This aloc deprotection procedure was repeated twice, and then the resin was washed with DCM (4×20 mL), 20 mL of a 2% v/v of DIEA solution in DMF, a solution of 5% w/v of sodium diethyldithiocarbamate in DMF (2×20 mL), DMF (5×20 mL) and DCM (5×20 mL) and dried under vacuum.

First PEG$_2$ unit was coupled as follows: To the resin 12 mL of DMF were added followed by 2-[2-[2-(9H-fluoren-9-ylmethoxy carbonylamino) ethoxy] ethoxy]acetic acid (Fmoc-PEG$_2$-OH) (232 mg, 0.6 mmol), HOAt (84 mg, 0.6 mmol) and DIC (94 µL, 0.6 mmol). The syringe was agitated on an orbital table for 16 h. The resin was washed with DMF (2×20 mL) and dichloromethane (3×10 mL).

After Fmoc deprotection a second PEG$_2$ unit was added: To the resin, 12 mL of 20% v/v of piperidine in DMF is added. The syringe was agitated on an orbital table for 20 min.

This deprotection procedure was repeated a second time and the resin was washed with DMF (2×20 mL) and dichloromethane (10 mL). To the resin 12 mL of DMF were added followed by 2-[2-[2-(9H-fluoren-9-ylmethoxy carbonylamino) ethoxy] ethoxy]acetic acid (Fmoc-PEG$_2$-0H) (232 mg, 0.6 mmol), HOAt (84 mg, 0.6 mmol) and DIC (94 µL, 0.6 mmol). The syringe was agitated on an orbital table for 16 h. The resin was washed with DMF (2×20 mL) and dichloromethane (10 mL).

Coupling of the three γ-glutamic acids units was achieved by performing three times the following procedure: to the resin, 12 mL of 20% v/v of piperidine in DMF was added. The syringe was agitated on an orbital table for 20 min. This deprotection procedure was repeated a second time and the resin was washed with DMF (2×20 mL) and dichloromethane (10 mL).

To the resin 12 mL of DMF were added followed by (4S)-5-tert-butoxy-4-(9H-fluoren-9-ylmethoxycarbonylamino)-5-oxo-pentanoic acid (Fmoc-Glu-OtBu) (212 mg mg, 0.6 mmol), HOAt (84 mg, 0.6 mmol) and DIC (94 µL, 0.6 mmol). The syringe was agitated on an orbital table for 16 h. The resin was washed with DMF (2×20 mL) and dichloromethane (3×10 mL).

Then a final Fmoc deprotection was performed by treating the resin two times with 12 mL of 20% v/v of piperidine in DMF and 20 min agitation each time.

After washing the resin with DMF (2×20 mL) and DCM (3×20 mL), palmitic acid coupling was performed. Palmitic acid (153 mg, 0.6 mmol) was added to a suspension of the resin in DMF (4 mL) and DCM (8 mL) followed by HOAt (84 mg, 0.6 mmol) and DIC (94 µL, 0.6 mmol). The syringe was agitated on an orbital table for 16 h. The resin was washed with DMF (3×20 mL) and dichloromethane (5×10 mL). The resin was dried under vacuum.

The cleavage of the peptide from the resin was performed using a solution Phenol (1 g), water (1 mL) and TIPS (0.5 mL) in TFA (QSP 20 mL) for 2 hours at room temperature. The resin was filtered off, the solution was then transferred to a 250 mL round bottom flask, the suspension was washed with 2×10 mL TFA.

The mixture was partially concentrated under vacuum at T<30° C. and the peptide was precipitated by the addition of 100 mL cold diethyl ether. The solid was collected by centrifugation (1000 rpm) and washed three times with cold diethyl ether. After drying under vacuum 300 mg of crude peptide were obtained Purification was performed using purification system B and the fractions containing pure desired peptide were lyophilized. The peptide as trifluoro acetate salt was obtained as a white solid.

m=38 mg (4%)

UPLC/MS:

RT: 2.79 min. (Analytical condition G), purity 97% (UV)

Observed mass m/z (ion type): 1229.5 (M+3H); 922.0 (M+4H); 737.9 (M+5H).

2.C. Synthesis of Peptide Having the SEQ ID NO: 63

In a 50 mL syringe equipped with a filter 500 mg of Rink Amide AM LL resin (NovaBiochem cat #8.55 120), 0.2 mmol of active Fmoc amino function were swelled in 20 mL DMF mixture for 30 min.

The solvent was filtered off and replaced by 12 mL of 20% v/v of piperidine in DMF. The syringe was agitated on an orbital table for 20 min. This deprotection procedure was repeated a second time and the resin was washed with DMF (2×10 mL) and dichloromethane (3×10 mL).

The resin was then suspended in 12 mL NMP and Fmoc-L-Lys(ivDDE)-OH) (344 mg, 0.6 mmol) was added as a solid followed by HOAt (82 mg, 0.6 mmol) and N,N'-Diisopropylcarbodiimide (DIC) (188 µL, 1.2 mmol). The syringe was agitated on an orbital table for 4 h and the acylation controlled by Kaiser Test. The resin was washed with DMF (2×10 mL) and dichloromethane (10 mL). Afterwards, the resin was transferred into the CEM Liberty Blue microwave peptide synthesizer.

Peptide synthesis was performed by using DIC 0.5M/ Oxyma 1M in DMF. All amino acids were introduced with double couplings at 90° C. for 2 minutes, with the exception of Aminoisobutyrric acid for which a triple coupling at 90° for 2 minutes was performed. At the end of the synthesis, the resin-peptide was transferred into a 50 mL polypropylene syringe and the peptide was acetylated at N-terminus with of Acetic Anhydride (472 µL, mmol) in DMF (10 mL) for 20 minutes, repeating the cycle twice.

Then, the ivDDE protecting group on C-terminus lysine side chain was removed by percolating 100 mL of a solution of hydrazine 5% w/v in DMF, followed by DMF washes (5×20 mL). The reaction was monitored by Kaiser Test.

Three PEG2 spacer units were introduced by single coupling by performing three times the following procedure: To the resin 12 mL of NMP were added followed by 2-[2-[2-(9H-fluoren-9-ylmethoxy carbonylamino) ethoxy] ethoxy]acetic acid (Fmoc-PEG2-OH) (309 mg, 0.8 mmol), HOAt (112 mg, 0.8 mmol) and DIC (250 µL, 1.6 mmol). The syringe was agitated on an orbital table for 2 h. The reaction was monitored by Kaiser Test. When needed, a double coupling was performed. The resin was washed with DMF (2×20 mL) and dichloromethane (3×10 mL). Then to the resin, 12 mL of 20% v/v of piperidine in DMF was added. The syringe was agitated on an orbital table for 20 min. This deprotection procedure was repeated a second time and the resin was washed with DMF (2×20 mL) and dichloromethane (3×10 mL).

The three gamma-glutamic acids spacers were introduced by performing a double coupling of each Fmoc-Glu-OtBu. Thus the following procedure was applied three times:

To the resin 12 mL of NMP were added followed by (4S)-5-tert-butoxy-4-(9H-fluoren-9-ylmethoxycarbonylamino)-5-oxo-pentanoic acid (Fmoc-Glu-OtBu) (283 mg mg, 0.8 mmol), HOAt (112 mg, 0.8 mmol) and DIC (250 µL, 1.6 mmol). The syringe was agitated on an orbital table for 2 h. The resin was washed with DMF (2×20 mL) and the coupling was repeated a second time. The reaction was monitored by Kaiser Test. When needed, a triple coupling was performed. The resin was washed with DMF (2×20 mL) and dichloromethane (3×10 mL). Then to the resin, 12 mL of 20% v/v of piperidine in DMF was added. The syringe was agitated on an orbital table for 20 min. This deprotection procedure was repeated a second time and the resin was washed with DMF (2×20 mL) and dichloromethane (3×10 mL).

Finally, the peptide was acylated with palmitic acid (256 mg, 1 mmol), HOAt (136 mg, 1 mmol) and DIC (252 mg, 2 mmol) activation in NMP (15 mL) for 2.5 h. The resin was washed with DMF (2×20 mL) and dichloromethane (3×10 mL) and dried under vacuum.

The cleavage of the peptide from the resin was performed using a solution Phenol (1.25 g), water (1.25 mL) and TIPS (0.75 mL) in TFA (QSP 25 mL) for 2.5 hours at room temperature. The resin was filtered off, and washed with 2×20 mL TFA. The combined filtrates were transferred to a 250 mL round bottom flask and partially concentrated under vacuum at T<30° C. and the peptide was precipitated by the addition of 100 mL ice-cold MTBE and centrifuged at 3600 rpm for 30 minutes.

The centrifuged pellet was then washed with ice-cold diethyl ether and centrifuged. This process was repeated three times. 600 mg of crude peptide are obtained. The crude peptide was dissolved (2 mg/mL) in a solution of $H_2O$/$CH_3CN$ (50:50 v/v) containing 0.1% formic acid and the mixture was gently stirred at 37° for 1 h, partially concentrated and lyophilized.

Purification was performed using purification system A and the fractions containing pure desired peptide were lyophilized. The peptide as trifluoroacetate salt was obtained as a white solid.

m=144 mg (20%)
UPLC/MS:
RT: 3.19 min. (Analytical condition E), purity 93% (UV)
Observed mass m/z (ion type): 1347.6 (M+3H); 1011.2 (M+4H); 809.2 (M+5H).

2.D. Synthesis of Peptide Having the ID NO: 81

In a 50 mL syringe equipped with a filter 500 mg of Rink Amide AM LL resin (NovaBiochem cat #8.55 120), 0.2 mmol of active Fmoc amino function were swelled in 20 mL DMF mixture for 30 min.

The solvent was filtered off and replaced by 12 mL of 20% v/v of piperidine in DMF. The syringe was agitated on an orbital table for 20 min. This deprotection procedure was repeated a second time and the resin was washed with DMF (2×10 mL) and dichloromethane (3×10 mL).

The resin was then suspended in 12 mL NMP and Fmoc-L-Lys(ivDDE)-OH) (344 mg, 0.6 mmol) was added as a solid followed by HOAt (82 mg, 0.6 mmol) and N,N'-diisopropylcarbodiimide (DIC) (188 µL, 1.2 mmol). The syringe was agitated on an orbital table for 4 h and the acylation controlled by Kaiser Test. The resin was washed with DMF (2×10 mL) and dichloromethane (10 mL). Afterwards, the resin was transferred into the CEM Liberty Blue microwave peptide synthesizer.

Peptide synthesis was performed by using DIC 0.5M/Oxyma 1M in DMF. All amino acids were introduced with double couplings at 90° C. for 2 minutes, with the exception of aminoisobutyrric acid for which a triple coupling at 90° for 2 minutes was performed. At the end of the synthesis, the resin-peptide was transferred into a 50 mL polypropylene syringe and the peptide was acetylated at N-terminus with of acetic anhydride (472 µL, 5 mmol) in DMF (10 mL) for 20 minutes, repeating the cycle twice.

Then, the ivDDE protecting group on C-terminus lysine side chain was removed by percolating 100 mL of a solution of hydrazine 5% w/v in DMF, followed by DMF washes (5×20 mL). The reaction was monitored by Kaiser Test.

Three PEG2 spacer units were introduced by single coupling by performing three times the following procedure: To the resin 12 mL of NMP are added followed by 2-[2-[2-(9H-fluoren-9-ylmethoxy carbonylamino) ethoxy] ethoxy] acetic acid (Fmoc-PEG2-OH) (309 mg, 0.8 mmol), HOAt (112 mg, 0.8 mmol) and DIC (250 µL, 1.6 mmol). The syringe was agitated on an orbital table for 2 h. The reaction was monitored by Kaiser Test. When needed, a double coupling was performed. The resin was washed with DMF (2×20 mL) and dichloromethane (3×10 mL). Then to the resin, 12 mL of 20% v/v of piperidine in DMF was added. The syringe was agitated on an orbital table for 20 min. This deprotection procedure was repeated a second time and the resin was washed with DMF (2×20 mL) and dichloromethane (3×10 mL).

The three gamma-glutamic acids spacers were introduced by performing a double coupling of each Fmoc-Glu-OtBu. Thus the following procedure was applied three times:

To the resin 12 mL of NMP were added followed by (4S)-5-tert-butoxy-4-(9H-fluoren-9-ylmethoxycarbonylamino)-5-oxo-pentanoic acid (Fmoc-Glu-OtBu) (283 mg, 0.8 mmol), HOAt (112 mg, 0.8 mmol) and DIC (250 µL, 1.6 mmol). The syringe was agitated on an orbital table for 2 h. The resin was washed with DMF (2×20 mL) and the coupling was repeated a second time. The reaction was monitored by Kaiser Test. When needed, a triple coupling was performed. The resin was washed with DMF (2×20 mL) and dichloromethane (3×10 mL). Then to the resin, 12 mL of 20% v/v of piperidine in DMF was added. The syringe was agitated on an orbital table for 20 min. This deprotection procedure was repeated a second time and the resin was washed with DMF (2×20 mL) and dichloromethane (3×10 mL).

Finally, the peptide was acylated with stearic acid (284 mg, 1 mmol), HOAt (136 mg, 1 mmol) and DIC (252 mg, 2 mmol) activation in NMP (15 mL) for 2.5 h. The resin was washed with DMF (2×20 mL) and dichloromethane (3×10 mL) and dried under vacuum.

The cleavage of the peptide from the resin was performed using a solution phenol (1.25 g), water (1.25 mL) and TIPS (0.75 mL) in TFA (QSP 25 mL) for 2.5 hours at room temperature. The resin was filtered off, and washed with 2×20 mL TFA. The compbined filtrates were transferred to a 250 mL round bottom flask and partially concentrated under vacuum at T<30° C. and the peptide was precipitated by the addition of 100 mL ice-cold MTBE and centrifuged at 3600 rpm for 30 minutes.

The centrifuged pellet was then washed with ice-cold diethyl ether and centrifuged. This process was repeated three times. 600 mg of crude peptide were obtained. The crude peptide was dissolved (2 mg/mL) in a solution of $H_2O$/$CH_3CN$ (50:50 v/v) containing 0.1% formic acid and the mixture was gently stirred at 37° for 1 h, partially concentrated and lyophilized.

Purification was performed using purification system A and the fractions containing pure desired peptide were lyophilized. The peptide as trifluoroacetate salt was obtained as a white solid.m=185 mg (20%)
UPLC/MS:
RT: 4.5 min. (Analytical condition E), purity 93% (UV)

Observed mass m/z (ion type): 1357.4 (M+3H); 1018.7 (M+4H); 815.2 (M+5H).

2.E. Synthesis of Peptide Having the SEQ ID NO: 150

In a 50 mL syringe equipped with a filter 500 mg of Rink Amide AM LL resin (NovaBiochem cat #8.55 120), 0.2 mmol of active Fmoc amino function were swelled in 20 mL DMF mixture for 30 min.

The solvent was filtered off and replaced by 12 mL of 20% v/v of piperidine in DMF. The syringe was agitated on an orbital table for 20 min. This deprotection procedure was repeated a second time and the resin was washed with DMF (2×10 mL) and dichloromethane (3×10 mL).

The resin was then suspended in 12 mL NMP and Fmoc-L-Lys(ivDDE)-OH) (344 mg, 0.6 mmol) was added as a solid followed by HOAt (82 mg, 0.6 mmol) and N,N'-Diisopropylcarbodiimide (DIC) (188 µL, 1.2 mmol). The syringe was agitated on an orbital table for 4 h and the acylation controlled by Kaiser Test. The resin was washed with DMF (2×10 mL) and dichloromethane (10 mL). Afterwards, the resin was transferred into the CEM Liberty Blue microwave peptide synthesizer.

Peptide synthesis was performed by using DIC 0.5M/ Oxyma 1M in DMF. All amino acids were introduced with double couplings at 90° C. for 2 minutes, with the exception of aminoisobutyrric acid for which a triple coupling at 90° for 2 minutes was performed. Four $Peg_2$ units where introduced in the main peptide chain using Fmoc-$Peg_2$-OH as any amino acid using the some coupling deprotection cycles.

At the end of the synthesis, the resin-peptide was transferred into a 50 mL polypropylene syringe and the peptide was acetylated at N-terminus with of acetic anhydride (472 µL, 5 mmol) in DMF (10 mL) for 20 minutes, repeating the cycle twice.

Then, the ivDDE protecting group on C-terminus lysine side chain was removed by percolating 100 mL of a solution of hydrazine 5% w/v in DMF, followed by DMF washes (5×20 mL). The reaction was monitored by Kaiser Test.

The four gamma-glutamic acids spacers were introduced by performing a double coupling of each Fmoc-Glu-OtBu. Thus the following procedure was applied four times:

To the resin 12 mL of NMP were added followed by (4S)-5-tert-butoxy-4-(9H-fluoren-9-ylmethoxycarbonylamino)-5-oxo-pentanoic acid (Fmoc-Glu-OtBu) (283 mg, 0.8 mmol), HOAt (112 mg, 0.8 mmol) and DIC (250 µL, 1.6 mmol). The syringe was agitated on an orbital table for 2 h. The resin was washed with DMF (2×20 mL) and the coupling was repeated a second time. The reaction was monitored by Kaiser Test. When needed, a triple coupling was performed. The resin was washed with DMF (2×20 mL) and dichloromethane (3×10 mL). Then to the resin, 12 mL of 20% v/v of piperidine in DMF was added. The syringe was agitated on an orbital table for 20 min. This deprotection procedure was repeated a second time and the resin was washed with DMF (2×20 mL) and dichloromethane (3×10 mL).

Finally, the peptide was acylated with palmytic acid (254 mg, 1 mmol), HOAt (136 mg, 1 mmol) and DIC (252 mg, 2 mmol) activation in NMP (15 mL) for 2.5 h. The resin was washed with DMF (2×20 mL) and dichloromethane (3×10 mL) and dried under vacuum.

The cleavage of the peptide from the resin was performed using a solution phenol (1.25 g), water (1.25 mL) and TIPS (0.75 mL) in TFA (QSP 25 mL) for 2.5 hours at room temperature. The resin was filtered off, and washed with 2×20 mL TFA. The combined filtrates were transferred to a 250 mL round bottom flask and partially concentrated under vacuum at T<30° C. and the peptide was precipitated by the addition of 100 mL ice-cold MTBE and centrifuged at 3600 rpm for 30 minutes.

The centrifuged pellet was then washed with ice-cold diethyl ether and centrifuged. This process was repeated three times. 600 mg of crude peptide were obtained. The crude peptide was dissolved (2 mg/mL) in a solution of $H_2O/CH_3CN$ (50:50 v/v) containing 0.1% formic acid and the mixture was gently stirred at 37° for 1 h, partially concentrated and lyophilized.

Purification was performed using purification system A and the fractions containing pure desired peptide were lyophilized. The peptide as trifluoroacetate salt was obtained as a white solid.

m=135 mg (14%)

UPLC/MS:

RT: 3.1 min. (Analytical condition G), purity 98% (UV)

Observed mass m/z (ion type): 1426.4 (M+3H); 1070.0 (M+4H); 856.3 (M+5H).

2.F. Synthesis of Peptide Having the SEQ ID NO: 170

In a 50 mL syringe equipped with a filter 500 mg of Rink Amide AM LL resin (NovaBiochem cat #8.55 120), 0.2 mmol of active Fmoc amino function were swelled in 20 mL DMF mixture for 30 min.

The solvent was filtered off and replaced by 12 mL of 20% v/v of piperidine in DMF. The syringe was agitated on an orbital table for 20 min. This deprotection procedure was repeated a second time and the resin was washed with DMF (2×10 mL) and dichloromethane (3×10 mL).

The resin was then suspended in 12 mL NMP and Fmoc-L-Lys(ivDDE)-OH) (344 mg, 0.6 mmol) was added as a solid followed by HOAt (82 mg, 0.6 mmol) and N,N'-Diisopropylcarbodiimide (DIC) (188 µL, 1.2 mmol). The syringe was agitated on an orbital table for 4 h and the acylation controlled by Kaiser Test. The resin was washed with DMF (2×10 mL) and dichloromethane (10 mL). Afterwards, the resin was transferred into the CEM Liberty Blue microwave peptide synthesizer.

Peptide synthesis was performed by using DIC 0.5M/ Oxyma 1M in DMF. All amino acids were introduced with double couplings at 90° C. for 2 minutes, with the exception of Aminoisobutyrric acid for which a triple coupling at 90° for 2 minutes was performed. Four $Peg_2$ units were introduced in the main peptide chain using Fmoc-$Peg_2$-0H as any amino acid using the some coupling deprotection cycles.

At the end of the synthesis, the resin-peptide was transferred into a 50 mL polypropylene syringe and the peptide was acetylated at N-terminus with of acetic anhydride (472 µL, 5 mmol) in DMF (10 mL) for 20 minutes, repeating the cycle twice.

Then, the ivDDE protecting group on C-terminus Lysine side chain was removed by percolating 100 mL of a solution of hydrazine 5% w/v in DMF, followed by DMF washes (5×20 mL). The reaction was monitored by Kaiser Test.

The four gamma-glutamic acids spacers were introduced by performing a double coupling of each Fmoc-Glu-OtBu. Thus the following procedure was applied four times:

To the resin 12 mL of NMP were added followed by (4S)-5-tert-butoxy-4-(9H-fluoren-9-ylmethoxycarbonylamino)-5-oxo-pentanoic acid (Fmoc-Glu-OtBu) (283 mg, 0.8 mmol), HOAt (112 mg, 0.8 mmol) and DIC (250 µL, 1.6 mmol). The syringe was agitated on an orbital table for 2 h. The resin was washed with DMF (2×20 mL) and the coupling was repeated a second time. The reaction was monitored by Kaiser Test. When needed, a triple coupling was performed. The resin was washed with DMF (2×20 mL) and dichloromethane (3×10 mL). Then to the resin, 12 mL of 20% v/v of piperidine in DMF was added. The syringe was agitated on an orbital table for 20 min. This deprotection procedure was repeated a second time and the resin was washed with DMF (2×20 mL) and dichloromethane (3×10 mL).

Finally, the peptide was acylated with palmytic acid (254 mg, 1 mmol), HOAt (136 mg, 1 mmol) and DIC (252 mg, 2 mmol) activation in NMP (15 mL) for 2.5 h. The resin was washed with DMF (2×20 mL) and dichloromethane (3×10 mL) and dried under vacuum.

The cleavage of the peptide from the resin was performed using a solution phenol (1.25 g), water (1.25 mL) and TIPS (0.75 mL) in TFA (QSP 25 mL) for 2.5 hours at room temperature. The resin was filtered off, and washed with 2×20 mL TFA. The combined filtrates were transferred to a 250 mL round bottom flask and partially concentrated under vacuum at T<30° C. and the peptide was precipitated by the addition of 100 mL ice-cold MTBE and centrifuged at 3600 rpm for 30 minutes.

The centrifuged pellet was then washed with ice-cold diethyl ether and centrifuged. This process was repeated three times. 600 mg of crude peptide were obtained. The crude peptide was dissolved (2 mg/mL) in a solution of $H_2O/CH_3CN$ (50:50 v/v) containing 0.1% formic acid and the mixture was gently stirred at 37° for 1 h, partially concentrated and lyophilized.

Purification was performed using purification system A and the fractions containing pure desired peptide are lyophilized. The peptide as trifluoroacetate salt was obtained as a white solid.

m=140 mg (16%)

UPLC/MS:

RT: 3.53 min. (Analytical condition L), purity 98% (UV)

Observed mass m/z (ion type): 1431.8 (M+3H); 1073.9 (M+4H); 859.3 (M+5H).

2.G. Results

The results obtained with all the peptides of the invention of SEQ ID NO: 1-193 are indicated in the following Table 1.

TABLE 1

| SEQ ID NO | UPLC Ret. Time Min. (Conditions) | Observed mass Ion type | | | | Mono isotopic mass |
|---|---|---|---|---|---|---|
| | | M + 5H | M + 4H | M + 3H | M + 2H | |
| 1 | 2.80 (A) | 552.8 | 690.6 | 920.4 | | 2758.5 |
| 2 | 3.00 (A) | 553.1 | 691.1 | 921.4 | | 2760.5 |
| 3 | 3.8 (C) | | 738.6 | 984.4 | 1475.9 | 2947.7 |
| 4 | 4.22 (D) | | 785.1 | 1046.4 | 1569.3 | 3133.8 |
| 5 | 3.64 (E) | | 792.0 | 1055.4 | 1583.1 | 3161.8 |
| 6 | 3.31 (F) | | 789.8 | 1062.5 | 1578.4 | 3152.7 |
| 7 | 3.97 (D) | 683.5 | 854.0 | 1138.2 | 1706.7 | 3409.8 |
| 8 | 3.2 (E) | 679.9 | 849.2 | 1132.2 | 1697.9 | 3391.9 |
| 9 | 3.28 (G) | 685.4 | 856.7 | 1141.5 | 1712.3 | 3419.9 |
| 10 | 2.79 (G) | 708.9 | 885.8 | 1181.0 | 1770.9 | 3537.0 |
| 11 | 3.27 (E) | 737.8 | 922.2 | 1229.1 | | 3682.1 |
| 12 | 2.9 (F) | 737.9 | 921.8 | 1228.9 | | 3682.1 |
| 13 | 4.07 (D) | 766.5 | 968.6 | 1277.8 | | 3827.1 |
| 14 | 3.48 (G) | 814.9 | 1019.5 | 1357.9 | | 4067.3 |
| 15 | 3.18 (G) | 861.3 | 1076.3 | 1434.9 | | 4299.4 |
| 16 | 3.27 (E) | 852.1 | 1064.8 | 1419.5 | | 4253.4 |
| 17 | 3.68 (D) | 846.7 | 1059.0 | 1410.1 | | 4225.4 |
| 18 | 4.56 (A) | 791.4 | 988.5 | 1317.7 | | 3950.2 |
| 19 | 5.18 (A) | 855.0 | 1068.6 | 1423.8 | | 4268.4 |
| 20 | 5.19 (A) | 918.3 | 1147.8 | 1530.1 | | 4586.6 |
| 21 | 4.23 (A) | 762.2 | 952.1 | 1269.8 | | 3802.2 |
| 22 | 3.68 (E) | 779.3 | 974.0 | 1298.4 | | 3889.3 |
| 23 | 4.05 (D) | 803.5 | 1003.9 | 1338.4 | | 4009.2 |
| 24 | 3.1 (G) | 799.7 | 999.8 | 1332.7 | | 3991.2 |
| 25 | 3.22 (E) | 811.9 | 1014.9 | 1352.6 | | 4051.2 |

TABLE 1-continued

| SEQ ID NO | UPLC Ret. Time Min. (Conditions) | Observed mass Ion type | | | | Mono isotopic mass |
|---|---|---|---|---|---|---|
| | | M + 5H | M + 4H | M + 3H | M + 2H | |
| 26 | 3.28 (E) | 842.2 | 1052.3 | 1402.8 | | 4203.4 |
| 27 | 3.18 (F) | 845.4 | 1056.3 | 1407.9 | | 4217.4 |
| 28 | 3.13 (G) | 836.9 | 1045.8 | 1392.7 | | 4175.3 |
| 29 | 3.39 (G) | 810.6 | 1012.8 | 1350.3 | | 4044.3 |
| 30 | 3.66 (E) | 805.4 | 1006.4 | 1341.6 | | 4019.3 |
| 31 | 3.39 (H) | 831.2 | 1038.7 | 1383.9 | | 4147.3 |
| 32 | 4.55 (D) | 839.4 | 1048.5 | 1397.9 | | 4189.4 |
| 33 | 3.68 (E) | 848.0 | 1059.4 | 1412.2 | | 4231.4 |
| 34 | 3.55 (E) | 814.1 | 1016.9 | 1355.9 | | 4061.3 |
| 35 | 3.55 (E) | 817.2 | 1021.0 | 1361.2 | | 4079.3 |
| 36 | 2.61 (I) | 850.9 | 1063.3 | 1417.3 | | 4245.4 |
| 37 | 2.73 (I) | 852.3 | 1066.1 | 1421.2 | | 4256.4 |
| 38 | 3.28 (G) | 808.3 | 1010.3 | 1346.4 | | 4033.3 |
| 39 | 3.54 (G) | 884.9 | 1105.9 | 1474.3 | | 4417.5 |
| 40 | 3.24 (G) | 887.6 | 1109.1 | 1479.6 | | 4431.5 |
| 41 | 3.62 (E) | 850.5 | 1063.2 | 1717.4 | | 4245.4 |
| 42 | 3.40 (G) | 885.1 | 1106.0 | 1473.9 | | 4417.5 |
| 43 | 2.83 (F) | 879.3 | 1099.0 | 1464.8 | | 4389.5 |
| 44 | 4.79 (A) | 807.6 | 1009.3 | 1345.1 | | 4031.3 |
| 45 | 3.83 (C) | 816.3 | 1019.9 | 1359.8 | | 4072.3 |
| 46 | 5.25 (A) | 843.2 | 1053.1 | 1404.0 | | 4208.4 |
| 47 | 3.4 (E) | 909.2 | 1136.3 | 1514.5 | | 4537.5 |
| 48 | 3.69 (E) | 980.7 | 1225.5 | 1633.4 | | 4893.8 |
| 49 | 3.7 (E) | 989.0 | 1236.1 | 1647.6 | | 4935.8 |
| 50 | 3.49 (E) | | 788.7 | 1051.4 | 1577.3 | 3149.8 |
| 51 | 4.94 (D) | 700.2 | 874.6 | 1166.3 | 1748.4 | 3493.1 |
| 52 | 3.94 (F) | 728.7 | 910.8 | 1214.3 | | 3638.1 |
| 53 | 3.37 (E) | | 821.2 | 1094.1 | 1641.1 | 3278.9 |
| 54 | 3.15 (C) | 697.6 | 871.8 | 1161.8 | 1742.2 | 3480.0 |
| 55 | 3.11 (E) | | 885.5 | 1180.5 | 1770.3 | 3537.0 |
| 56 | 3.79 (G) | | 864.5 | 1152.5 | 1728.7 | 3452.0 |
| 57 | 3.05 (J) | 726.4 | 907.8 | 1209.8 | | 3625.0 |
| 58 | 2.79 (G) | 737.9 | 922.0 | 1229.5 | | 3682.1 |
| 59 | 3.0 (G) | 746.0 | 932.5 | 1243.0 | | 3724.1 |
| 60 | 3.76 (D) | 771.9 | 964.7 | 1285.8 | | 3852.2 |
| 61 | 3.58 (D) | 783.3 | 979.0 | 1304.8 | | 3909.2 |
| 62 | 4.01 (D) | 780.0 | 975.3 | 1299.8 | | 3894.2 |
| 63 | 3.19 (E) | 809.2 | 1011.2 | 1347.6 | | 4039.2 |
| 64 | 3.19 (E) | 838.5 | 1047.2 | 1396.7 | | 4184.3 |
| 65 | 2.68 (F) | 846.8 | 1057.6 | 1410.1 | | 4225.3 |
| 66 | 3.78 (G) | 847.9 | 1059.8 | 1412.6 | | 4231.4 |
| 67 | 3.57 (D) | 742.6 | 929.0 | 1237.6 | | 3710.1 |
| 68 | 4.91 (A) | 771.9 | 964.6 | 1285.6 | | 3853.1 |
| 69 | 4.99 (A) | 800.9 | 1000.7 | 1333.9 | | 3997.2 |
| 70 | 4.92 (A) | 801.1 | 1001.1 | 1333.9 | 2001.4 | 3999.2 |
| 71 | 3.37 (G) | 769.3 | 961.2 | 1281.2 | | 3838.2 |
| 72 | 4.59 (D) | 786.1 | 982.3 | 1309.2 | | 3922.2 |
| 73 | 3.48 (G) | 752.0 | 939.8 | 1252.2 | | 3752.1 |
| 74 | 3.46 (G) | 772.8 | 965.6 | 1286.8 | | 3855.1 |
| 75 | 3.32 (H) | 798.4 | 997.6 | 1329.8 | | 3983.2 |
| 76 | 4.92 (A) | 800.5 | 1000.3 | 1333.7 | | 3997.2 |
| 77 | 7.29 (B) | 806.6 | 1007.3 | 1342.7 | 2014.6 | 4025.3 |
| 78 | 4.83 (A) | 810.1 | 1012.1 | 1349.1 | | 4044.3 |
| 79 | 3.57 (E) | 783.3 | 978.8 | 1304.7 | | 3908.2 |
| 80 | 3.72 (G) | 786.3 | 982.4 | 1309.7 | | 3922.2 |
| 81 | 4.5 (E) | 815.2 | 1018.7 | 1357.4 | | 4067.3 |
| 82 | 3.23 (K) | 852.3 | 1065.0 | 1419.5 | | 4253.4 |
| 83 | 3.56 (F) | 780.2 | 975.5 | 1300.6 | | 3897.2 |
| 84 | 3.78 (G) | 817.5 | 1021.2 | 1361.6 | | 4078.3 |
| 85 | 3.81 (G) | 820.4 | 1025.1 | 1366.4 | | 4092.3 |
| 86 | 3.85 (G) | 803.5 | 1004.5 | 1338.8 | | 4010.3 |
| 87 | 3.97 (G) | 805.4 | 1006.4 | 1342.4 | | 4021.3 |
| 88 | 3.32 (G) | 824.3 | 1030.1 | 1373.1 | | 4112.3 |
| 89 | 3.16 (F) | 832.5 | 1040.4 | 1386.7 | | 4154.3 |
| 90 | 4.5 (D) | 844.1 | 1055.1 | 1406.1 | | 4212.3 |
| 91 | 3.22 (G) | 861.4 | 1076.3 | 1434.7 | | 4299.4 |
| 92 | 4.93 (A) | 826.6 | 1033.3 | 1377.4 | | 4128.3 |
| 93 | 4.93 (A) | 855.6 | 1069.6 | 1425.8 | | 4273.4 |
| 94 | 5.14 (A) | 791.3 | 988.8 | 1317.6 | | 3950.2 |
| 95 | 5.14 (A) | 854.6 | 1068.3 | 1424.1 | | 4268.4 |
| 96 | 5.19 (A) | 918.3 | 1148.7 | 1531.1 | | 4586.6 |
| 97 | 3.52 (E) | 830.9 | 1038.4 | 1384.4 | | 4147.4 |
| 98 | 3.47 (E) | 798.0 | 997.2 | 1329.4 | | 3983.2 |
| 99 | 3.35 (G) | 798.5 | 997.4 | 1329.9 | | 3983.2 |
| 100 | 3.51 (G) | 773.0 | 965.5 | 1287.0 | | 3855.1 |

TABLE 1-continued

| SEQ ID NO | UPLC Ret. Time Min. (Conditions) | Observed mass Ion type M + 5H | M + 4H | M + 3H | M + 2H | Mono isotopic mass |
|---|---|---|---|---|---|---|
| 101 | 3.58 (G) | 814.6 | 1018.8 | 1357.5 | | 4067.3 |
| 102 | 3.26 (G) | 833.1 | 1040.4 | 1386.7 | | 4154.3 |
| 103 | 3.41 (G) | 834.5 | 1042.5 | 1390.0 | | 4165.3 |
| 104 | 3.56 (G) | 743.6 | 929.2 | 1238.6 | | 3710.1 |
| 105 | 3.35 (G) | 769.3 | 961.1 | 1281.5 | | 3838.2 |
| 106 | 5.01 (A) | 797.9 | 996.8 | 1329.1 | 1993.9 | 3983.2 |
| 107 | 4.56 (A) | 843.7 | 1054.2 | 1405.3 | | 4212.4 |
| 108 | 4.56 (A) | 873.0 | 1090.5 | 1453.7 | | 4357.4 |
| 109 | 4.56 (A) | 817.9 | 1021.9 | 1362.3 | 2043.9 | 4083.3 |
| 110 | 4.70 (A) | 818.1 | 1022.2 | 1362.6 | | 4084.3 |
| 111 | 5.08 (A) | 860.8 | 1076.1 | 1434.1 | | 4298.4 |
| 112 | 3.77 (C) | 806.9 | 1008.5 | 1344.3 | | 4028.3 |
| 113 | 5.27 (A) | 818.8 | 1022.0 | 1362.4 | | 4082.3 |
| 114 | 4.97 (A) | 809.2 | 1011.0 | 1347.4 | | 4039.3 |
| 115 | 5.06 (A) | 835.0 | 1043.7 | 1391.0 | | 4169.3 |
| 116 | 4.99 (A) | 838.2 | 1047.5 | 1396.4 | | 4184.4 |
| 117 | 4.80 (A) | 809.2 | 1011.0 | 1347.7 | 2021.5 | 4039.3 |
| 118 | 4.79 (A) | 771.8 | 964.0 | 1285.0 | 1927.5 | 3852.2 |
| 119 | 4.78 (A) | 800.8 | 1000.5 | 1333.9 | 1999.7 | 3997.2 |
| 120 | 4.18 (A) | 797.9 | 996.7 | 1328.9 | 1993.4 | 3983.2 |
| 121 | 4.41 (A) | 829.5 | 1037.2 | 1382.7 | 2073.0 | 4142.3 |
| 122 | 5.2 (A) | 887.0 | 1108.3 | 1477.4 | | 4428.5 |
| 123 | 5.17 (A) | 776.9 | 971.2 | 1294.6 | 1941.5 | 3879.2 |
| 124 | 5.19 (A) | 826.6 | 1032.8 | 1377.0 | 2065.3 | 4126.4 |
| 125 | 4.20 (D) | 849.4 | 1060.9 | 1414.3 | | 4239.4 |
| 126 | 4.36 (C) | 803.3 | 1004.0 | 1338.5 | | 4011.3 |
| 127 | 2.54 (I) | 795.0 | 993.0 | 1323.7 | | 3968.3 |
| 128 | 3.77 (C) | 840.7 | 1050. | 1400.2 | | 4196.4 |
| 129 | 3.40 (F) | 826.7 | 1032.9 | 1376.8 | | 4125.4 |
| 130 | 3.57 (D) | 875.5 | 1094.3 | 1458.7 | | 4370.5 |
| 131 | 3.72 (D) | 875.6 | 1094.0 | 1458.1 | | 4370.5 |
| 132 | 3.68 (F) | 844.17 | 1054.6 | 1406.3 | | 4213.4 |
| 133 | 3.76 (C) | 817.5 | 1021.8 | 1362.2 | | 4081.3 |
| 134 | 3.92 (C) | 823.2 | 1028.6 | 1370.9 | | 4110.4 |
| 135 | 3.34 (F) | 844.2 | 1054.6 | 1405.9 | | 4212.4 |
| 136 | 3.67 (D) | 875.6 | 1094.2 | 1458.4 | | 4370.5 |
| 137 | 3.84 (F) | 826.2 | 1032.6 | 1376.4 | | 4124.4 |
| 138 | 3.54 (F) | 863.3 | 1078.9 | 1438.3 | | 4310.5 |
| 139 | 3.11 (G) | 838.5 | 1049.1 | 1398.3 | | 4189.3 |
| 140 | 3.6 (D) | 867.8 | 1084.6 | 1445.6 | | 4331.5 |
| 141 | 2.68 (F) | 886.7 | 1108.3 | 1477.3 | | 4427.5 |
| 142 | 3.81 (D) | 872.5 | 1090.5 | 1453.8 | | 4355.5 |
| 143 | 3.76 (E) | 867.4 | 1083.9 | 1445.1 | | 4331.5 |
| 144 | 4.03 (D) | 830.1 | 1037.8 | 1383.0 | | 4145.4 |
| 145 | 4.71 (A) | 867.6 | 1084.3 | 1445.6 | 2167.7 | 4331.5 |
| 146 | 2.84 (C) | 872.6 | 1090.4 | 1453.8 | | 4355.5 |
| 147 | 3.76 (D) | 856.3 | 1070.15 | 1426.5 | | 4274.4 |
| 148 | 3.62 (C) | 817.7 | 1027.8 | 1362.3 | | 4081.3 |
| 149 | 2.99 (C) | 856.4 | 1069.7 | 1426.7 | | 4274.4 |
| 150 | 3.10 (G) | 856.3 | 1070.0 | 1426.4 | | 4274.4 |
| 151 | 3.01 (G) | 859.3 | 1073.6 | 1430.6 | | 4288.4 |
| 152 | 3.07 (G) | 870.6 | 1087.9 | 1450.4 | | 4345.5 |
| 153 | 3.97 (L) | 830.3 | 1037.9 | 1383.3 | | 4145.4 |
| 154 | 4.12 (L) | 830.4 | 1037.7 | 1383.5 | | 4145.4 |
| 155 | 4.03 (G) | 786.8 | 982.8 | 1310.1 | | 3925.2 |
| 156 | 3.96 (C) | 848.6 | 1060.6 | 1413.8 | | 4236.5 |
| 157 | 3.09 (C) | 860.9 | 1075.9 | 1434.1 | | 4298.5 |
| 158 | 3.59 (C) | 817.9 | 1022.3 | 1362.6 | | 4083.3 |
| 159 | 3.71 (D) | 867.9 | 1084.5 | 1445.7 | | 4331.5 |
| 160 | 3.97 (L) | 856.0 | 1070.0 | 1426.6 | | 4274.4 |
| 161 | 3.69 (L) | 848.0 | 1059.5 | 1412.6 | | 4233.3 |
| 162 | 3.98 (L) | 861.0 | 1076.2 | 1434.4 | | 4298.5 |
| 163 | 2.47 (C) | 806.0 | 1007.1 | 1343.1 | | 4025.3 |
| 164 | 3.20 (C) | 811.7 | 1014.4 | 1352.3 | | 4053.3 |
| 165 | 3.06 (C) | 809.1 | 1011.4 | 1348.0 | | 4039.3 |
| 166 | 2.86 (F) | 843.4 | 1023.8 | 1404.7 | | 4208.4 |
| 167 | 3.69 (L) | 853.6 | 1066.6 | 1422.0 | | 4260.4 |
| 168 | 369 (L) | 853.6 | 1066.6 | 1421.5 | | 4260.4 |
| 169 | 4.03 (L) | 921.6 | 1151.9 | 1535.3 | | 4600.7 |
| 170 | 3.53 (L) | 859.3 | 1073.9 | 1431.8 | | 4289.4 |
| 171 | 5.89 (A) | 820.4 | 1025.2 | 1366.3 | 2049.5 | 4097.8 |
| 172 | 2.02 (C) | 850.5 | 1063.1 | 1416.9 | | 4246.4 |
| 173 | 6.33 (A) | 826.1 | 1032.3 | 1375.8 | 2063.7 | 4125.8 |
| 174 | 4.86 (A) | 814.8 | 1018.2 | 1357.7 | 2036.1 | 4068.3 |
| 175 | 5.15 (A) | 785.6 | 981.5 | 1309.3 | 1963.1 | 3922.3 |
| 176 | 5.06 (A) | 788.8 | 985.8 | 1314.0 | 1970.2 | 3937.2 |
| 177 | 4.77 (A) | 843.6 | 1354.5 | 1405.7 | 2108.5 | 4213.4 |
| 178 | 4.59 (A) | 803.6 | 1003.9 | 1338.3 | 2007.2 | 4011.3 |
| 179 | 4.76 (A) | | 1008.8 | 1345.4 | 2017.6 | 4031.3 |
| 180 | 4.95 (A) | 859.2 | 1074.0 | 1431.8 | 2147.6 | 4291.4 |
| 181 | 5.1 (A) | 806.6 | 1008.2 | 1344.0 | 2015.5 | 4027.3 |
| 182 | 3.27 (L) | 856.6 | 1070.4 | 1426.8 | | 4275.4 |
| 183 | 4.19 (L) | 895.8 | 1119.5 | 1492.5 | | 4471.6 |
| 184 | 3.47 (L) | 921.7 | 1151.9 | 1535.4 | | 4601.6 |
| 185 | 3.62 (L) | 859.2 | 1073.9 | 1431.5 | | 4289.4 |
| 186 | 3.25 (L) | 856.4 | 1070.1 | 1426.6 | | 4275.4 |
| 187 | 2.82 (F) | 896.0 | 1119.9 | 1492.5 | | 4471.6 |
| 188 | 2.57 (F) | 893.0 | 1116.5 | 1488.2 | | 4457.6 |
| 189 | 3.47 (L) | 895.6 | 1119.7 | 1492.6 | | 4472.6 |
| 190 | 2.84 (D) | 853.8 | 1167.0 | 1422.3 | | 4261.3 |
| 191 | 3.60 (L) | 859.4 | 1173.7 | 1431.5 | | 4289.4 |
| 192 | 2.76 (F) | 830.9 | 1038.2 | 1384.0 | | 4145.4 |
| 193 | 3.97 (L) | 921.6 | 1151.9 | 1535.5 | | 4600.7 |

Condition A is the following:
Column: Acquity Peptide CSH, C18, 130 Å, 2.1×100 mm, 1.7 um;
Column Temperature: 50° C.; Flow=0.6 ml/min;
Solvent A: 0.1% TFA in $H_2O$;
Solvent B: 0.1% TFA in $CH_3CN$;
Gradient: from 0 to 1 min B=2%, from 1 to 7 min B=2% to 70%, from 7 to 8 min B=70% to 100%;
UV detector: wavelength: 220 nm; MS acquisition: ESI+ 200 to 3000 uma.

Conditons B is the following:
Column: Acquity BEH C18, 130 Å, 2.1×50 mm, 1.7 μm
Column temperature 60° C.; Flow 0.6 ml/mn
Solvent A: 0.05% TFA in $H_2O$
Solvent B: 0.05% TFA in $CH_3CN$
Gradient: from 0 to 1 min B=2%, from 1 to 16 min B=2% to 100%, from 16 to 17 min B=100% UV detector: wavelength: 220 nm; MS acquisition: ESI+200 to 3000 uma Condition C is the following:
Column: ACQUITY BEH C4, 130 Å, 2.1×50 mm, 1.7 μm;
Column temperature 45° C.; Flow rate: 0.4 ml/min;
Solvent A: 0.1% TFA in $H_2O$;
Solvent B: 0.1% TFA in $CH_3CN$;
UV detector: wavelength: 214 nm; MS acquisition: ESI+ 200 to 3000 uma;
Elution system: from 0 to 1 min B=35%, from 1 to 5 min B=35% to 50%, from 5 to 6 min B=50% to 80%.

Condition D is the following:
Column: ACQUITY BEH C4, 130 Å, 2.1×50 mm, 1.7 μm;
Column temperature 45° C.; Flow rate: 0.4 ml/min;
Solvent A: 0.1% TFA in $H_2O$;
Solvent B: 0.1% TFA in $CH_3CN$;
UV detector: wavelength: 214 nm; MS acquisition: ESI+ 200 to 3000 uma;
Elution system: from 0 to 1 min B=30%, from 1 to 5 min B=30% to 50%, from 5 to 6 min B=50% to 90%

Condition E is the following:
Column: ACQUITY BEH C4, 130 Å, 2.1×50 mm, 1.7 μm;
Column temperature 45° C.; Flow rate: 0.4 ml/min;
Solvent A: 0.1% TFA in $H_2O$;
Solvent B: 0.1% TFA in $CH_3CN$;

UV detector: wavelength: 214 nm; MS acquisition: ESI+ 200 to 3000 uma;
Elution system: from 0 to 1 min B=30%, from 1 to 5 min B=30% to 70%, from 5 to 6 min B=70% to 90%.
Condition F is the following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+ 200 to 3000 uma;
Elution system: from 0 to 1 min B=35%, from 1 to 5 min B=35% to 55%, from 5 to 6 min B=55% to 90%.
Condition G is the following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+ 200 to 3000 uma;
Elution system: from 0 to 1 min B=35%, from 1 to 5 min B=35% to 55%, from 5 to 6 min B=55% to 80%.
Condition H is the following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+ 200 to 3000 uma;
Elution system: from 0 to 1 min B=35%, from 1 to 7 min B=35% to 55%, from 7 to 8 min B=55% to 90%.
Condition I is the following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+ 200 to 3000 uma;
Elution system: from 0 to 1 min B=40%, from 1 to 5 min B=40% to 60%, from 5 to 6 min B=60% to 90%.
Condition J is the following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+ 200 to 3000 uma;
Elution system: from 0 to 1 min B=35%, from 1 to 5 min B=35% to 70%, from 5 to 6 min B=70% to 90%.
Condition K is the following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+ 200 to 3000 uma;
Elution system: from 0 to 1 min B=35%, from 1 to 5 min B=35% to 55%, from 5 to 6 min B=55% to 90%.
Condition L is the following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+ 200 to 3000 uma;
Elution system: from 0 to 1 min B=30%, from 1 to 5 min B=30% to 50%, from 5 to 6 min B=50% to 80%

Example 3: In Vitro Analysis of Peptides of the Invention on RXFP1 Receptors (OVCAR5 cAMP Assay)

A. Method

OVCAR5 cells expressing endogenous RXFP1 were used to test RXP1 agonist properties of peptides of the invention, and in particular of the peptides of sequence SEQ ID NO: 1-193.

Since RXFP1 is a Gs coupled GPCR, cAMP was used as readout of RXFP1 activation.

Isobutyl Methyl Xanthine (IBMX) was used to inhibit phosphodiesterase activity facilitating cAMP measurements. HTRF (Homogenous Time Resolved Fluorescence) technology was used to detect cAMP due to its great sensitivity.

In summary, OVCAR5 were grown in regular medium (RPMI) containing 10% fetal calf serum (FCS) and 1% antibiotics (penicillin/streptomycin).

Before the experiments, cells were detached with accutase and incubated for 40 minutes at 37° C. with 1 mM (3-isobutyl-1-methylxanthine) IBMX.

Cells were then distributed in 384 black well plates containing increasing concentrations of the different peptides in a fix volume of medium (without FCS).

After an incubation of 30 min at 37° C. in an humid incubator in 5% CO$_2$, the reaction was stopped by adding a fixed volume of a solution containing a lysis buffer and cAMP-D2 (cAMP labeled with the dye d2) and the anti cAMP antibody linked to Europium and used for cAMP detection.

Readout of the experiment were performed on a fluorimeter allowing HTRF measurement. Activation curves were generated by plotting the intracellular value of cAMP versus log 10 of the compound concentration.

The 50% activation concentration (EC$_{50}$) was calculated by nonlinear regression using the sigmoidal dose-response (variable slope) equation with Prism 5 software.

Emax % is determined as the maximal intracellular value of cAMP for test compound (upper limit of cAMP vs concentration curve) divided by the maximal intracellular value of cAMP for H2-relaxin determined in the same test occasion multiplied by 100.

$$Emax \% = 100 \times [cAMP_{test\ cpd}]/[cAMP_{H2-RLX}]$$

B. Results

The results obtained with peptides of sequence SEQ ID NO: 1-193 are represented in the following Table 2.

TABLE 2

| SEQ ID NO | OVCAR 5 cells (cAMP) | |
|---|---|---|
| | EC50 (nM) | EMax |
| 1 | 85.3 | 85% |
| 2 | 24.0 | 100% |
| 3 | 28.5 | 93% |
| 4 | 31.7 | 99% |

TABLE 2-continued

| SEQ ID NO | OVCAR 5 cells (cAMP) | |
|---|---|---|
| | EC50 (nM) | EMax |
| 5 | 86.8 | 105% |
| 6 | 18.0 | 100% |
| 7 | 17.6 | 87% |
| 8 | 26.7 | 98% |
| 9 | 11.8 | 95% |
| 10 | 18.9 | 96% |
| 11 | 14.7 | 89% |
| 12 | 26.7 | 76% |
| 13 | 8.1 | 81% |
| 14 | 0.04 | 88% |
| 15 | 0.32 | 92% |
| 16 | 0.02 | 87% |
| 17 | 0.17 | 95% |
| 18 | 0.41 | 83% |
| 19 | 0.15 | 96% |
| 20 | 0.45 | 88% |
| 21 | 38.6 | 88% |
| 22 | 21.4 | 104% |
| 23 | 3.62 | 89% |
| 24 | 3.20 | 74% |
| 25 | 1.21 | 95% |
| 26 | 0.57 | 85% |
| 27 | 0.30 | 86% |
| 28 | 4.64 | 78% |
| 29 | 2.50 | 78% |
| 30 | 0.92 | 89% |
| 31 | 0.71 | 86% |
| 32 | 1.04 | 96% |
| 33 | 0.61 | 100% |
| 34 | 4.73 | 95% |
| 35 | 1.69 | 95% |
| 36 | 0.89 | 84% |
| 37 | 2.49 | 83% |
| 38 | 0.21 | 89% |
| 39 | 0.03 | 91% |
| 40 | 0.02 | 90% |
| 41 | 0.09 | 87% |
| 42 | 0.01 | 91% |
| 43 | 0.14 | 106% |
| 44 | 16.1 | 75% |
| 45 | 0.81 | 79% |
| 46 | 0.61 | 79% |
| 47 | 2.56 | 100% |
| 48 | 0.25 | 99% |
| 49 | 1.65 | 106% |
| 50 | 75.9 | 95% |
| 51 | 71.2 | 100% |
| 52 | 56.0 | 98% |
| 53 | 15.3 | 97% |
| 54 | 18.6 | 98% |
| 55 | 19.3 | 94% |
| 56 | 0.51 | 95% |
| 57 | 4.4 | 93% |
| 58 | 14.8 | 83% |
| 59 | 28.2 | 85% |
| 60 | 0.11 | 91% |
| 61 | 0.17 | 93% |
| 62 | 1.14 | 87% |
| 63 | 0.84 | 80% |
| 64 | 0.20 | 81% |
| 65 | 0.12 | 93% |
| 66 | 0.57 | 83% |
| 67 | 0.39 | 89% |
| 68 | 0.63 | 94% |
| 69 | 0.56 | 87% |
| 70 | 0.28 | 86% |
| 71 | 0.52 | 87% |
| 72 | 0.17 | 93% |
| 73 | 0.12 | 90% |
| 74 | 0.07 | 85% |
| 75 | 0.07 | 88% |
| 76 | 0.80 | 89% |
| 77 | 2.94 | 92% |
| 78 | 1.04 | 73% |
| 79 | 0.40 | 75% |
| 80 | 0.73 | 68% |
| 81 | 0.22 | 84% |
| 82 | 0.02 | 89% |
| 83 | 0.85 | 92% |
| 84 | 0.09 | 76% |
| 85 | 0.77 | 75% |
| 86 | 0.69 | 79% |
| 87 | 1.63 | 71% |
| 88 | 0.11 | 74% |
| 89 | 0.03 | 79% |
| 90 | 0.07 | 89% |
| 91 | 0.01 | 88% |
| 92 | 0.26 | 82% |
| 93 | 0.14 | 87% |
| 94 | 2.74 | 90% |
| 95 | 1.03 | 87% |
| 96 | 1.77 | 89% |
| 97 | 4.92 | 98% |
| 98 | 0.74 | 99% |
| 99 | 0.01 | 87% |
| 100 | 0.16 | 90% |
| 101 | 0.16 | 86% |
| 102 | 0.08 | 80% |
| 103 | 0.09 | 79% |
| 104 | 0.16 | 89% |
| 105 | 0.03 | 88% |
| 106 | 0.34 | 93% |
| 107 | 0.63 | 85% |
| 108 | 0.15 | 94% |
| 109 | 0.15 | 98% |
| 110 | 0.17 | 80% |
| 111 | 0.21 | 92% |
| 112 | 0.32 | 88% |
| 113 | 0.53 | 89% |
| 114 | 1.34 | 90% |
| 115 | 0.17 | 93% |
| 116 | 1.00 | 89% |
| 117 | 1.16 | 86% |
| 118 | 1.79 | 86% |
| 119 | 1.21 | 83% |
| 120 | 109.9 | 92% |
| 121 | 0.76 | 91% |
| 122 | 0.10 | 93% |
| 123 | 0.38 | 88% |
| 124 | 0.29 | 88% |
| 125 | 0.10 | 89% |
| 126 | 9.60 | 91% |
| 127 | 4.40 | 88% |
| 128 | 0.22 | 91% |
| 129 | 1.00 | 89% |
| 130 | 0.30 | 93% |
| 131 | 0.26 | 92% |
| 132 | 1.70 | 87% |
| 133 | 0.01 | 83% |
| 134 | 6.30 | 100% |
| 135 | 0.95 | 97% |
| 136 | 0.03 | 92% |
| 137 | 0.21 | 92% |
| 138 | 0.02 | 91% |
| 139 | 0.30 | 92% |
| 140 | 0.40 | 88% |
| 141 | 0.16 | 87% |
| 142 | 0.02 | 91% |
| 143 | 0.40 | 88% |
| 144 | 4.10 | 94% |
| 145 | 0.40 | 99% |
| 146 | 0.02 | 89% |
| 147 | 2.14 | 86% |
| 148 | 0.11 | 94% |
| 149 | 0.11 | 87% |
| 150 | 0.07 | 92% |
| 151 | 0.14 | 90% |
| 152 | 0.04 | 91% |
| 153 | 0.26 | 89% |
| 154 | 0.40 | 92% |

TABLE 2-continued

| SEQ ID NO | OVCAR 5 cells (cAMP) | |
|---|---|---|
| | EC50 (nM) | EMax |
| 155 | 1.17 | 95% |
| 156 | 0.06 | 90% |
| 157 | 0.02 | 89% |
| 158 | 0.14 | 90% |
| 159 | 0.02 | 88% |
| 160 | 0.28 | 86% |
| 161 | 12.1 | 94% |
| 162 | 0.12 | 91% |
| 163 | 5.30 | 87% |
| 164 | 0.79 | 93% |
| 165 | 0.38 | 105% |
| 166 | 0.26 | 92% |
| 167 | 0.05 | 93% |
| 168 | 0.06 | 91% |
| 169 | 0.01 | 89% |
| 170 | 0.01 | 87% |
| 171 | 0.18 | 83% |
| 172 | 0.56 | 95% |
| 173 | 0.19 | 85% |
| 174 | 0.41 | 88% |
| 175 | 2.21 | 87% |
| 176 | 3.00 | 90% |
| 177 | 1.5 | 91% |
| 178 | 17.6 | 93% |
| 179 | 19.9 | 80% |
| 180 | 1.18 | 84% |
| 181 | 1.63 | 79% |
| 182 | 0.19 | 99% |
| 183 | 0.08 | 94% |
| 184 | 0.27 | 100% |
| 185 | 0.05 | 100% |
| 186 | 0.18 | 100% |
| 187 | 0.33 | 100% |
| 188 | 0.75 | 100% |
| 189 | 0.42 | 100% |
| 190 | 1.29 | 93% |
| 191 | 0.17 | 93% |
| 192 | 0.62 | 91% |
| 193 | 0.20 | 100% |

It appears that peptides according to the invention possess very interesting RXP1 agonist properties, and are very effective to bind and activate RXFP1.

They are moreover all significantly and unexpectedly superior to the peptides from the prior art when it comes to activate the RXFP1 receptor.

The same experiment has been performed with peptides from the prior art (WO2015/157829) known under the names B7-33 C11.23S, AcB7-33 C11.23S and KKK(AcB7-29 C11.23S).

The following $EC_{50}$ results have been obtained for these three peptides.

TABLE 3

| Name | cAMP assay in OVCAR 5 cells | |
|---|---|---|
| | EC50 (nM) | Emax |
| B7-33 C11.23S | 1641 | 90% |
| AcB7-33 C11.23S | 929 | 70% |
| KKKK(AcB7-29 C11.23S) | 206 | 84% |

As demonstrate above, the peptides according to the invention possess very interesting RXFP1 agonist properties, and are very effective to activate RXFP1. They are moreover all significantly and unexpectedly superior to the peptides from the prior art.

Example 4: Solubility Testing of Peptides of the Invention in Buffer

A. Method

Prior to the testing of solubility of a peptide batch, its purity (HPLC-UV) was determined.

Study Media:

Phosphate buffer 50 mM pH 6.5: 15.9 ml $Na_2HPO_4$ 0.1 M (Carlo Erba 480087)+34.1 ml $NaH_2PO_4$ 0.1 M (Carlo Erba 480141)+$H_2O$ MilliQ QSP 100 ml Phosphate buffer 50 mM pH 7.4: 40.5 ml $Na_2HPO_4$ 0.1 M (Carlo Erba 480087)+9.5 ml $NaH_2PO_4$ 0.1 M (Carlo Erba 480141)+$H_2O$ MilliQ QSP 100 ml Acetate Buffer 50 mM pH4.5: 0.75 g $C_2H_3CO_2Na$, $3H_2O$ (Sigma 57545)+0.35 ml $CH_3CO_2H$ 100% solution dissolved in Millipore water, adjusted to pH with diluted (1:1) $CH_3CO_2H$ and diluted to 250 ml with Millipore water.

In a 4 ml Ependorph vial, an accurately weighed sample of compound was diluted in study media to obtain target concentration of 2, 6 or 10 mg/ml of pure compound. The sample vials were shacked (rock 'roll shaker) for ~19 h. 3004, Aliquots ( ) were filtered through a Millipore "Solvinert" plate (0.45 μm—PTFE hydrophilic). The solubility was then determined by comparison of a 0.2 pL-injection of the filtrate with the UV peak areas obtained with a stock solution of the peptide at a concentration of 1.2 mg/ml in DMSO (based on % purity), injecting various volumes ranging from 0.2-2 pL.

Analysis:

pH was measured with a micro electrode

HPLC Conditions:

Waters Acquity UPLC System with DAD detector

Column: Waters Peptide Column CSH C18 (130 Å; 1.7 μm; 50*2.1 mm)

Column temperature: 60° C.

Flow: 0.3 ml/min

Full loop (about 5 μL)—overfill factor 5

Weak et Strong wash: $H_2O$/ACN (75/25; V/V); Seal wash: $H_2O$/IsOH (95/5; V/V). Mobile phase:

Solvent A: 0.05% TFA in $H_2O$; Solvent B: 0.035% TFA in $CH_3CN$

Gradient: from 0 to 12 min B=2% to 60%, from 12 to 14 min B=60% to 100%. Column washing 100% B 1 min, column equilibration 2% B 2.5 min.

UV detector: wavelength: 220 nm.

B. Results

The solubility results obtained are represented in the following Table 4.

TABLE 4

| SEQ ID NO | Solubility Acetate buffer pH 4.5* | Solubility phosphate buffer pH 7.4* |
|---|---|---|
| 14 | ND | >2.1 mg/ml** |
| 20 | 5.6 mg/ml | 5.6 mg/ml |
| 23 | 7.0 mg/ml | 7.0 mg/ml |
| 30 | 7.0 mg/ml | 7.0 mg/ml |
| 33 | 5.4 mg/ml | 5.4 mg/ml |
| 58 | 5.7 mg/ml | 5.7 mg/ml |
| 81 | 11.9 mg/ml*** | 11.038*** |
| 95 | 5.6 mg/ml | 5.6 mg/ml |
| 109 | 5.9 mg/ml | 5.9 mg/ml |
| 150 | 1.5 mg/ml**** | >10 mg/ml**** |
| 154 | >10 mg/ml**** | >10 mg/ml**** |
| 170 | 9.8 mg/ml**** | >10 mg/ml**** |

ND = Not determined;
*Target solubility: 6.0 mg/ml except:
**Target solubility: 2.0 mg/ml;
***Target solubility 15.0 mg/ml;
****Target solubility 10.0 mg/ml.

The same experiment has been performed with peptides from the prior art (WO2015/157829) known under the names B7-33 C11.23S, AcB7-33 C11.23S and KKK(AcB7-29 C11.23S).

The following solubility results have been obtained for these three peptides.

TABLE 5

| Name | Solubility Acetate buffer pH 4.5** | Solubility phosphate buffer pH 7.4** |
|---|---|---|
| B7-33 C11.23S | 1.9 mg/ml | 0.014 mg/ml |
| AcB7-33 C11.23S | 1.54 mg/ml | <0.001 mg/ml |
| KKKK(AcB7-29 C11.23S) | 2.3 mg/ml | 0.177 mg/ml |

**Target solubility: 2.0 mg/ml

The peptides of the invention display improved solubility compared to compounds of the prior art. This property would allow a larger range of concentration when preparing injectable solutions thus expanding in-vivo dosage ranges.

Example 5: Stability Testing of Peptides in Rat or Human Plasma or Blood

A. Method

Prior to the testing of stability in plasma (or blood) of a peptide batch, its purity (HPLC-UV) was determined.

Study Media:

Rat and Human plasma: anti-coagulant sodium or lithium heparin.

Rat and Human blood: anti-coagulant sodium or lithium heparin.

Stock solution:

100 µM solution of study compound in 50 mM Phosphate buffer pH 7.4.

950 µL plasma (or blood) was pre-incubated for 5 min at 37° C. 50 µL of compound stock solution was added. Final compound concentration=5 µM. Vortex and transfer 150L, plasma (or blood) into an Eppendorf for each time point. The time points 0-1 and −4 h were carried out in duplicate for each species.

After incubation 150 µL, plasma (or blood) was extracted with 600 µL, Acetonitrile containing with 1% TFA. Then, vortexed and centrifuged 10 min at 14600 rpm. 200 µL supernatant was dried under $N_2$. The sample was reconstituted in 200 µL of $H_2O/CH_3CN$ 98/2+0.1% FA+50 ng/ml Labetalol and analyzed using the analytical system used in solubility and stability studies.

For determination of the amount of the remaining peptide, the peak areas of the target compound at t0 and each time point days were compared, resulting in "% remaining peptide", following the equation:

% remaining peptide=[(peak area peptide time)× 100]/peak area peptide t0. The stability is expressed as "% remaining peptide".

Acceptance criteria: The tests compounds were considered stable if precision was ~15% and the recovery was within 85-115% range.

B. Results

The Plasma and blood stability results obtained are represented in the following Table 6.

TABLE 6

| | Human Plasma stability* % remaining | | | Rat plasma stability* % remaining | | |
|---|---|---|---|---|---|---|
| SEQ ID NO | T = 0 | 1 h | 4 h | T = 0 | 1 h | 4 h |
| 7 | 100 | 110** | 91** | 100 | 110** | 93** |
| 9 | 100 | ND | ND | 100 | 84** | 92** |
| 19 | 100 | 86 | 90 | 100 | 99 | 89 |
| 33 | 100 | 99 | 96 | 100 | 93 | 80 |
| 58 | 100 | 100 | 11 | 100 | 96 | 101 |
| 63 | 100 | 93** | 87** | 100 | 95** | 79** |
| 81 | 100 | 111 | 111 | 100 | 101 | 114 |
| 107 | 100 | 98 | 106 | 100 | 93 | 110 |
| 110 | 100 | 101 | 114 | 100 | 96 | 98 |
| 150 | 100 | 34** | 78** | 100 | 86** | 90** |
| 154 | 100 | 91** | 96** | 100 | 99** | 95** |
| 170 | 100 | 107** | 106** | 100 | 107** | 99** |

*Stability in plasma except
**stability in blood;
ND: Not Determined

The same experiment has been performed with peptides from the prior art (WO2015/157829) known under the names B7-33 C11.23S, AcB7-33, C11.23S and KKK(AcB7-29 C11.23S).

The following plasma stability results have been obtained for these three peptides.

TABLE 7

| | Human Plasma stability % remaining | | | Rat plasma stability % remaining | | |
|---|---|---|---|---|---|---|
| Name | T = 0 | 1 h | 4 h | T = 0 | 1 h | 4 h |
| B7-33 C11.23S | 100 | 18 | 3 | 100 | 15 | 2 |
| Ac B7-33 | 100 | 67 | 18 | 100 | 16 | 2 |
| KKKK(Ac B7-29 C11.23S) | 100 | 41 | 31 | 100 | 23 | 14 |

The peptides of the invention appear to be more stable in plasma and/or blood than compounds of the prior art.

Example 6: Pharmacokinetic (PK) Determination of Peptides After In-Vivo Administration to Rats A. Method:

Prior to the testing of a peptide batch, its purity (HPLC-UV) was determined. Dose was corrected for presence of salts, solvent and purity.

Bioanalytical screening method for quantification of peptides in rat:

Sprague Dawley rats were dosed with study peptide at a dose of 1 mg/kg intravenously (i.v.) or 3 mg/kg subcutaneously (s.c.) as a solution in PBS (0.2 mg/ml and 0.6 mg/ml respectively).

Blood samples were collected after: 0.083, 0.25, 0.5, 1, 2, 4, 8, 24, 48 and 72 h (i.v. route) and 0.25, 0.5, 1, 2, 4, 6, 8, 10, 24, 48 and 72 h (s.c route) post application.

Plasma samples were analyzed after protein precipitation via liquid chromatography mass spectrometry (LC/MS).

PK parameters and half-life were calculated using Phoenix 64 (WinNonlin 6.4)-Pharsight (Certara™) (non-compartment model). Values below the limit of quantification (BLQ) were replaced by zero for subsequent calculations and PK analysis.

B. Results:

The PK parameters obtained are represented in the following Table 8.

The following abbreviations are used:

T½: in-vivo half life, time required for test compound plasma concentration to be divided by two during the PK experiment.

C0: Extrapolated test compound plasma concentration at t=0 time point (i.v. route).

Cmax: maximal test compound plasma concentration at the indicated time point (s.c. route).

Tmax: Time point where Cmax is attained.

F %: s.c. vs i.v. bioavailability, dose-corrected area under curve (AUC) s.c. route divided by AUC i.v.

TABLE 8

| SEQ ID NO | Rat PK, 1 mg/kg i.v. | | Rat PK, 3 mg/kg s.c. | | |
|---|---|---|---|---|---|
| | T½ (h) | C0 (µM) | Cmax (µM) | Tmax (-h) | F % |
| 7 | 4.30 | 4.77 | 1.70 | 6.0 | 53% |
| 9 | 3.00 | 4.99 | 2.32 | 6.0 | 42% |
| 14 | 3.40 | 4.00 | 1.50 | 6.0 | 93% |
| 16 | 3.38 | 2.65 | 1.88 | 8.0 | 53% |
| 17 | 5.80 | 3.50 | 2.40 | 8.0 | 73% |
| 20 | 3.96 | 4.00 | 3.00 | 8.0 | 73% |
| 23 | 8.96 | 2.90 | 1.70 | 6.0 | 84% |
| 24 | 6.40 | 3.70 | 1.80 | 5.0 | 81% |
| 26 | 5.80 | 2.33 | 0.77 | 8.0 | 72% |
| 27 | 6.90 | 3.20 | 1.50 | 8.0 | 62% |
| 30 | 4.80 | 2.20 | 0.60 | 4.0 | 105% |
| 33 | 4.30 | 4.20 | 2.50 | 8.0 | 60% |
| 37 | 2.55 | 5.56 | 1.71 | 6.0 | 40% |
| 38 | 7.16 | 4.37 | 2.50 | 8.0 | 79% |
| 39 | 3.70 | 4.10 | 1.57 | 8.0 | 62% |
| 40 | 3.60 | 7.08 | 1.54 | 6.0 | 66% |
| 42 | 3.70 | 3.00 | 2.00 | 5.0 | 65% |
| 45 | 2.88 | 2.90 | 2.20 | 7.0 | 65% |
| 58 | 7.90 | 4.02 | 1.34 | 6.0 | 55% |
| 63 | 5.72 | 6.02 | 2.40 | 10.0 | 47% |
| 74 | 3.89 | 3.00 | 1.63 | 7.0 | 70% |
| 81 | 3.90 | 2.60 | 1.50 | 8.0 | 74% |
| 82 | 3.40 | 2.60 | 1.20 | 7.0 | 114% |
| 91 | 3.00 | 2.90 | 1.30 | 7.0 | 89% |

TABLE 8-continued

| SEQ ID NO | Rat PK, 1 mg/kg i.v. | | Rat PK, 3 mg/kg s.c. | | |
|---|---|---|---|---|---|
| | T½ (h) | C0 (µM) | Cmax (µM) | Tmax (-h) | F % |
| 100 | 2.80 | 3.10 | 2.36 | 7.0 | 41% |
| 101 | 1.80 | 1.80 | 1.00 | 7.0 | 39% |
| 102 | 1.16 | 4.25 | 1.45 | 8.0 | 78% |
| 107 | 2.50 | 2.60 | 1.60 | 8.0 | 27% |
| 112 | 3.30 | 3.50 | 2.20 | 8.0 | 63% |
| 131 | 6.30 | 2.50 | 1.39 | 8.0 | 82% |
| 136 | 2.90 | 3.00 | 1.87 | 8.0 | 86% |
| 145 | 5.40 | 3.44 | 1.67 | 8.0 | 70% |
| 149 | 4.33 | 3.33 | 2.50 | 6.0 | 128% |
| 150 | 5.70 | 3.60 | 2.10 | 8.0 | 76% |
| 154 | 5.00 | 4.52 | 1.89 | 8.0 | 72% |
| 157 | 6.69 | 4.35 | 1.51 | 8.0 | 59% |
| 160 | 5.30 | 2.50 | 1.20 | 7.0 | 66% |
| 162 | 5.00 | 3.20 | 2.30 | 5.0 | 64% |
| 169 | 5.80 | 3.04 | 1.89 | 6.0 | 69% |
| 170 | 10.00 | 7.76 | 0.78 | 4.0 | 87% |
| 184 | 7.3 | 4.7 | 2.8 | 7.0 | 71% |

The same experiment has been performed with H2-Relaxin.

TABLE 9

| Compound | Rat PK, 1 mg/kg i.v. | |
|---|---|---|
| | T½ (h) | C0 (µM) |
| H2-Relaxin | 0.46 | 0.87 |

Compared to H2-relaxin, selected peptides of the invention display improved pharmacokinetic parameters. In particular their in-vivo half-life in rat, ranged from 1 h to 10 h. Such peptides could then retain their efficacy for longer period of time allowing once a day administration by the intravenous or subcutaneous route.

```
                        Sequence listing

SEQ ID NO: 1
Ac-L E G R-E-K-V-R-A-A-I-Aib-Aib-E-G-Nle-S-T-W-S-Aib-R-K-K(Palm)-NH2

SEQ ID NO: 2
Ac-L-E-G-R-E-K-V-R-A-Q-I-Aib-Aib-E-G-Nle-S-T-W-S-Aib-R-K-K(gE-Palm)-NH2

SEQ ID NO: 3
Ac-L-E-G-R-E-K-V-R-A-Q-I-Aib-Aib-E-G-Nle-S-T-W-S-Aib-R-K-K(gE-Stea)-NH2

SEQ ID NO: 4
Ac-E-L-E-G-R-E-K-V-R-A-A-I-Aib-Aib-E-G-Nle-S-T-W-S-Aib-R-K-K(gE-gE-Palm)-NH2

SEQ ID NO: 5
Ac-L-E-G-R-E-K-V-R-A-Q-I-Aib-Aib-E-G-M-S-T-W-S-Aib-R-K(gE-gE-Palm)-NH2

SEQ ID NO: 6
Ac-E-L-E-G-R-E-K-V-R-A-A-I-Aib-Aib-E-G-Nle-S-T-W-S-Aib-R-K-K(gE-gE-gE-Palm)-
NH2

SEQ ID NO: 7
Ac-L-E-G-R-E-K-V-R-A-Q-I-Aib-Aib-E-G-M-S-T-W-S-Aib-R-K-K(gE-gE-gE-Palm)-NH2

SEQ ID NO: 8
Ac-L-E-G-R-E-K-V-R-A-Q-I-Aib-Aib-E-G-Nle-S-T-W-S-Aib-R-K-K(gE-gE-gE-Palm)-NH2

SEQ ID NO: 9
Ac-L-E-G-R-E-K-V-R-A-Q-I-Aib-Aib-E-G-Nle-S-T-W-S-Aib-R-K-K(gE-gE-gE-Stea)-NH2
```

```
SEQ ID NO: 10
Ac-L-E-G-R-E-K-V-R-A-Q-I-Aib-Aib-E-G-Nle-S-T-W-S-Aib-R-K-PEG₂-K(gE-gE-gE-Palm)-
NH₂

SEQ ID NO: 11
Ac-L-E-G-R-E-K-V-R-A-Q-I-Aib-Aib-E-G-Nle-S-T-W-S-Aib-R-K-PEG₂-PEG₂-K(gE-gE-gE-
Palm)-NH₂

SEQ ID NO: 12
Ac-L-E-G-R-E-K-V-R-A-Q-I-Aib-Aib-E-G-Nle-S-T-W-S-Aib-R-K-PEG₂-K(PEG₂-gE-gE-gE-
Palm)-NH₂

SEQ ID NO: 13
Ac-L-E-G-R-E-K-V-R-A-Q-I-Aib-Aib-E-G-Nle-S-T-W-S-Aib-R-K-PEG₂-K(PEG₂-PEG₂-gE-
gE-gE-Palm)-NH₂

SEQ ID NO: 14
Ac-L-E-G-R-E-K-V-R-A-K(Ac)-I-Aib-Aib-E-G-Nle-S-T-W-S-Aib-R-K-K(Ac)-PEG₂-PEG₂-
PEG₂-K(gE-gE-gE-Stea)-NH₂

SEQ ID NO: 15
Ac-L-E-G-R-E-K-V-R-A-K(Ac)-I-Aib-Aib-E-G-Nle-S-T-W-S-Aib-R-K-K-PEG₂-PEG₂-PEG₂-
PEG₂-K(gE-gE-gE-gE-Stea)-NH₂

SEQ ID NO: 16
Ac-L-E-G-R-E-K-V-R-A-K(Ac)-I-Aib-Aib-E-G-Nle-S-T-W-S-Mly-R-K-K(Ac)-PEG₂-PEG₂-
PEG₂-K(gE-gE-gE-gE-Stea)-NH₂

SEQ ID NO: 17
Ac-L-E-G-R-E-K-V-R-A-K(Ac)-I-Aib-Aib-E-G-Nle-S-T-W-S-Mly-R-K-K(Ac)-PEG₂-PEG₂-
PEG₂-K(gE-gE-gE-gE-Palm)-NH₂

SEQ ID NO: 18
Ac-L-E-G-R-E-K-V-R-A-K(Ac)-I-Aib-Aib-E-G-Nle-S-T-W-S-Aib-R-K-K(Ac)-PEG₂DGA-
K(gE-gE-gE-Stea)-NH₂

SEQ ID NO: 19
Ac-L-E-G-R-E-K-V-R-A-K(Ac)-I-Aib-Aib-E-G-Nle-S-T-W-S-Aib-R-K-K(Ac)-PEG₂DGA-
PEG₂DGA-K(gE-gE-gE-Stea)-NH₂

SEQ ID NO: 20
Ac-L-E-G-R-E-K-V-R-A-K(Ac)-I-Aib-Aib-E-G-Nle-S-T-W-S-Aib-R-K-K(Ac)-PEG₂DGA-
PEG₂DGA-PEG₂DGA-K(gE-gE-gE-Stea)-NH₂

SEQ ID NO: 21
Ac-L-E-G-R-E-K-V-R-A-Q-I-Aib-Aib-E-G-Nle-S-T-W-S-Aib-R-K-K(Ac)-PEG₁₂-K(Stea)-NH₂

SEQ ID NO: 22
Ac-L-E-G-R-E-K-V-R-A-Q-I-Aib-Aib-E-G-Nle-S-T-W-S-Aib-R-K-K-PEG₁₂-K(gE-Stea)-NH₂

SEQ ID NO: 23
Ac-L-E-G-R-E-K-V-R-A-Q-I-Aib-Aib-E-G-M-S-T-W-S-Aib-R-K-PEG₁₂-K(gE-gE-gE-Palm)-
NH₂

SEQ ID NO: 24
Ac-L-E-G-R-E-K-V-R-A-Q-I-Aib-Aib-E-G-Nle-S-T-W-S-Aib-R-K-PEG₁₂-K(gE-gE-gE-Palm)-
NH₂

SEQ ID NO: 25
Ac-L-E-G-R-E-K-V-R-A-K(Ac)-I-Aib-Aib-E-G-M-S-T-W-S-Aib-R-K-PEG₁₂-K(gE-gE-gE-
Palm)-NH₂

SEQ ID NO: 26
Ac-L-E-G-R-E-K-V-R-A-K(Ac)-I-Aib-Aib-E-G-Nle-S-T-W-S-Aib-R-K-K(Ac)-PEG₁₂-K(gE-
gE-gE-Palm)-NH₂

SEQ ID NO: 27
Ac-L-E-G-R-E-K-V-R-Aib-K(Ac)-I-Aib-Aib-E-G-Nle-S-T-W-S-Aib-R-K-K(Ac)-PEG₁₂-K(gE-
gE-gE-Palm)-NH₂

SEQ ID NO: 28
Ac-L-E-G-R-E-K-V-R-Aib-Q-I-Aib-Aib-E-G-Nle-S-T-W-S-Aib-R-K-K(Ac)-PEG₁₂-K(gE-gE-
gE-Palm)-NH₂
```

```
                      Sequence listing

SEQ ID NO: 29
Ac-L-E-G-R-E-K-V-R-A-K(Ac)-I-Aib-Aib-E-G-Nle-S-T-1Nal-S-Aib-R-K-PEG₁₂-K(gE-gE-gE-
Palm)-NH₂

SEQ ID NO: 30
Ac-L-E-G-R-E-K-V-R-A-Q-I-Aib-Aib-E-G-Nle-S-T-W-S-Aib-R-K-PEG₁₂-K(gE-gE-gE-Stea)-
NH₂

SEQ ID NO: 31
Ac-L-E-G-R-E-K-V-R-A-Q-I-Aib-Aib-E-G-Nle-S-T-W-S-Aib-R-K-K-PEG₁₂-K(gE-gE-gE-
Stea)-NH₂

SEQ ID NO: 32
Ac-L-E-G-R-E-K-V-R-A-K(Ac)-I-Aib-Aib-E-G-Nle-S-T-W-S-Aib-R-K-K-PEG₁₂-K(gE-gE-gE-
Stea)-NH₂

SEQ ID NO: 33
Ac-L-E-G-R-E-K-V-R-A-K(Ac)-I-Aib-Aib-E-G-Nle-S-T-W-S-Aib-R-K-K(Ac)-PEG₁₂-K(gE-
gE-gE-Stea)-NH₂

SEQ ID NO: 34
Ac-L-E-G-R-E-K-V-R-A-K(Ac)-I-Aib-Aib-E-G-Nle-S-T-W-S-Aib-R-K-PEG₁₂-K(gE-gE-gE-
Stea)-NH₂

SEQ ID NO: 35
Ac-L-E-G-R-E-K-V-R-A-K(Ac)-I-Aib-Aib-E-G-M-S-T-W-S-Aib-R-K-PEG₁₂-K(gE-gE-gE-
Stea)-NH₂

SEQ ID NO: 36
Ac-L-E-G-R-E-K-V-R-Aib-K(Ac)-I-Aib-Aib-E-G-Nle-S-T-W-S-Aib-R-K-K(Ac)-PEG₁₂-K(gE-
gE-gE-Stea)-NH₂

SEQ ID NO: 37
Ac-L-E-G-R-E-K-V-R-Aib-K(Ac)-I-Aib-Aib-E-G-Nle-S-T-1Nal-S-Aib-R-K-K(Ac)-PEG-12-
K(gE-gE-gE-Stea)-NH₂

SEQ ID NO: 38
Ac-L-E-G-R-E-K-V-R-A-K(Ac)-I-Aib-Aib-E-G-Nle-S-T-W-S-Aib-R-K-PEG₁₂-K(gE-gE-gE-
Palm)-NH₂

SEQ ID NO: 39
Ac-L-E-G-R-E-K-V-R-A-K(Ac)-I-Aib-Aib-E-G-Nle-S-T-W-Mse-K-R-K-K(Ac)-PEG₁₂-K(gE-
gE-gE-Stea)-NH₂

SEQ ID NO: 40
Ac-L-E-G-R-E-K-V-R-A-K(Ac)-I-Aib-Aib-E-G-Nle-S-T-W-Mse-Mly-R-K-K(Ac)-PEG₁₂-
K(gE-gE-gE-Stea)-NH₂

SEQ ID NO: 41
Ac-L-E-G-R-E-K-V-R-A-K(Ac)-I-Aib-Aib-E-G-Nle-S-T-W-Mse-Aib-R-K-K(Ac)-PEG₁₂-K(gE-
gE-gE-Stea)-NH₂

SEQ ID NO: 42
Ac-L-E-G-R-E-K-V-R-A-K(Ac)-I-Aib-Aib-E-G-Nle-S-T-W-S-Mly-R-K-K(Ac)-PEG₁₂-K(gE-
gE-gE-Stea)-NH₂

SEQ ID NO: 43
Ac-L-E-G-R-E-K-V-R-A-K(Ac)-I-Aib-Aib-E-G-Nle-S-T-W-S-Mly-R-K-K(Ac)-PEG₁₂-K(gE-
gE-gE-Palm)-NH₂

SEQ ID NO: 44
Ac-L-E-G-R-E-K-V-R-A-K(Ac)-I-Aib-Aib-E-G-Q-S-T-Y-S-Aib-R-K-K(Ac)-K(PEG₂-PEG₂-
PEG₂-gE-gE-gE-Palm)-NH₂

SEQ ID NO: 45
Ac-L-E-G-R-E-K-V-R-A-K(Ac)-I-Aib-Aib-E-G-Nle-S-T-1Nal-S-Aib-R-K-PEG₁₂-K(gE-gE-gE-
Stea)-NH₂

SEQ ID NO: 46
Ac-L-E-G-R-E-K-V-R-A-K(Ac)-I-Aib-Aib-E-G-Nle-S-T-Y-S-Aib-R-K-K(Ac)-PEG₁₂-K(gE-
gE-gE-Stea)-NH₂

SEQ ID NO: 47
Ac-L-E-G-R-E-K-V-R-A-Q-I-Aib-Aib-E-G-M-S-T-W-S-Aib-R-K-PEG₂₄-K(gE-gE-gE-Palm)-
NH₂
```

| Sequence listing |
| --- |

SEQ ID NO: 48
Ac-L-E-G-R-E-K-V-R-A-K(Ac)-I-Aib-Aib-E-G-Nle-S-T-W-S-Aib-R-K-K-PEG$_{28}$-K(gE-gE-gE-Stea)-NH$_2$ SEQ ID NO: 49
Ac-L-E-G-R-E-K-V-R-A-K(Ac)-I-Aib-Aib-E-G-Nle-S-T-W-S-Aib-R-K-K(Ac)-PEG$_{28}$-K(gE-gE-gE-Stea)-NH$_2$ SEQ ID NO: 50
Ac-L-E-G-R-E-K-V-R-A-Q-I-Aib-Aib-E-G-Nle-S-T-W-S-Aib-R-K-K(PEG$_2$-Palm)-NH$_2$ SEQ ID NO: 51
Ac-L-E-G-R-E-K-V-R-A-Q-I-Aib-Aib-E-G-Nle-S-T-W-S-Aib-R-K-K(Ac)-K(PEG$_2$-PEG$_2$-Stea)-NH$_2$ SEQ ID NO: 52
Ac-L-E-G-R-E-K-V-R-A-Q-I-Aib-Aib-E-G-Nle-S-T-W-S-Aib-R-K-K(Ac)-K(PEG$_2$-PEG$_2$-PEG$_2$-Stea)-NH$_2$ SEQ ID NO: 53
Ac-L-E-G-R-E-K-V-R-A-Q-I-Aib-Aib-E-G-Nle-S-T-W-S-Aib-R-K-K(PEG$_2$-gE-Palm)-NH$_2$ SEQ ID NO: 54
Ac-E-L-E-G-R-E-K-V-R-A-A-I-Aib-Aib-E-G-Nle-S-T-W-S-Aib-R-K-K(PEG$_2$-gE-gE-Palm)-NH$_2$ SEQ ID NO: 55
Ac-L-E-G-R-E-K-V-R-A-Q-I-Aib-Aib-E-G-Nle-S-T-W-S-Aib-R-K-K(PEG$_2$-gE-gE-gE-Palm)-NH$_2$ SEQ ID NO: 56
Ac-L-E-G-R-E-K-V-R-A-Q-I-Aib-Aib-E-G-Nle-S-T-W-S-Aib-R-K-K(PEG$_2$-PEG$_2$-gE-Stea)-NH$_2$ SEQ ID NO: 57
Ac-E-L-E-G-R-E-K-V-R-A-A-I-Aib-Aib-E-G-Nle-S-T-W-S-Aib-R-K-K(PEG$_2$-PEG$_2$-gE-gE-Palm)-NH$_2$ SEQ ID NO: 58
Ac-L-E-G-R-E-K-V-R-A-Q-I-Aib-Aib-E-G-Nle-S-T-W-S-Aib-R-K-K(PEG$_2$-PEG$_2$-gE-gE-gE-Palm)-NH$_2$ SEQ ID NO: 59
Ac-L-E-G-R-E-K-V-R-A-K(Ac)-I-Aib-Aib-E-G-Nle-S-T-W-S-Aib-R-K-K(PEG$_2$-PEG$_2$-gE-gE-Palm)-NH$_2$ SEQ ID NO: 60
Ac-L-E-G-R-E-K-V-R-A-K(Ac)-I-Aib-Aib-E-G-Nle-S-T-W-S-Aib-R-K-K-K(PEG$_2$-PEG$_2$-gE-gE-gE-Palm)-NH$_2$ SEQ ID NO: 61
Ac-L-E-G-R-E-K-V-R-A-K(Ac)-I-Aib-Aib-E-G-K(Ac)-S-T-W-S-Aib-R-K-K-K(PEG$_2$-PEG$_2$-gE-gE-gE-Palm)-NH$_2$ SEQ ID NO: 62
Ac-L-E-G-R-E-K-V-R-A-K(Ac)-I-Aib-Aib-E-G-Nle-S-T-W-S-Aib-R-K-K(Ac)-K(PEG$_2$-PEG$_2$-gE-gE-gE-Palm)-NH$_2$ SEQ ID NO: 63
Ac-L-E-G-R-E-K-V-R-A-K(Ac)-I-Aib-Aib-E-G-Nle-S-T-W-S-Aib-R-K-K(Ac)-K(PEG$_2$-PEG$_2$-PEG$_2$-gE-gE-gE-Palm)-NH$_2$ SEQ ID NO: 64
Ac-L-E-G-R-E-K-V-R-A-K(Ac)-I-Aib-Aib-E-G-Nle-S-T-W-S-Aib-R-K-K(Ac)-K(PEG$_2$-PEG$_2$-PEG$_2$-PEG$_2$-gE-gE-gE-Palm)-NH$_2$ SEQ ID NO: 65
Ac-L-E-G-R-E-K-V-R-A-K(Ac)-I-Aib-Aib-E-G-Nle-S-T-W-S-Mly-R-K-K(Ac)-K(PEG$_2$-PEG$_2$-PEG$_2$-gE-gE-gE-gE-Palm)-NH$_2$ SEQ ID NO: 66
Ac-L-E-G-R-E-K-V-R-A-K(Ac)-I-Aib-Aib-E-G-Nle-S-T-W-S-Aib-R-K-K(Ac)-K(PEG$_{12}$-gE-gE-gE-Palm)-NH$_2$ SEQ ID NO: 67
Ac-L-E-G-R-E-K-V-R-A-Q-I-Aib-Aib-E-G-Nle-S-T-W-S-Aib-R-K-K(PEG$_2$-PEG$_2$-gE-gE-gE-Stea)-NH$_2$

| Sequence listing |
|---|

SEQ ID NO: 68
Ac-L-E-G-R-E-K-V-R-A-Q-I-Aib-Aib-E-G-E-S-T-W-S-Aib-R-K-K-K(PEG$_2$-PEG$_2$-gE-gE-gE-Stea)-NH$_2$ SEQ ID NO: 69
Ac-L-E-G-R-E-K-V-R-Aib-Q-I-Aib-Aib-E-G-Nle-S-T-W-S-Aib-R-K-K-K(PEG$_2$-PEG$_2$-gE-gE-gE-Stea)-NH$_2$ SEQ ID NO: 70
Ac-L-E-G-R-E-K-V-R-A-Q-I-Aib-Aib-E-G-Q-S-T-W-S-Aib-R-K-K-K(PEG$_2$-PEG$_2$-gE-gE-gE-Stea)-NH$_2$ SEQ ID NO: 71
Ac-L-E-G-R-E-K-V-R-A-Q-I-Aib-Aib-E-G-Nle-S-T-W-S-Aib-R-K-K-K(PEG$_2$-PEG$_2$-gE-gE-gE-Stea)-NH$_2$ SEQ ID NO: 72
Ac-L-E-G-R-E-K-V-R-A-K(Ac)-I-Aib-Aib-E-G-Nle-S-T-W-S-Aib-R-K(Ac)-K-K(PEG$_2$-PEG$_2$-gE-gE-gE-Stea)-NH$_2$ SEQ ID NO: 73
Ac-L-E-G-R-E-K-V-R-A-K(Ac)-I-Aib-Aib-E-G-Nle-S-T-W-S-Aib-R-K-K-K(PEG$_2$-PEG$_2$-gE-gE-gE-Stea)-NH$_2$ SEQ ID NO: 74
Ac-L-E-G-R-E-K-V-R-A-Q-I-Aib-Aib-E-G-Nle-S-T-W-S-Aib-R-K-K-K(PEG$_2$-PEG$_2$-PEG$_2$-gE-gE-gE-Stea)-NH$_2$ SEQ ID NO: 75
Ac-L-E-G-R-E-K-V-R-A-Q-I-Aib-Aib-E-G-Nle-S-T-W-S-Aib-R-K-K-K(PEG$_2$-PEG$_2$-PEG$_2$-gE-gE-gE-Stea)-NH$_2$ SEQ ID NO: 76
Ac-L-E-G-R-E-K-V-R-A-Q-I-Aib-Aib-E-G-Nle-S-T-W-T-Aib-R-K-K-K(PEG$_2$-PEG$_2$-PEG$_2$-gE-gE-gE-Stea)-NH$_2$ SEQ ID NO: 77
Ac-L-E-G-R-E-K-V-R-L-Q-I-Aib-Aib-E-G-Nle-S-T-W-T-Aib-R-K-K-K(PEG$_2$-PEG$_2$-PEG$_2$-gE-gE-gE-Stea)-NH$_2$ SEQ ID NO: 78
Ac-L-E-G-R-E-K-V-R-A-K(Ac)-I-Aib-Aib-E-G-Nle-S-T-Y-S-Aib-R-K-K(Ac)-K(PEG$_2$-PEG$_2$-PEG$_2$-gE-gE-gE-Stea)-NH$_2$ SEQ ID NO: 79
Ac-L-E-G-R-E-K-V-R-A-K(Ac)-I-Aib-Aib-E-G-Nle-S-T-1Nal-S-Aib-R-K-K(PEG$_2$-PEG$_2$-PEG$_2$-gE-gE-gE-Stea)-NH$_2$ SEQ ID NO: 80
Ac-L-E-G-R-E-K-V-R-Aib-K(Ac)-I-Aib-Aib-E-G-Nle-S-T-1Nal-S-Aib-R-K-K(PEG$_2$-PEG$_2$-PEG$_2$-gE-gE-gE-Stea)-NH$_2$ SEQ ID NO: 81
Ac-L-E-G-R-E-K-V-R-A-K(Ac)-I-Aib-Aib-E-G-Nle-S-T-W-S-Aib-R-K-K(Ac)-K(PEG$_2$-PEG$_2$-PEG$_2$-gE-gE-gE-Stea)-NH$_2$ SEQ ID NO: 82
Ac-L-E-G-R-E-K-V-R-A-K(Ac)-I-Aib-Aib-E-G-Nle-S-T-W-S-Mly-R-K-K(Ac)-K(PEG$_2$-PEG$_2$-PEG$_2$-gE-gE-gE-Stea)-NH$_2$ SEQ ID NO: 83
Ac-L-E-G-R-E-K-V-R-A-K(Ac)-I-Aib-Aib-E-G-Nle-S-T-W-S-Aib-R-K-K-K(PEG$_2$-PEG$_2$-PEG$_2$-gE-gE-gE-Stea)-NH$_2$ SEQ ID NO: 84
Ac-L-E-G-R-E-K-V-R-A-K(Ac)-I-Aib-Aib-E-G-Nle-S-T-1Nal-S-Aib-R-K-K(Ac)-K(PEG$_2$-PEG$_2$-PEG$_2$-gE-gE-gE-Stea)-NH$_2$ SEQ ID NO: 85
Ac-L-E-G-R-E-K-V-R-Aib-K(Ac)-I-Aib-Aib-E-G-Nle-S-T-1Nal-S-Aib-R-K-K(Ac)-K(PEG$_2$-PEG$_2$-PEG$_2$-gE-gE-gE-Stea)-NH$_2$ SEQ ID NO: 86
Ac-L-E-G-R-E-K-V-R-A-K(Ac)-I-Aib-Aib-E-G-Nle-S-T-W-S-Aib-R-K-L-K(PEG$_2$-PEG$_2$-PEG$_2$-gE-gE-gE-Stea)-NH$_2$

| Sequence listing |
| --- |

SEQ ID NO: 87
Ac-L-E-G-R-E-K-V-R-A-K(Ac)-I-Aib-Aib-E-G-Nle-S-T-1Nal-S-Aib-R-K(Ac)-L-K(PEG$_2$-
PEG$_2$-PEG$_2$-gE-gE-Stea)-NH$_2$ SEQ ID NO: 88
Ac-L-E-G-R-E-K-V-R-A-Q-I-Aib-Aib-E-G-Nle-S-T-W-S-Aib-R-K-K-K(PEG$_2$-PEG$_2$-PEG$_2$-gE-
gE-gE-Stea)-NH$_2$ SEQ ID NO: 89
Ac-L-E-G-R-E-K-V-R-A-K(Ac)-I-Aib-Aib-E-G-Nle-S-T-W-S-Aib-R-K-K-K(PEG$_2$-PEG$_2$-
PEG$_2$-gE-gE-gE-Stea)-NH$_2$ SEQ ID NO: 90
Ac-L-E-G-R-E-K-V-R-A-K(Ac)-I-Aib-Aib-E-G-Nle-S-T-W-S-Aib-R-K-K(Ac)-K(PEG$_2$-PEG$_2$-
PEG$_2$-PEG$_2$-gE-gE-gE-Stea)-NH$_2$ SEQ ID NO: 91
Ac-L-E-G-R-E-K-V-R-A-K(Ac)-I-Aib-Aib-E-G-Nle-S-T-W-S-Aib-R-K-K-K(PEG$_2$-PEG$_2$-
PEG$_2$-PEG$_2$-gE-gE-gE-Stea)-NH$_2$ SEQ ID NO: 92
Ac-L-E-G-R-E-K-V-R-A-Q-I-Aib-Aib-E-G-Nle-S-T-W-S-Aib-R-K-K-K(PEG$_2$-PEG$_2$-PEG$_2$-
PEG$_2$-gE-gE-gE-Stea)-NH$_2$ SEQ ID NO: 93
Ac-L-E-G-R-E-K-V-R-A-Q-I-Aib-Aib-E-G-Nle-S-T-W-S-Aib-R-K-K-K(PEG$_2$-PEG$_2$-PEG$_2$-
PEG$_2$-PEG$_2$-gE-gE-gE-Stea)-NH$_2$ SEQ ID NO: 94
Ac-L-E-G-R-E-K-V-R-A-K(Ac)-I-Aib-Aib-E-G-Nle-S-T-W-S-Aib-R-K-K(Ac)-K(PEG$_2$DGA-
gE-gE-gE-Stea)-NH$_2$ SEQ ID NO: 95
Ac-L-E-G-R-E-K-V-R-A-K(Ac)-I-Aib-Aib-E-G-Nle-S-T-W-S-Aib-R-K-K(Ac)-K(PEG$_2$DGA-
PEG$_2$DGA-gE-gE-gE-Stea)-NH$_2$ SEQ ID NO: 96
Ac-L-E-G-R-E-K-V-R-A-K(Ac)-I-Aib-Aib-E-G-Nle-S-T-W-S-Aib-R-K-K(Ac)-K(PEG$_2$DGA-
PEG$_2$DGA-PEG$_2$DGA-gE-gE-gE-Stea)-NH$_2$ SEQ ID NO: 97
Ac-L-E-G-R-E-K-V-R-A-Q-I-Aib-Aib-E-G-Nle-S-T-W-S-Aib-R-K-K-K(PEG$_{12}$-gE-gE-gE-
Stea)-NH$_2$ SEQ ID NO: 98
Ac-L-E-G-R-E-K-V-R-A-Q-I-Aib-Aib-E-G-Nle-S-T-W-S-Aib-R-K-K-K(PEG$_2$-PEG$_2$-gE-gE-
gE-PEG$_2$-Stea)-NH$_2$ SEQ ID NO: 99
Ac-L-E-G-R-E-K-V-R-A-Q-I-Aib-Aib-E-G-Nle-S-T-W-S-Aib-R-K-K-K(PEG$_2$-PEG$_2$-gE-gE-
PEG$_2$-gE-Stea)-NH$_2$ SEQ ID NO: 100
Ac-L-E-G-R-E-K-V-R-A-Q-I-Aib-Aib-E-G-Nle-S-T-W-S-Aib-R-K-K-K(PEG$_2$-PEG$_2$-gE-gE-
PEG$_2$-gE-Stea)-NH$_2$ SEQ ID NO: 101
Ac-L-E-G-R-E-K-V-R-A-K(Ac)-I-Aib-Aib-E-G-Nle-S-T-W-S-Aib-R-K-K(Ac)-K(PEG$_2$-PEG$_2$-
gE-gE-PEG$_2$-gE-Stea)-NH$_2$ SEQ ID NO: 102
Ac-L-E-G-R-E-K-V-R-A-K(Ac)-I-Aib-Aib-E-G-Nle-S-T-W-S-Aib-R-K-K-K(PEG$_2$-PEG$_2$-gE-
gE-gE-PEG$_2$-gE-Stea)-NH$_2$ SEQ ID NO: 103
Ac-L-E-G-R-E-K-V-R-A-K(Ac)-I-Aib-Aib-E-G-Nle-S-T-1Nal-S-Aib-R-K-K-K(PEG$_2$-PEG$_2$-
gE-gE-gE-PEG$_2$-gE-Stea)-NH$_2$ SEQ ID NO: 104
Ac-L-E-G-R-E-K-V-R-A-Q-I-Aib-Aib-E-G-Nle-S-T-W-S-Aib-R-K-K-K(gE-gE-PEG$_2$-PEG$_2$-gE-
Stea)-NH$_2$ SEQ ID NO: 105
Ac-L-E-G-R-E-K-V-R-A-Q-I-Aib-Aib-E-G-Nle-S-T-W-S-Aib-R-K-K-K(gE-gE-PEG$_2$-PEG$_2$-
gE-Stea)-NH$_2$

Sequence listing

SEQ ID NO: 106
Ac-L-E-G-R-E-K-V-R-A-Q-I-Aib-Aib-E-G-Nle-S-T-W-S-Aib-R-K-K-K(gE-gE-PEG$_2$-PEG$_2$-PEG$_2$-gE-Stea)-NH$_2$ SEQ ID NO: 107
Ac-L-E-G-R-E-K-V-R-A-Q-I-Aib-Aib-E-G-Nle-S-T-W-S-Aib-R-K-K-K-PEG$_2$-PEG$_2$-PEG$_2$-gE-gE-K(gE-Palm)-NH$_2$ SEQ ID NO: 108
Ac-L-E-G-R-E-K-V-R-A-Q-I-Aib-Aib-E-G-Nle-S-T-W-S-Aib-R-K-K-K-PEG$_2$-PEG$_2$-PEG$_2$-PEG$_2$-gE-gE-gE-K(gE-Palm)-NH$_2$ SEQ ID NO: 109
Ac-L-E-G-R-E-K-V-R-A-Q-I-Aib-Aib-E-G-Nle-S-T-W-S-Aib-R-K-K-K-PEG$_2$-PEG$_2$-PEG$_2$-gE-gE-K(gE-Palm)-NH$_2$ SEQ ID NO: 110
Ac-L-E-G-R-E-K-V-R-A-Q-I-Aib-Aib-E-G-Nle-S-T-W-S-Aib-R-K-K-PEG$_2$-PEG$_2$-PEG$_2$-gE-gE-gE-K(gE-Palm)-NH$_2$ SEQ ID NO: 111
Ac-L-E-G-R-E-K-V-R-A-K(Ac)-I-Aib-Aib-E-G-Q-S-T-W-S-Aib-R-K-K-K(PEG$_2$-PEG$_2$-PEG$_2$-gE-gE-gE-gE-gE-Stea)-NH$_2$ SEQ ID NO: 112
Ac-L-E-G-R-E-K-V-R-A-K(Ac)-I-Aib-Aib-E-G-Nle-S-T-F-S-Aib-R-K-K(Ac)-K(PEG$_2$-PEG$_2$-PEG$_2$-gE-gE-gE-Stea)-NH$_2$ SEQ ID NO: 113
Ac-L-E-G-R-E-K-V-R-A-K(Ac)-I-Aib-Aib-E-G-Q-S-T-W-S-Aib-R-K-K(Ac)-K(PEG$_2$-PEG$_2$-PEG$_2$-gE-gE-gE-Stea)-NH$_2$ SEQ ID NO: 114
Ac-L-E-G-R-E-K-V-R-A-K(Ac)-I-Aib-Aib-E-G-Nle-S-T-W-S-Aib-R-K-K(Ac)-PEG$_2$-PEG$_2$-PEG$_2$-K(gE-gE-gE-Palm)-NH$_2$ SEQ ID NO: 115
Ac-L-E-G-R-E-K-V-R-A-K(Ac)-I-Aib-Aib-E-G-Q-S-T-W-S-Aib-R-K-K-K(PEG$_2$-PEG$_2$-PEG$_2$-gE-gE-gE-gE-Stea)-NH$_2$ SEQ ID NO: 116
Ac-L-E-G-R-E-K-V-R-A-K(Ac)-I-Aib-Aib-E-G-Nle-S-T-W-S-Aib-R-K-K(Ac)-PEG$_2$-PEG$_2$-PEG$_2$-PEG$_2$-gE-gE-K(gE-Palm)-NH$_2$ SEQ ID NO: 117
Ac-L-E-G-R-E-K-V-R-A-K(Ac)-I-Aib-Aib-E-G-Nle-S-T-W-S-Aib-R-K-K(Ac)-PEG$_2$-PEG$_2$-PEG$_2$-gE-gE-K(gE-Palm)-NH$_2$ SEQ ID NO: 118
Ac-L-E-G-R-E-K-V-R-A-Q-I-Aib-Aib-E-G-Nle-S-T-W-S-Aib-R-K-K(Ac)-PEG$_2$-PEG$_2$-gE-gE-K(gE-Palm)-NH$_2$ SEQ ID NO: 119
Ac-L-E-G-R-E-K-V-R-A-Q-I-Aib-Aib-E-G-Nle-S-T-W-S-Aib-R-K-K(Ac)-PEG$_2$-PEG$_2$-PEG$_2$-gE-gE-K(gE-Palm)-NH$_2$ SEQ ID NO: 120
Ac-L-E-G-R-E-K-V-R-A-K(Ac)-I-Aib-Aib-E-G-Nle-S-T-W-S-Aib-R-K-K(Ac)-K(PEG$_2$-PEG$_2$-PEG$_2$-gE-gE-gE-Lau)-NH$_2$ SEQ ID NO: 121
Ac-L-E-G-R-E-K-V-R-A-Q-I-Aib-Aib-E-G-Nle-S-T-W-S-Aib-R-K-K(Ac)-PEG$_2$-PEG$_2$-PEG$_2$-PEG$_2$-gE-gE-K(gE-Palm)-NH$_2$ SEQ ID NO: 122
Ac-L-E-G-R-E-K-V-R-A-Q-I-Aib-Aib-E-G-Nle-S-T-W-S-Aib-R-K-K-K-PEG$_4$-PEG$_4$-K(gE-gE-gE-gE-Stea)-NH$_2$ SEQ ID NO: 123
Ac-L-E-G-R-E-K-V-R-A-K(Ac)-I-Aib-Aib-E-G-Nle-S-T-W-S-Aib-R-K-K(Ac)-PEG$_4$-K(gE-gE-gE-Stea)-NH$_2$ SEQ ID NO: 124
Ac-L-E-G-R-E-K-V-R-A-K(Ac)-I-Aib-Aib-E-G-Nle-S-T-W-S-Aib-R-K-K(Ac)-PEG$_4$-PEG$_4$-K(gE-gE-gE-Stea)-NH$_2$

| Sequence listing |
|---|

SEQ ID NO: 125
Ac-L-E-G-R-E-K-V-R-A-K(Ac)-I-Aib-Aib-E-G-Nle-S-T-Mtr-S-Mly-R-K-K(Ac)-PEG$_2$-PEG$_2$-PEG$_2$-K(gE-gE-gE-gE-Palm)-NH$_2$ SEQ ID NO: 126
Ac-L-E-G-R-E-K-V-R-A-K(Ac)-I-Aib-Aib-E-G-Nle-S-T-W-S-Aib-Cit-A-K(Ac)-K(PEG$_2$-PEG$_2$-PEG$_2$-gE-gE-gE-Stea)-NH$_2$ SEQ ID NO: 127
Ac-L-E-G-R-E-K-V-R-A-K(Ac)-I-Aib-Aib-E-G-Nle-S-T-W-S-Aib-R-K-L-K(PEG$_2$-PEG$_2$-PEG$_2$-gE-gE-gE-Stea)-NH$_2$ SEQ ID NO: 128
Ac-L-E-G-R-E-K-V-R-A-K(Ac)-I-Aib-Aib-E-G-Nle-S-T-W-S-Aib-R-K-K(Ac)-K(PEG$_2$-PEG$_2$-PEG$_2$-gE-gE-gE-gE-Stea)-NH$_2$ SEQ ID NO: 129
Ac-L-E-G-R-E-K-V-R-A-K(Ac)-I-Aib-Aib-E-G-Nle-S-T-W-S-Mly-Cit-K-K(Ac)-K(PEG$_2$-PEG$_2$-PEG$_2$-gE-gE-gE-Stea)-NH$_2$ SEQ ID NO: 130
Ac-L-E-G-R-E-K-V-R-A-K(Ac)-I-Aib-Aib-E-G-Nle-S-T-W-S-Aib-R-K-K(Ac)-K(PEG$_2$-PEG$_2$-PEG$_2$-PEG$_2$-gE-gE-gE-gE-Palm)-NH$_2$ SEQ ID NO: 131
Ac-L-E-G-R-E-K-V-R-A-K(Ac)-I-Aib-Aib-E-G-Nle-S-T-W-S-Mly-R-K-K(Ac)-PEG$_2$-PEG$_2$-PEG$_2$-PEG$_2$-K(gE-gE-gE-gE-Palm)-NH$_2$ SEQ ID NO: 132
Ac-L-E-G-R-E-K-V-R-A-K(Ac)-I-Aib-Aib-E-G-Nle-S-T-W-S-Mly-Cit-A-K(Ac)-K(PEG$_2$-PEG$_2$-PEG$_2$-PEG$_2$-gE-gE-gE-Stea)-NH$_2$ SEQ ID NO: 133
Ac-L-E-G-R-E-K-V-R-A-K(Ac)-I-Aib-Aib-E-G-Nle-S-T-W-S-Aib-Rme-K-K(Ac)-K(PEG$_2$-PEG$_2$-PEG$_2$-gE-gE-gE-Stea)-NH$_2$ SEQ ID NO: 134
Ac-L-E-G-R-E-K-V-R-A-K(Ac)-I-Aib-Aib-E-G-Nle-S-T-W-S-Aib-R-Tml-K(Ac)-K(PEG$_2$-PEG$_2$-PEG$_2$-gE-gE-gE-Stea)-NH$_2$ SEQ ID NO: 135
Ac-L-E-G-R-E-K-V-R-A-K(Ac)-I-Aib-Aib-E-G-Nle-S-T-W-S-Mly-R-A-K(Ac)-K(PEG$_2$-PEG$_2$-PEG$_2$-gE-gE-gE-Stea)-NH$_2$ SEQ ID NO: 136
Ac-L-E-G-R-E-K-V-R-A-K(Ac)-I-Aib-Aib-E-G-Nle-S-T-W-S-Mly-R-K-K(Ac)-PEG$_2$-PEG$_2$-PEG$_2$-PEG$_2$-gE-gE-gE-K(gE-Palm)-NH$_2$ SEQ ID NO: 137
Ac-L-E-G-R-E-K-V-R-A-K(Ac)-I-Aib-Aib-E-G-Nle-S-T-W-S-Aib-Rme-Tml-K(Ac)-K(PEG$_2$-PEG$_2$-PEG$_2$-gE-gE-gE-Stea)-NH$_2$ SEQ ID NO: 138
Ac-L-E-G-R-E-K-V-R-A-K(Ac)-I-Aib-Aib-E-G-Nle-S-T-W-S-Mly-Rme-Tml-K(Ac)-K(PEG$_2$-PEG$_2$-PEG$_2$-gE-gE-gE-Stea)-NH$_2$ SEQ ID NO: 139
Ac-L-E-G-R-E-K-V-R-A-K(Ac)-I-Aib-Aib-E-G-Nle-S-T-F-S-Mly-A-A-K(Ac)-PEG$_2$-PEG$_2$-PEG$_2$-PEG$_2$-gE-gE-gE-K(gE-Palm)-NH$_2$ SEQ ID NO: 140
Ac-L-E-G-R-E-K-V-R-A-K(Ac)-I-Aib-Aib-E-G-Nle-S-T-F-S-Mly-R-K-K(Ac)-K(PEG$_2$-PEG$_2$-PEG$_2$-gE-gE-gE-gE-Palm)-NH$_2$ SEQ ID NO: 141
Ac-L-E-G-R-E-K-V-R-A-K(Ac)-I-Aib-Aib-E-G-Nle-S-T-W-S-Mly-Rme-Tml-K(Ac)-K(PEG$_2$-PEG$_2$-PEG$_2$-gE-gE-gE-gE-Palm)-NH$_2$ SEQ ID NO: 142
Ac-L-E-G-R-E-K-V-R-A-K(Ac)-I-Aib-Aib-E-G-Nle-S-T-F-S-Mly-R-K-K(Ac)-TTDS-TTDS-K(gE-gE-gE-gE-Palm)-NH$_2$ SEQ ID NO: 143
Ac-L-E-G-R-E-K-V-R-A-K(Ac)-I-Aib-Aib-E-G-Nle-S-T-F-S-Mly-R-K-K(Ac)-PEG$_2$-PEG$_2$-PEG$_2$-PEG$_2$-K(gE-gE-gE-gE-Palm)-NH$_2$

```
                          Sequence listing

SEQ ID NO: 144
Ac-L-E-G-R-E-K-V-R-A-K(Ac)-I-Aib-Aib-E-G-Nle-S-T-F-S-Aib-R-K-K(Ac)-PEG2-PEG2-
PEG2-PEG2-K(gE-gE-gE-Palm)-NH2

SEQ ID NO: 145
Ac-L-E-G-R-E-K-V-R-A-K(Ac)-I-Aib-Aib-E-G-Nle-S-T-F-S-Mly-R-K-K(Ac)-PEG2-PEG2-
PEG2-PEG2-gE-gE-gE-K(gE-Palm)-NH2

SEQ ID NO: 146
Ac-L-E-G-R-E-K-V-R-A-K(Ac)-I-Aib-Aib-E-G-Nle-S-T-F-S-Mly-R-K-K(Ac)-TTDS-TTDS-
gE-gE-gE-K(gE-Palm)-NH2

SEQ ID NO: 147
Ac-L-E-G-R-E-K-V-R-A-K(Ac)-I-Aib-Aib-E-G-Nle-S-T-F-S-Aib-R-K-K(Ac)-K(PEG2-PEG2-
PEG2-PEG2-gE-gE-gE-gE-Palm)-NH2

SEQ ID NO: 148
Ac-L-E-G-R-E-K-V-R-A-K(Ac)-I-Aib-Aib-E-G-Nle-S-T-W-S-Aib-Rds-K-K(Ac)-K(PEG2-
PEG2-PEG2-gE-gE-gE-Stea)-NH2

SEQ ID NO: 149
Ac-L-E-G-R-E-K-V-R-A-K(Ac)-I-Aib-Aib-E-G-Nle-S-T-F-S-Mly-R-A-K(Ac)-PEG2-PEG2-
PEG2-PEG2-gE-gE-gE-K(gE-Palm)-NH2

SEQ ID NO: 150
Ac-L-E-G-R-E-K-V-R-A-K(Ac)-I-Aib-Aib-E-G-Nle-S-T-F-S-Mly-R-A-K(Ac)-PEG2-PEG2-
PEG2-PEG2-K(gE-gE-gE-gE-Palm)-NH2

SEQ ID NO: 151
Ac-L-E-G-R-E-K-V-R-A-K(Ac)-I-Aib-Aib-E-G-Nle-S-T-F-S-Mly-Rme-A-K(Ac)-PEG2-PEG2-
PEG2-PEG2-gE-gE-gE-K(gE-Palm)-NH2

SEQ ID NO: 152
Ac-L-E-G-R-E-K-V-R-A-K(Ac)-I-Aib-Aib-E-G-Nle-S-T-Mph-S-Mly-R-A-K(Ac)-PEG2-PEG2-
PEG2-PEG2-gE-gE-gE-K(gE-Palm)-NH2

SEQ ID NO: 153
Ac-L-E-G-R-E-K-V-R-A-K(Ac)-I-Aib-Aib-E-G-Nle-S-T-F-S-Aib-R-K-K(Ac)-K(PEG2-PEG2-
PEG2-PEG2-gE-gE-gE-Palm)-NH2

SEQ ID NO: 154
Ac-L-E-G-R-E-K-V-R-A-K(Ac)-I-Aib-Aib-E-G-Nle-S-T-F-S-Mly-R-A-K(Ac)-K(PEG2-PEG2-
PEG2-PEG2-gE-gE-gE-gE-Palm)-NH2

SEQ ID NO: 155
Ac-L-E-G-R-E-K-V-R-A-K(Ac)-I-Aib-Aib-E-G-Nle-S-T-W-S-Aib-A-A-K(Ac)-K(PEG2-PEG2-
PEG2-gE-gE-gE-Stea)-NH2

SEQ ID NO: 156
Ac-L-E-G-R-E-K-V-R-A-K(Ac)-I-Aib-Aib-E-G-Nle-S-T-W-S-Aib-A-A-K(Ac)-K(PEG2DGA-
PEG2DGA-gE-gE-gE-Stea)-NH2

SEQ ID NO: 157
Ac-L-E-G-R-E-K-V-R-A-K(Ac)-I-Aib-Aib-E-G-Nle-S-T-F-S-Mly-R-A-K(Ac)-TTDS-TTDS-
gE-gE-gE-K(gE-Palm)-NH2

SEQ ID NO: 158
Ac-L-E-G-R-E-K-V-R-A-K(Ac)-I-Aib-Aib-E-G-Nle-S-T-Wox-S-Aib-R-K-K(Ac)-K(PEG2-
PEG2-PEG2-gE-gE-gE-Stea)-NH2

SEQ ID NO: 159
Ac-L-E-G-R-E-K-V-R-A-K(Ac)-I-Aib-Aib-E-G-Nle-S-T-F-S-Mly-R-K-K(Ac)-PEG2-PEG2-
PEG2-PEG2-gE-gE-K(gE-Palm)-NH2

SEQ ID NO: 160
Ac-L-E-G-R-E-K-V-R-A-K(Ac)-I-Aib-Aib-E-G-Nle-S-T-F-S-Mly-R-A-K(Ac)-PEG2-PEG2-
PEG2-PEG2-gE-gE-K(gE-Palm)-NH2

SEQ ID NO: 161
Ac-L-E-G-R-E-K-V-R-A-K(Ac)-I-Aib-Aib-E-G-Q-S-T-F-S-Mly-R-A-K(Ac)-PEG2-PEG2-
PEG2-PEG2-K(gE-gE-gE-gE-Lau)-NH2

SEQ ID NO: 162
Ac-L-E-G-R-E-K-V-R-A-K(Ac)-I-Aib-Aib-E-G-Nle-S-T-F-S-Mly-R-A-K(Ac)-TTDS-TTDS-
K(gE-gE-gE-gE-Palm)-NH2
```

| Sequence listing |
| --- |

SEQ ID NO: 163
Ac-L-E-G-R-E-K-V-R-A-K(Ac)-I-Aib-Aib-E-G-Nle-S-T-W-S-Aib-R-K-K(Ac)-K(PEG$_2$-PEG$_2$-PEG$_2$-gE-gE-gE-Penta)-NH$_2$ SEQ ID NO: 164
Ac-L-E-G-R-E-K-V-R-A-K(Ac)-I-Aib-Aib-E-G-Nle-S-T-W-S-Aib-R-K-K(Ac)-K(PEG$_2$-PEG$_2$-PEG$_2$-gE-gE-gE-Hepta)-NH$_2$ SEQ ID NO: 165
Ac-L-E-G-R-E-K-V-R-A-K(Ac)-I-Aib-Aib-E-G-Nle-S-T-W-S-Aib-R-K-K(Ac)-K(PEG$_2$-PEG$_2$-gE-gE-PEG$_2$-gE-Palm)-NH$_2$ SEQ ID NO: 166
Ac-L-E-G-R-E-K-V-R-A-K(Ac)-I-Aib-Aib-E-G-Nle-S-T-W-S-Aib-R-K-K(Ac)-K(TTDS-TTDS-gE-gE-gE-Palm)-NH$_2$ SEQ ID NO: 167
Ac-L-E-G-R-E-K-V-R-A-K(Ac)-I-Aib-Aib-E-G-Nle-S-T-F-S-Mly-R-A-K(Ac)-PEG$_2$-PEG$_2$-PEG$_2$-PEG$_2$-K(gE-gE-gE-Penta)-NH$_2$ SEQ ID NO: 168
Ac-L-E-G-R-E-K-V-R-A-K(Ac)-I-Aib-Aib-E-G-Nle-S-T-F-S-Mly-R-A-K(Ac)-PEG$_2$-PEG$_2$-PEG$_2$-PEG$_2$-gE-gE-K(gE-gE-Penta)-NH$_2$ SEQ ID NO: 169
Ac-L-E-G-R-E-K-V-R-A-K(Ac)-I-Aib-Aib-E-G-Nle-S-T-F-S-Mly-R-A-K(Ac)-TTDS-TTDS-TTDS-gE-gE-K(gE-gE-Palm)-NH$_2$ SEQ ID NO: 170
Ac-L-E-G-R-E-K-V-R-A-K(Ac)-I-Aib-Aib-E-G-Q-S-T-F-S-Mly-R-A-K(Ac)-PEG$_2$-PEG$_2$-PEG$_2$-PEG$_2$-K(gE-gE-gE-gE-Palm)-NH$_2$ SEQ ID NO: 171
Ac-L-E-G-R-E-K-V-R-A-K(Ac)-I-Aib-Aib-E-G-Nle-S-T-W-S-Aib-R-K-K(Ac)-K(PEG$_2$-PEG$_2$-PEG-gE-gE-gE-Eico)-NH$_2$ SEQ ID NO: 172
Ac-L-E-G-R-E-K-V-R-A-K(Ac)-I-Aib-Aib-E-G-Nle-S-T-F-S-Mly-R-A-K(Ac)-PEG$_2$-PEG$_2$-PEG$_2$-PEG$_2$-K(gE-gE-gE-gE-Myr)-NH$_2$ SEQ ID NO: 173
Ac-L-E-G-R-E-K-V-R-A-K(Ac)-I-Aib-Aib-E-G-Nle-S-T-W-S-Aib-R-K-K(Ac)-K((PEG$_2$-PEG$_2$-PEG$_2$-gE-gE-gE-Doco)-NH$_2$ SEQ ID NO: 174
Ac-L-E-G-R-E-K-V-R-A-Q-I-Aib-Aib-E-G-Nle-S-T-W-S-Aib-R-K-K-K(PEG$_2$-PEG$_2$-PEG$_2$-gE-gE-gE-Stea)-NH$_2$ SEQ ID NO: 175
Ac-L-E-G-R-E-K-V-R-A-K(Ac)-I-Aib-Aib-E-G-Nle-S-T-W-S-Aib-R-K-K(Ac)-PEG$_2$DGA-K(gE-gE-gE-Palm)-NH$_2$ SEQ ID NO: 176
Ac-L-E-G-R-E-K-V-R-A-K(Ac)-I-Aib-Aib-E-G-Q-S-T-W-S-Aib-R-K-K(Ac)-PEG$_2$DGA-K(gE-gE-gE-Palm)-NH$_2$ SEQ ID NO: 177
Ac-L-E-G-R-E-K-V-R-A-Q-I-Aib-Aib-E-G-Q-S-T-W-S-Aib-R-K-K(Ac)-PEG$_2$DGA-PEG$_2$DGA-K(gE-gE-gE-Palm)-NH$_2$ SEQ ID NO: 178
Ac-L-E-G-R-E-K-V-R-A-K(Ac)-I-Aib-Aib-E-G-Nle-S-T-W-S-Aib-R-K-K(Ac)-K(PEG$_2$-PEG$_2$-PEG$_2$-gE-gE-gE-Myr)-NH$_2$ SEQ ID NO: 179
Ac-L-E-G-R-E-K-V-R-A-K(Ac)-I-Aib-Aib-E-G-Q-S-T-Y-S-Aib-R-K-K(Ac)-PEG$_2$-PEG$_2$-PEG$_2$-K(gE-gE-gE-Palm)-NH$_2$ SEQ ID NO: 180
Ac-L-E-G-R-E-K-V-R-A-K(Ac)-I-Aib-Aib-E-G-Q-S-T-W-S-Aib-R-K-K(Ac)-K(PEG$_2$-PEG$_2$-PEG$_2$-PEG$_2$-gE-gE-gE-gE-Stea)-NH$_2$ SEQ ID NO: 181
Ac-L-E-G-R-E-K-V-R-A-K(Ac)-I-Aib-Aib-E-G-Nle-S-T-W-S-Aib-R-K-K(Ac)-PEG$_8$-K(gE-gE-gE-Palm)-NH$_2$

Sequence listing

SEQ ID NO: 182
Ac-L-E-G-R-E-K-V-R-A-K(Ac)-I-Aib-Aib-E-G-Q-S-T-F-S-Mly-R-A-K(Ac)-PEG$_2$-PEG$_2$-PEG$_2$-PEG$_2$-K(gE-gE-gE-gE-Penta)-NH$_2$ SEQ ID NO: 183
Ac-L-E-G-R-E-K-V-R-A-K(Ac)-I-Aib-Aib-E-G-Nle-S-T-F-S-Mly-R-A-K(Ac)-K(TTDS-TTDS-TTDS-gE-gE-gE-Palm)-NH$_2$ SEQ ID NO: 184
Ac-L-E-G-R-E-K-V-R-A-K(Ac)-I-Aib-Aib-E-G-Q-S-T-F-S-Mly-R-A-K(Ac)-TTDS-TTDS-TTDS-gE-gE-K(gE-gE-Penta)-NH$_2$ SEQ ID NO: 185
Ac-L-E-G-R-E-K-V-R-A-K(Ac)-I-Aib-Aib-E-G-Q-S-T-F-S-Mly-R-A-K(Ac)-PEG$_2$-PEG$_2$-PEG$_2$-PEG$_2$-gE-gE-K(gE-gE-Palm)-NH$_2$ SEQ ID NO: 186
Ac-L-E-G-R-E-K-V-R-A-K(Ac)-I-Aib-Aib-E-G-Q-S-T-F-S-Mly-R-A-K(Ac)-PEG$_2$-PEG$_2$-PEG$_2$-PEG$_2$-gE-gE-K(gE-gE-Penta)-NH$_2$ SEQ ID NO: 187
Ac-L-E-G-R-E-K-V-R-A-K(Ac)-I-Aib-Aib-E-G-Nle-S-T-F-S-Mly-R-A-K(Ac)-TTDS-TTDS-TTDS-K(gE-gE-gE-Palm)-NH$_2$ SEQ ID NO: 188
Ac-L-E-G-R-E-K-V-R-A-K(Ac)-I-Aib-Aib-E-G-Nle-S-T-F-S-Mly-R-A-K(Ac)-TTDS-TTDS-TTDS-K(gE-gE-gE-Penta)-NH$_2$ SEQ ID NO: 189
Ac-L-E-G-R-E-K-V-R-A-K(Ac)-I-Aib-Aib-E-G-Q-S-T-F-S-Mly-R-A-K(Ac)-K(TTDS-TTDS-TTDS-gE-gE-gE-Penta)-NH$_2$ SEQ ID NO: 190
Ac-L-E-G-R-E-K-V-R-A-K(Ac)-I-Aib-Aib-E-G-Q-S-T-F-S-Mly-R-A-K(Ac)-PEG$_2$-PEG$_2$-PEG$_2$-PEG$_2$-K(gE-gE-gE-gE-Myr)-NH$_2$ SEQ ID NO: 191
Ac-L-E-G-R-E-K-V-R-A-K(Ac)-I-Aib-Aib-E-G-Q-S-T-F-S-Mly-R-A-K(Ac)-K(PEG$_2$-PEG$_2$-PEG$_2$-PEG$_2$-gE-gE-gE-Palm)-NH$_2$ SEQ ID NO: 192
Ac-L-E-G-R-E-K-V-R-A-K(Ac)-I-Aib-Aib-E-G-Nle-S-T-F-S-Mly-R-A-K(Ac)-PEG$_2$-PEG$_2$-PEG$_2$-PEG$_2$-K(gE-gE-gE-Palm)-NH$_2$ SEQ ID NO: 193
Ac-L-E-G-R-E-K-V-R-A-K(Ac)-I-Aib-Aib-E-G-Nle-S-T-F-S-Mly-R-A-K(Ac)-TTDS-TTDS-TTDS-gE-gE-gE-K(gE-Palm)-NH$_2$ SEQ ID NO: 194 = H2-relaxin chain A
H-Gln-Leu-Tyr-Ser-Ala-Leu-Ala-Asn-Lys-Cys-Cys-His-Val-Gly-Cys-Thr-Lys-Arg-Ser-Leu-Ala-Arg-Phe-Cys-OH SEQ ID NO: 195 = H2-relaxin chain B
H-Asp-Ser-Trp-Met-Glu-Glu-Val-Ile-Lys-Leu-Cys-Gly-Arg-Glu-Leu-Val-Arg-Ala-Gln-Ile-Ala-Ile-Cys-Gly-Met-Ser-Thr-Trp-Ser-OH SEQ ID NO: 196 = SEQ ID B7-33 C11.23S*
H-Val-Ile-Lys-Leu-Ser-Gly-Arg-Glu-Leu-Val-Arg-Ala-Gln-Ile-Ala-Ile-Ser-Gly-Met-Ser-Thr-Trp-Ser-Lys-Arg-Ser-Leu-NH$_2$ SEQ ID NO: 197 = SEQ ID AcB7-33 C11.23S*
Ac-Val-Ile-Lys-Leu-Ser-Gly-Arg-Glu-Leu-Val-Arg-Ala-Gln-Ile-Ala-Ile-Ser-Gly-Met-Ser-Thr-Trp-Ser-Lys-Arg-Ser-Leu-NH$_2$ SEQ ID NO: 198 = SEQ ID KKKK(AcB7-29 C11.23S)*
Ac-Val-Ile-Lys-Leu-Ser-Gly-Arg-Glu-Leu-Val-Arg-Ala-Gln-Ile-Ala-Ile-Ser-Gly-Met-Ser-Thr-Trp-Ser-Lys-Lys-Lys-Lys-NH$_2$

*comparison examples

The invention claimed is:

1. A peptide having the following formula (I):

$N_{ter}$-Ac-$(E)_a$-$X_{10}$-E-G-R-E-$X_{15}$-V-R-$X_{18}$-$X_{19}$-I-$X_{21}$-$X_{22}$-E-G-$X_{25}$-S-$X_{27}$-$X_{28}$-$X_{29}$-$X_{30}$-R-$(X_{32})_b$-$(X_{33})_c$-$(K)_d$-$(X_{35})_e$-$(gE)_f$-$X_{37}$-$C_{ter}$;

wherein:

$N_{ter}$ represents the N-terminal end of the peptide;
$C_{ter}$ represents the C-terminal end of the peptide;
a, b, c and d independently represent 0 or 1;
e and f independently represents 0, 1, 2, 3 or 4;
Ac represents acetyl group;
E represents glutamic acid;
$X_{10}$ represents an amino acid selected from the group consisting of leucine, 2-amino-isobutyric acid, Nε-acetyl-lysine and α-methyl-leucine;
G represents glycine;
R represents arginine;
$X_{15}$ represents an amino acid selected from the group consisting of lysine, homolysine, arginine, homoarginine and ornithine;
V represents valine;
$X_{18}$ represents an amino acid selected from the group consisting of alanine, 2-amino-isobutyric acid, leucine, Nε-acetyl-lysine, and glutamine;
$X_{19}$ represents an amino acid selected from the group consisting of glutamine, Nε-acetyl-lysine, citruline, alanine and 2-amino-isobutyric acid;

I represents isoleucine;

$X_{21}$ represents an amino acid selected from the group consisting of alanine and 2-amino-isobutyric acid;

$X_{22}$ represents an amino acid selected from the group consisting of isoleucine and 2-amino-isobutyric acid;

$X_{25}$ represents an amino acid selected from the group consisting of methionine, norleucine, leucine, alanine, glutamine, Nε-acetyl-lysine and glutamic acid;

S represents serine;

$X_{27}$ represents an amino acid selected from the group consisting of threonine, lysine, arginine and glutamine;

$X_{28}$ represents an amino acid selected from the group consisting of tryptophan, 5-fluoro-tryptophan, 5-chloro-tryptophan, 5-methoxy-tryptophan, tyrosine, phenylalanine, 4-fluoro-phenylalanine, 1-naphtylalanine, 2-naphtylalanine, α-methyl-tryptophane, α-methyl-phenylalanine and 5-hydroxy-tryptophane;

$X_{29}$ represents an amino acid selected from the group consisting of serine, threonine, α-methyl-serine, Nε-acetyl-lysine and valine;

$X_{30}$ represents an amino acid selected from the group consisting of lysine, 2-amino-isobutyric acid, α-methyl-lysine, arginine and α-methyl-arginine;

$X_{31}$ represents an amino acid selected from the group consisting of arginine, Nω-methyl-arginine, alanine, Nω,Nω'-dimethyl-arginine and citruline;

$X_{32}$ represents an amino acid selected from the group consisting of lysine, Nε-acetyl-lysine, arginine, alanine and Nε,Nε,Nε-tri-methyl-lysine;

$X_{33}$ represents an amino acid selected from the group consisting of leucine, lysine, Nε-acetyl-lysine, alanine and arginine;

K represents lysine;

$X_{35}$ represents a polyethylene glycol derivative selected from the group consisting of $PEG_2$, $PEG_4$, $PEG_8$, $PEG_2DGA$, TTDS, $PEG_{12}$, $PEG_{24}$ and $PEG_8$;

gE represents gamma-glutamic acid; and $X_{37}$ represents the following structure:

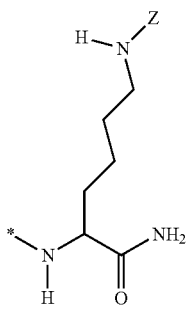

in which:
- -* represents a covalent bond: with $(gE)_f$ when f is different from 0; with $(X_{35})_e$ when f is 0 and e is different from 0; with $(K)_d$ when e and f are 0 and d is 1; with $(X_{33})_c$ when d, e and f are 0 and c is 1; with $(X_{32})_b$ when c, d, e and f are 0 and b is 1; or with $X_{31}$ when b, c, d, e and f all are 0; and Z represents a group of formula (II):

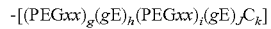

in which:
g and i independently represent 0, 1, 2, 3, 4 or 5;
h and j independently represent 0, 1, 2, 3, 4 or 5;

PEGxx independently represents a polyethylene glycol derivative selected from the group consisting of $PEG_2$, $PEG_2DGA$, TTDS and $PEG_{12}$; and $C_k$ represents a linear saturated $C_{12}$—$C_{22}$ acyl group;

or a salt or solvate thereof.

2. The peptide according to claim 1 having the following formula (Ia):

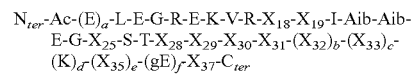

wherein:

$N_{ter}$ represents the N-terminal end of the peptide;

$C_{ter}$ represents the C-terminal end of the peptide;

a, b, c and d independently represent 0 or 1;

e represents 0, 1, 2, 3 or 4;

f represents 0, 2 or 3;

Ac represents acetyl group;

E represents glutamic acid;

L represents leucine;

G represents glycine;

R represents arginine;

K represents lysine;

V represents valine;

$X_{18}$ represents an amino acid selected from the group consisting of alanine, 2-amino-isobutyric acid and leucine;

$X_{19}$ represents an amino acid selected from the group consisting of glutamine, Nε-acetyl-lysine and alanine;

I represents isoleucine;

Aib represents 2-amino-isobutyric acid;

$X_{25}$ represents an amino acid selected from the group consisting of methionine, norleucine, glutamine, Nε-acetyl-lysine and glutamic acid;

S represents serine;

T represents threonine;

$X_{28}$ represents an amino acid selected from the group consisting of tryptophan, 1-naphtylalanine, phenylalanine, tyrosine, α-methyl-tryptophane, α-methyl-phenylalanine and 5-hydroxy-tryptophane;

$X_{29}$ represents an amino acid selected from the group consisting of serine, threonine and α-methyl-serine;

$X_{30}$ represents an amino acid selected from the group consisting of lysine, 2-amino-isobutyric acid and α-methyl-lysine;

$X_{31}$ represents an amino acid selected from the group consisting of arginine, Nω-methyl-arginine, alanine, Nω,Nω'-dimethyl-arginine and citruline;

$X_{32}$ represents an amino acid selected from the group consisting of lysine, alanine, Nε-acetyl-lysine and Nε,Nε,Nε-tri-methyl-lysine;

$X_{33}$ represents an amino acid selected from the group consisting of leucine, lysine and Nε-acetyl-lysine;

$X_{35}$ represents a polyethylene glycol derivative selected from the group consisting of $PEG_2$, $PEG_4$, $PEG_8$, $PEG_2DGA$, TTDS, $PEG_{12}$, $PEG_{24}$ and $PEG_{28}$;

gE represents gamma-glutamic acid; and $X_{37}$ represents the following structure:

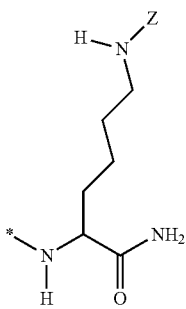

in which:

-* is as defined in claim 1; and

Z is selected from the group consisting of a -palmitoyl (-Palm), -gamma glutamic acid-palmitoyl (-gE-Palm), -gamma glutamic acid-stearoyl (-gE-Stea), -(gamma glutamic acid)$_2$-palmitoyl (-(gE)$_2$-Palm), -(gamma glutamic acid)$_3$-palmitoyl (-(gE)$_3$-Palm), -(gamma glutamic acid)$_3$-stearoyl (-(gE)$_3$-Stea), -(gamma glutamic acid)$_4$-stearoyl (-(gE)$_4$-Stea), -(gamma glutamic acid)$_4$-plamitoyl (-(gE)$_4$-Palm), -stearoyl (-stea), -PEG$_2$-Palmitoyl (-PEG$_2$-Palm), -(PEG$_2$)$_2$-Stearoyl (-(PEG$_2$)$_2$-Stea), -(PEG$_2$)$_3$-Stearoyl (-(PEG$_2$)$_3$-Stea), -PEG$_2$-(gamma glutamic acid)-Palmitoyl (-PEG$_2$-gE-Palm), -PEG$_2$-(gamma glutamic acid)$_2$-Palmitoyl (-PEG$_2$-(gE)$_2$-Palm), -PEG$_2$-(gamma glutamic acid)$_3$-Palmitoyl (-PEG$_2$-(gE)$_3$-Palm), -(PEG$_2$)$_2$-(gamma glutamic acid)-Stearoyl (-(PEG$_2$)$_2$-gE-Stea), -(PEG$_2$)$_2$-(gamma glutamic acid)$_2$-Palmitoyl (-(PEG$_2$)$_2$-(gE)$_2$-Palm), -(PEG$_2$)$_2$-(gamma glutamic acid)$_3$-Palmitoyl (-(PEG$_2$)$_2$-(gE)$_3$-Palm), -(PEG$_2$)$_3$-(gamma glutamic acid)$_3$-Palmitoyl (-(PEG$_2$)$_3$-(gE)$_3$-Palm), -(PEG$_2$)$_4$-(gamma glutamic acid)$_3$-Palmitoyl (-(PEG$_2$)$_4$-(gE)$_3$-Palm), -(PEG$_2$)$_3$-(gamma glutamic acid)$_4$-Palmitoyl (-(PEG$_2$)$_3$-(gE)$_4$-Palm), -PEG$_{12}$-(gamma glutamic acid)$_3$-Palmitoyl (-PEG$_{12}$-(gE)$_3$-Palm), -(PEG$_2$)$_2$-(gamma glutamic acid)$_3$-Stearoyl (-(PEG$_2$)$_2$-(gE)$_3$-Stea), -(PEG$_2$)$_3$-(gamma glutamic acid)$_3$-Stearoyl (-(PEG$_2$)$_3$-(gE)$_3$-Stea), -(PEG$_2$)$_3$-(gamma glutamic acid)$_4$-Stearoyl (-(PEG$_2$)$_3$-(gE)$_4$-Stea), -(PEG$_2$)$_4$-(gamma glutamic acid)$_3$-Stearoyl (-(PEG$_2$)$_4$-(gE)$_3$-Stea), -(PEG$_2$)$_5$-(gamma glutamic acid)$_3$-Stearoyl (-(PEG$_2$)$_5$-(gE)$_3$-Stea), -(PEG$_2$DGA)-(gamma glutamic acid)$_3$-Stearoyl (-(PEG$_2$DGA)-(gE)$_3$-Stea), -(PEG$_2$DGA)$_2$-(gamma glutamic acid)$_3$-Stearoyl (-(PEG$_2$DGA)$_2$-(gE)$_3$-Stea), -(PEG$_2$DGA)$_3$-(gamma glutamic acid)$_3$-Stearoyl (-(PEG$_2$DGA)$_3$-(gE)$_3$-Stea), -PEG$_{12}$-(gamma glutamic acid)$_3$-Stearoyl (-(PEG$_{12}$)-(gE)$_3$-Stea), -(PEG$_2$)$_2$-(gamma glutamic acid)$_3$-PEG$_2$-Stearoyl (-(PEG$_2$)$_2$-(gE)$_3$-PEG$_2$-Stea), -(PEG$_2$)$_2$-(gamma glutamic acid)$_2$-PEG$_2$-(gamma glutamic acid)-Stearoyl (-(PEG$_2$)$_2$-(gE)$_2$-PEG$_2$-(gE)-Stea), -(PEG$_2$)$_2$-(gamma glutamic acid)$_3$-PEG$_2$-(gamma glutamic acid)-Stearoyl (-(PEG$_2$)$_2$-(gE)$_3$-PEG$_2$-(gE)-Stea), -(gamma glutamic acid)$_2$-(PEG$_2$)$_2$-(gamma glutamic acid)-Stearoyl (-(gE)$_2$-(PEG$_2$)$_2$-(gE)-Stea), -(gamma glutamic acid)$_2$-(PEG$_2$)$_3$-(gamma glutamic acid)-Stearoyl (-(gE)$_2$-(PEG$_2$)$_3$-(gE)-Stea), -(PEG$_2$)$_3$-(gamma glutamic acid)$_5$-Stearoyl (-(PEG$_2$)$_3$-(gE)$_5$-Stea), -(PEG$_2$)$_3$-(gamma glutamic acid)$_3$-Lauroyl (-(PEG$_2$)$_3$-(gE)$_3$-Lau), -(gamma glutamic acid)$_5$-stearoyl (-(gE)$_5$-Stea), -(PEG$_2$)$_4$-(gamma glutamic acid)$_4$-Palmitoyl (-(PEG$_2$)$_4$-(gE)$_4$-Palm), -(gamma glutamic acid)$_4$-Lauroyl (-(gE)$_4$-Lau), -(PEG$_2$)$_3$-(gamma glutamic acid)$_3$-Pentadecanoyl (-(PEG$_2$)$_3$-(gE)$_3$-Penta), -(PEG$_2$)$_3$-(gamma glutamic acid)$_3$-Heptadecanoyl (-(PEG$_2$)$_3$-(gE)$_3$-Hepta), -(PEG$_2$)$_2$-(gamma glutamic acid)$_2$-PEG$_2$-(gamma glutamic acid)-Palmitoyl (-(PEG$_2$)$_2$-(gE)$_2$-PEG$_2$-(gE)-Palm), -(TTDS)$_2$-(gamma glutamic acid)$_3$-Palmitoyl (-(TTDS)$_2$-(gE)$_3$-Palm), -(gamma glutamic acid)$_4$-Pentadecanoyl (-(gE)$_4$-Penta), -(gamma glutamic acid)$_2$-Pentadecanoyl (-(gE)$_2$-Penta), -(gamma glutamic acid)$_4$-Myristoyl (-(gE)$_4$-Myr), -(PEG$_2$)$_3$-(gamma glutamic acid)$_3$-Myristoyl (-(PEG$_2$)$_3$-(gE)$_3$-Myr), -(PEG$_2$)$_4$-(gamma glutamic acid)$_4$-Stearoyl (-(PEG$_2$)$_4$-(gE)$_4$-Stea), -(TTDS)$_3$-(gamma glutamic acid)$_3$-Palmitoyl (-(TTDS)$_3$-(gE)$_3$-Palm), -(gamma glutamic acid)$_3$-Pentadecanoyl (-(gE)$_3$-Penta), -(TTDS)$_3$-(gamma glutamic acid)$_3$-Pentadecanoyl (-(TTDS)$_3$-(gE)$_3$-Penta), -(PEG$_2$)$_3$-(gamma glutamic acid)$_3$-Eicosanoyl ((-(PEG$_2$)$_3$-(gE)$_3$-Eico) and -(PEG$_2$)$_3$-(gamma glutamic acid)$_3$-docosanoyl ((-(PEG$_2$)$_3$-(gE)$_3$-Doco), or a salt or solvate thereof.

3. The peptide according to claim 1, wherein it has an amino acid sequence selected from the group consisting of the amino acid sequences of reference SEQ ID NO: 1-193.

4. The peptide according to claim 1, wherein $(X_{35})_e$ represents a polyethylene glycol derivative selected from the group consisting of PEG$_2$, (PEG$_2$)$_2$, (PEG$_2$)$_3$, (PEG$_2$)$_4$, PEG$_2$DGA, (PEG$_2$DGA)$_2$, (PEG$_2$DGA)$_3$, (TTDS)$_2$, (TTDS)$_3$, PEG$_4$, (PEG$_4$)$_2$, PEG$_8$, PEG$_{12}$, PEG$_{24}$ and PEG$_{28}$ or a salt or solvate thereof.

5. The peptide according to claim 1, wherein Z is selected from the group consisting of -gamma glutamic acid-palmitoyl (-gE-Palm), -(gamma glutamic acid)$_2$-palmitoyl (-(gE)$_2$-Palm), -(gamma glutamic acid)$_3$-palmitoyl (-(gE)$_3$-Palm), -(gamma glutamic acid)$_3$-stearoyl (-(gE)$_3$-Stea), -(gamma glutamic acid)$_4$-stearoyl (-(gE)$_4$-Stea), -(gamma glutamic acid)$_4$-plamitoyl (-(gE)$_4$-Palm), -(PEG$_2$)$_2$-(gamma glutamic acid)-Stearoyl (-(PEG$_2$)$_2$-gE-Stea), -(PEG$_2$)$_2$-(gamma glutamic acid)$_2$-Palmitoyl (-(PEG$_2$)$_2$-(gE)$_2$-Palm), -(PEG$_2$)$_2$-(gamma glutamic acid)$_3$-Palmitoyl (-(PEG$_2$)$_2$-(gE)$_3$-Palm), -(PEG$_2$)$_3$-(gamma glutamic acid)$_3$-Palmitoyl (-(PEG$_2$)$_3$-(gE)$_3$-Palm), -(PEG$_2$)$_4$-(gamma glutamic acid)$_3$-Palmitoyl (-(PEG$_2$)$_4$-(gE)$_3$-Palm), -(PEG$_2$)$_3$-(gamma glutamic acid)$_4$-Palmitoyl (-(PEG$_2$)$_3$-(gE)$_4$-Palm), -PEG$_{12}$-(gamma glutamic acid)$_3$-Palmitoyl (-PEG$_{12}$-(gE)$_3$-Palm), -(PEG$_2$)$_2$-(gamma glutamic acid)$_3$-Stearoyl (-(PEG$_2$)$_2$-(gE)$_3$-Stea), -(PEG$_2$)$_3$-(gamma glutamic acid)$_3$-Stearoyl (-(PEG$_2$)$_3$-(gE)$_3$-Stea), -(PEG$_2$)$_3$-(gamma glutamic acid)$_4$-Stearoyl (-(PEG$_2$)$_3$-(gE)$_4$-Stea), -(PEG$_2$)$_4$-(gamma glutamic acid)$_3$-Stearoyl (-(PEG$_2$)$_4$-(gE)$_3$-Stea), -(PEG$_2$)$_5$-(gamma glutamic acid)$_3$-Stearoyl (-(PEG$_2$)$_5$-(gE)$_3$-Stea), -(PEG$_2$DGA)-(gamma glutamic acid)$_3$-Stearoyl (-(PEG$_2$DGA)-(gE)$_3$-Stea), -(PEG$_2$DGA)$_2$-(gamma glutamic acid)$_3$-Stearoyl (-(PEG$_2$DGA)$_2$-(gE)$_3$-Stea), -(PEG$_2$DGA)$_3$-(gamma glutamic acid)$_3$-Stearoyl (-(PEG$_2$DGA)$_3$-(gE)$_3$-Stea), -PEG$_{12}$-(gamma glutamic acid)$_3$-Stearoyl (-(PEG$_{12}$)-(gE)$_3$-Stea), -(PEG$_2$)$_2$-(gamma glutamic acid)$_3$-PEG$_2$-Stearoyl (-(PEG$_2$)$_2$-(gE)$_3$-PEG$_2$-Stea), -(PEG$_2$)$_2$-(gamma glutamic acid)$_2$-PEG$_2$-(gamma glutamic acid)-Stearoyl (-(PEG$_2$)$_2$-(gE)$_2$-PEG$_2$-(gE)-Stea), -(PEG)$_2$-(gamma glutamic acid)$_3$-PEG$_2$-(gamma glutamic acid)-Stearoyl (-(PEG$_2$)$_2$-(gE)$_3$-PEG$_2$-(gE)-Stea), -(gamma glutamic acid)$_2$-(PEG$_2$)$_2$-(gamma glutamic acid)-Stearoyl (-(gE)$_2$-(PEG$_2$)$_2$-(gE)-Stea), -(gamma glutamic acid)$_2$-(PEG$_2$)$_3$-(gamma glutamic acid)-Stearoyl (-(gE)$_2$-(PEG$_2$)$_3$-(gE)-Stea), -(PEG$_2$)$_3$-(gamma glutamic acid)$_5$-Stearoyl (-(PEG$_2$)$_3$-(gE)$_5$-Stea), -(gamma glutamic acid)$_5$-Stearoyl (-(gE)$_5$-Stea), -(PEG$_2$)$_4$-(gamma glutamic acid)$_4$-Palmitoyl (-(PEG$_2$)$_4$-(gE)$_4$-Palm); -(gamma glutamic acid)$_4$-Lauroyl (-(gE)$_4$-Lau), -(PEG$_2$)$_3$-(gamma glutamic acid)$_3$-Pentadecanoyl (-(PEG$_2$)$_3$-(gE)$_3$-Penta), -(PEG$_2$)$_3$-(gamma glutamic acid)$_3$-Heptadecanoyl (-(PEG$_2$)$_3$-(gE)$_3$-Hepta), -(PEG$_2$)$_2$-(gamma glutamic acid)$_2$-PEG$_2$-(gamma glutamic acid)-Palmitoyl (-(PEG$_2$)$_2$-(gE)$_2$-PEG$_2$-(gE)-Palm), -(TTDS)$_2$-(gamma glutamic acid)$_3$-Palmitoyl (-(TTDS)$_2$-(gE)$_3$-Palm), -(gamma glutamic acid)$_4$-Pentadecanoyl (-(gE)$_4$-Penta), -(gamma glutamic acid)$_2$-Pentadecanoyl (-(gE)$_2$-Penta), -(gamma glutamic acid)$_4$-Myristoyl (-(gE)$_4$-Myr), -(PEG$_2$)$_4$-(gamma glutamic acid)$_4$-Stearoyl (-(PEG$_2$)$_4$-(gE)$_4$-Stea), -(TTDS)$_3$-(gamma glutamic acid)$_3$-Palmitoyl (-(TTDS)$_3$-(gE)$_3$-Palm), -(gamma glutamic acid)$_3$-Pentadecanoyl (-(gE)$_3$-Penta), -(TTDS)$_3$-(gamma glutamic acid)$_3$-Pentadecanoyl (-(TTDS)$_3$-(gE)$_3$-Penta), -(PEG$_2$)$_3$-(gamma glutamic acid)$_3$-Eicosanoyl ((-PEG$_2$)$_3$-(gE)$_3$-Eico) and -(PEG$_2$)$_3$-(gamma glutamic acid)$_3$-docosanoyl ((-PEG$_2$)$_3$-(gE)$_3$-Doco); or a salt or solvate thereof.

6. The peptide according to claim 1 of formula (Ia), wherein:

$N_{ter}$ represents the N-terminal end of the peptide;
$C_{ter}$ represents the C-terminal end of the peptide;
a, b, c and d independently represent 0 or 1;
e represents 0, 1, 2, 3 or 4;
f represents 0, 2 or 3;
Ac represents acetyl group;
E represents glutamic acid;
L represents leucine;
G represents glycine;
R represents arginine;
K represents lysine;
V represents valine;
$X_{18}$ represents an amino acid selected from the group consisting of alanine, 2-amino-isobutyric acid and leucine;
$X_{19}$ represents an amino acid selected from the group consisting of glutamine, Nε-acetyl-lysine and alanine;
I represents isoleucine;
Aib represents 2-amino-isobutyric acid;
$X_{25}$ represents an amino acid selected from the group consisting of methionine, norleucine, glutamine, Nε-acetyl-lysine and glutamic acid;
S represents serine;
T represents threonine;
$X_{28}$ represents an amino acid selected from the group consisting of tryptophan, 1-naphtylalanine, phenylalanine, tyrosine, α-methyl-tryptophane, α-methyl-phenylalanine and 5-hydroxy-tryptophane;
$X_{29}$ represents an amino acid selected from the group consisting of serine, threonine and α-methyl-serine;
$X_{30}$ represents an amino acid selected from the group consisting of lysine, 2-amino-isobutyric acid and α-methyl-lysine;
$X_{31}$ represents an amino acid selected from the group consisting of arginine, Nω-methyl-arginine, Nω,Nω'-dimethylmethyl-arginine, alanine and citruline;
$X_{32}$ represents an amino acid selected from the group consisting of lysine, alanine and Nε,Nε,Nε-tri-methyl-lysine;
$X_{33}$ represents an amino acid selected from the group consisting of leucine, lysine and Nε-acetyl-lysine;
$(X_{35})_e$ represents a polyethylene glycol derivative selected from the group consisting of PEG$_2$, (PEG$_2$)$_2$, (PEG$_2$)$_3$, (PEG$_2$)$_4$, PEG$_2$DGA, (PEG$_2$DGA)$_2$, (PEG$_2$DGA)$_3$, (TTDS)$_2$, (TTDS)$_3$, PEG$_4$, (PEG$_4$)$_2$, PEG$_8$, PEG$_{12}$, PEG$_{24}$ and PEG$_{28}$;
gE represents gamma-glutamic acid;
$X_{37}$ represents the following structure:

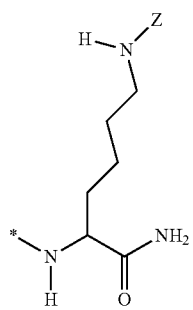

in which:
-* is as defined in claim 1; and
Z is selected from the group consisting of -gamma glutamic acid-palmitoyl (-gE-Palm), -(gamma glutamic acid)$_2$-palmitoyl (-(gE)$_2$-Palm), -(gamma glutamic acid)$_3$-palmitoyl (-(gE)$_3$-Palm), -(gamma glutamic acid)$_3$-stearoyl (-(gE)$_3$-Stea), -(gamma glutamic acid)$_4$-stearoyl (-(gE)$_4$-Stea), -(gamma glutamic acid)$_4$-plamitoyl (-(gE)$_4$-Palm), -(PEG$_2$)$_2$-(gamma glutamic acid)-Stearoyl (-(PEG$_2$)$_2$-gE-Stea), -(PEG$_2$)$_2$-(gamma glutamic acid)$_2$-Palmitoyl (-(PEG$_2$)$_2$-(gE)$_2$-Palm), -(PEG$_2$)$_2$-(gamma glutamic acid)$_3$-Palmitoyl (-(PEG$_2$)$_2$-(gE)$_3$-Palm), -(PEG$_2$)$_3$-(gamma glutamic acid)$_3$-Palmitoyl (-(PEG$_2$)$_3$-(gE)$_3$-Palm), -(PEG$_2$)$_4$-(gamma glutamic acid)$_3$-Palmitoyl (-(PEG$_2$)$_4$-(gE)$_3$-Palm), -(PEG$_2$)$_3$-(gamma glutamic acid)$_4$-Palmitoyl (-(PEG$_2$)$_3$-(gE)$_4$-Palm), -PEG$_{12}$-(gamma glutamic acid)$_3$-Palmitoyl (-PEG$_{12}$-(gE)$_3$-Palm), -(PEG$_2$)$_2$-(gamma glutamic acid)$_3$-Stearoyl (-(PEG$_2$)$_2$-(gE)$_3$-Stea), -(PEG$_2$)$_3$-(gamma glutamic acid)$_3$-Stearoyl (-(PEG$_2$)$_3$-(gE)$_3$-Stea), -(PEG$_2$)$_3$-(gamma glutamic acid)$_4$-Stearoyl (-(PEG$_2$)$_3$-(gE)$_4$-Stea), -(PEG$_2$)$_4$-(gamma glutamic acid)$_3$-Stearoyl (-(PEG$_2$)$_4$-(gE)$_3$-Stea), -(PEG$_2$)$_5$-(gamma glutamic acid)$_3$-Stearoyl (-(PEG$_2$)$_5$-(gE)$_3$-Stea), -(PEG$_2$DGA)-(gamma glutamic acid)$_3$-Stearoyl (-(PEG$_2$DGA)-(gE)$_3$-Stea), -(PEG$_2$DGA)$_2$-(gamma glutamic acid)$_3$-Stearoyl (-(PEG$_2$DGA)$_2$-(gE)$_3$-Stea), -(PEG$_2$DGA)$_3$-(gamma glutamic acid)$_3$-Stearoyl (-(PEG$_2$DGA)$_3$-(gE)$_3$-Stea), -PEG$_{12}$-(gamma glutamic acid)$_3$-Stearoyl (-(PEG$_{12}$)-(gE)$_3$-Stea), -(PEG$_2$)$_2$-(gamma glutamic acid)$_3$-PEG$_2$-Stearoyl (-(PEG$_2$)$_2$-(gE)$_3$-PEG$_2$-Stea), -(PEG$_2$)$_2$-(gamma glutamic acid)$_2$-PEG$_2$-(gamma glutamic acid)-Stearoyl (-(PEG$_2$)$_2$-(gE)$_2$-PEG$_2$-(gE)-Stea), -(PEG$_2$)$_2$-(gamma glutamic acid)$_3$-PEG$_2$-(gamma glutamic acid)-Stearoyl (-(PEG$_2$)$_2$-(gE)$_3$-PEG$_2$-(gE)-Stea), -(gamma glutamic acid)$_2$-(PEG$_2$)$_2$-(gamma glutamic acid)-Stearoyl (-(gE)$_2$-(PEG$_2$)$_2$-(gE)-Stea), -(gamma glutamic acid)$_2$-(PEG$_2$)$_3$-(gamma glutamic acid)-Stearoyl (-(gE)$_2$-(PEG$_2$)$_3$-(gE)-Stea), -(PEG$_2$)$_3$-(gamma glutamic acid)$_5$-Stearoyl (-(PEG$_2$)$_3$-(gE)$_5$-Stea), -(gamma glutamic acid)$_5$-Stearoyl (-(gE)$_5$-Stea), -(PEG$_2$)$_4$-(gamma glutamic acid)$_4$-Palmitoyl (-(PEG$_2$)$_4$-(gE)$_4$-Palm); -(gamma glutamic acid)$_4$-Lauroyl (-(gE)$_4$-Lau), -(PEG$_2$)$_3$-(gamma glutamic acid)$_3$-Pentadecanoyl (-(PEG$_2$)$_3$-(gE)$_3$-Penta), -(PEG$_2$)$_3$-(gamma glutamic acid)$_3$-Heptadecanoyl (-(PEG$_2$)$_3$-(gE)$_3$-Hepta), -(PEG$_2$)$_2$-(gamma glutamic acid)$_2$-PEG$_2$-(gamma glutamic acid)-Palmitoyl (-(PEG$_2$)$_2$-(gE)$_2$-PEG$_2$-(gE)-Palm), -(TTDS)$_2$-(gamma glutamic acid)$_3$-Palmitoyl (-(TTDS)$_2$-(gE)$_3$-Palm), -(gamma glutamic acid)$_4$-Pentadecanoyl (-(gE)$_4$-Penta), -(gamma glutamic acid)$_2$-Pentadecanoyl (-(gE)$_2$-Penta), -(gamma glutamic acid)$_4$-Myristoyl (-(gE)$_4$-Myr), -(PEG$_2$)$_4$-(gamma glutamic acid)$_4$-Stearoyl (-(PEG$_2$)$_4$-(gE)$_4$-Stea), -(TTDS)$_3$-(gamma glutamic acid)$_3$-Palmitoyl (-(TTDS)$_3$-(gE)$_3$-Palm), -(gamma glutamic acid)$_3$-Pentadecanoyl (-(gE)$_3$-Penta), -(TTDS)$_3$-(gamma glutamic acid)$_3$-Pentadecanoyl (-(TTDS)$_3$-(gE)$_3$-Penta), -(PEG$_2$)$_3$-(gamma glutamic acid)$_3$-Eicosanoyl ((-PEG$_2$)$_3$-(gE)$_3$-Eico) and -(PEG$_2$)$_3$-(gamma glutamic acid)$_3$-docosanoyl ((-PEG$_2$)$_3$-(gE)$_3$-Doco);
or a salt or solvate thereof.

7. The peptide according to claim 1, having an amino acid sequence selected from the group consisting of SEQ ID NO: 9, 11, 13-20, 23-43, 45-49, 56-58, 60-119, 121-177 and 180-193.

8. The peptide according to claim 1, having an amino acid sequence selected from the group consisting of SEQ ID NO: 14-20, 23-43, 45-49, 56, 57, 60-119, 121-125, 127-133, 135-160, 162, 164-177 and 180-193.

9. The peptide according to claim 1, having an amino acid sequence selected from the group consisting of SEQ ID NO: 14-20, 26, 27, 30, 31, 33, 36, 38-43, 45, 46, 48, 56, 60, 61, 63-76, 79-86, 88-93, 98-113, 115, 116, 121-125, 128-131, 133, 135-143, 145, 146, 148-154, 156-160, 162, 164-174, 177, 182-189 and 191-193.

10. The peptide according to claim 1, having an amino acid sequence selected from the group consisting of SEQ ID NO: 14-20, 27, 38-43, 48, 60, 61, 64, 65, 67, 70, 72-75, 79, 81, 82, 84, 88-93, 99-106, 108-112, 115, 122-125, 128, 130, 131, 133, 136-143, 145, 146, 148-154, 156-160, 162, 165-171, 173, 174, 182-187, 189, 191 and 193.

11. The peptide according to claim 1, having the amino acid sequence of reference SEQ ID NO: 81, 150 or 170.

12. The peptide according to claim 1, having an amino acid sequence selected from the group consisting of SEQ ID NO: 14, 16, 39-42, 74, 75, 82, 84, 89-91, 99, 102, 103, 105, 122, 125, 133, 136, 138, 142, 146, 150, 152, 156, 157, 159, 167-170, 183 and 185.

13. A pharmaceutical composition comprising at least one peptide according to claim 1, or a pharmaceutically acceptable salt or solvate thereof, and at least one pharmaceutically acceptable carrier.

14. A method for treating a disease or condition implicating the Relaxin family peptide receptor 1 (RXFP1) comprising administering to an individual in need of said treatment a peptide according to claim 1, or a pharmaceutically acceptable salt or solvate thereof.

15. The method according to claim 14, wherein the disease or condition is selected from the group consisting of fibrosis, fibrotic diseases, idiopathic pulmonary fibrosis, kidney diseases involving fibrosis, pulmonary hypertension, and preeclampsia.

16. The method according to claim 14, wherein the disease or condition is selected from the group consisting of heart disease and vascular disease.

17. The method according to claim 16, wherein the disease or condition is selected from the group consisting of acute or chronic heart failure, systolic or diastolic heart failure, coronary artery disease, atherosclerosis, microvascular angina, and cardiovascular complication of diabetes.

18. The method according to claim 14, wherein the disease or condition is a renal failure.

19. The method according to claim 18, wherein the disease or condition is selected from renal dysfunction in cirrhosis, chronic kidney disease, and acute kidney injury.

20. The method according to claim 14, wherein the disease or condition is fibrotic disease selected from the group consisting of systemic sclerosis, scleroderma, and fibromyalgia.

\* \* \* \* \*

SEQUENCE LISTING

<160> NUMBER OF SEQ ID NOS: 201

```
<210> SEQ ID NO 1
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -
      palmitoyl group (-Palm)

<400> SEQUENCE: 1

Leu Glu Gly Arg Glu Lys Val Arg Ala Ala Ile Xaa Xaa Glu Gly Xaa
1               5                   10                  15

Ser Thr Trp Ser Xaa Arg Lys Xaa
            20

<210> SEQ ID NO 2
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
```

```
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -gamma
      glutamic acid-palmitoyl group (-gE-Palm)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 2

Leu Glu Gly Arg Glu Lys Val Arg Ala Gln Ile Xaa Xaa Gly Gly Xaa
1               5                   10                  15

Ser Thr Trp Ser Xaa Arg Lys Xaa
            20

<210> SEQ ID NO 3
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -gamma
      glutamic acid-stearoyl group (-gE-Stea)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 3

Leu Glu Gly Arg Glu Lys Val Arg Ala Gln Ile Xaa Xaa Gly Gly Xaa
1               5                   10                  15

Ser Thr Trp Ser Xaa Arg Lys Xaa
            20

<210> SEQ ID NO 4
```

```
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 14
<223> OTHER INFORMATION: Xaa in position 14 represents 2-amino-
      isobutyric acid (Aib)
<220> FEATURE:
<221> NAME/KEY: VARIANT
<222> LOCATION: 17
<223> OTHER INFORMATION: Xaa in position 17 represents 2-amino hexanoic
      acid (Norleucine - Nle)
<220> FEATURE:
<221> NAME/KEY: VARIANT
<222> LOCATION: 22
<223> OTHER INFORMATION: Xaa in position 22 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)2-palmitoyl group (-(gE)2-Palm)

<400> SEQUENCE: 4

Glu Leu Glu Gly Arg Glu Lys Val Arg Ala Ala Ile Xaa Xaa Glu Gly
1               5                   10                  15

Xaa Ser Thr Trp Ser Xaa Arg Lys Xaa
            20                  25

<210> SEQ ID NO 5
<211> LENGTH: 23
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
```

```
<222> LOCATION: 23
<223> OTHER INFORMATION: Xaa in position 23 represents a lysine amino
      acid bound on the nitrogen atom of its lateral chain to a -(gamma
      glutamic acid)2-palmitoyl group (-(gE)2-Palm)
<220> FEATURE:
<221> NAME/KEY: VARIANT
<222> LOCATION: 23
<223> OTHER INFORMATION: The peptide is substituted with an -NH2 group
      on its C-terminal extremity

<400> SEQUENCE: 5

Leu Glu Gly Arg Glu Lys Val Arg Ala Gln Ile Xaa Xaa Glu Gly Met
1               5                   10                  15

Ser Thr Trp Ser Xaa Arg Xaa
            20

<210> SEQ ID NO 6
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 14
<223> OTHER INFORMATION: Xaa in position 14 represents 2-amino-
      isobutyric acid (Aib)
<220> FEATURE:
<221> NAME/KEY: VARIANT
<222> LOCATION: 17
<223> OTHER INFORMATION: Xaa in position 17 represents 2-amino hexanoic
      acid (Norleucine - Nle)
<220> FEATURE:
<221> NAME/KEY: VARIANT
<222> LOCATION: 22
<223> OTHER INFORMATION: Xaa in position 22 represents 2-amino-
      isobutyric acid (Aib)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -(gamma
      glutamic acid)3-palmitoyl group (-(gE)3-Palm)

<400> SEQUENCE: 6

Glu Leu Glu Gly Arg Glu Lys Val Arg Ala Ala Ile Xaa Xaa Glu Gly
1               5                   10                  15

Xaa Ser Thr Trp Ser Xaa Arg Lys Lys Xaa
            20                  25

<210> SEQ ID NO 7
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
```

```
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-palmitoyl group (-(gE)3-Palm)

<400> SEQUENCE: 7

Leu Glu Gly Arg Glu Lys Val Arg Ala Gln Ile Xaa Xaa Glu Gly Met
1               5                   10                  15

Ser Thr Trp Ser Xaa Arg Lys Xaa
            20

<210> SEQ ID NO 8
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-palmitoyl group (-(gE)3-Palm)
<220> FEATURE:
<221> NAME/KEY: VARIANT
<222> LOCATION: 24
```

<223> OTHER INFORMATION: The peptide is substituted with an -NH2 group
     on its C-terminal extremity

<400> SEQUENCE: 8

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 9
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-stearoyl group (-(gE)3-Stea)

<400> SEQUENCE: 9

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 10
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-

```
        isobutyric acid (Aib)
<220> FEATURE:
<221> NAME/KEY: VARIANT
<222> LOCATION: 13
<223> OTHER INFORMATION: Xaa in position 13 represents 2-amino-
        isobutyric acid (Aib)
<220> FEATURE:
<221> NAME/KEY: VARIANT
<222> LOCATION: 16
<223> OTHER INFORMATION: Xaa in position 16 represents 2-amino hexanoic
        acid (Norleucine - Nle)
<220> FEATURE:
<221> NAME/KEY: VARIANT
<222> LOCATION: 21
<223> OTHER INFORMATION: Xaa in position 21 represents 2-amino-
        isobutyric acid (Aib)
<220> FEATURE:
<221> NAME/KEY: VARIANT
<222> LOCATION: 23, 24
<223> OTHER INFORMATION: Linked by -PEG2-
<220> FEATURE:
<221> NAME/KEY: VARIANT
<222> LOCATION: 24
<223> OTHER INFORMATION: The peptide is substituted with an -NH2 group
        on its C-terminal extremity
<220> FEATURE:
<221> NAME/KEY: VARIANT
<222> LOCATION: 24
<223> OTHER INFORMATION: Xaa in position 24 represents a lysine amino
        acid bound on the nitrogen atom of its lateral chain to a -(gamma
        glutamic acid)3-palmitoyl (-(gE)3-Palm)

<400> SEQUENCE: 10

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 11
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
        group on its N-terminal extremity
<220> FEATURE:
<221> NAME/KEY: VARIANT
<222> LOCATION: 12
<223> OTHER INFORMATION: Xaa in position 12 represents 2-amino-
        isobutyric acid (Aib)
<220> FEATURE:
<221> NAME/KEY: VARIANT
<222> LOCATION: 13
<223> OTHER INFORMATION: Xaa in position 13 represents 2-amino-
        isobutyric acid (Aib)
<220> FEATURE:
<221> NAME/KEY: VARIANT
<222> LOCATION: 16
<223> OTHER INFORMATION: Xaa in position 16 represents 2-amino hexanoic
        acid (Norleucine - Nle)
<220> FEATURE:
<221> NAME/KEY: VARIANT
<222> LOCATION: 21
<223> OTHER INFORMATION: Xaa in position 21 represents 2-amino-
        isobutyric acid (Aib)
<220> FEATURE:
<221> NAME/KEY: VARIANT
<222> LOCATION: 23, 24
<223> OTHER INFORMATION: Linked by -PEG2-PEG2-
<220> FEATURE:
<221> NAME/KEY: VARIANT
<222> LOCATION: 24
```

```
<223> OTHER INFORMATION: Xaa in position 24 represents a lysine amino
      acid bound on the nitrogen atom of its lateral chain to a -(gamma
      glutamic acid)3-palmitoyl group (-(gE)3-Palm)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 11

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 12
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 23, 24
<223> OTHER INFORMATION: Linked by -PEG2-
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -PEG2-
      (gamma glutamic acid)3-Palmitoyl group (-PEG2-(gE)3-Palm)

<400> SEQUENCE: 12

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 13
<211> LENGTH: 24
<212> TYPE: PRT
<213> ORGANISM: Artificial Sequence
<220> FEATURE:
```

```
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 23, 24
<223> OTHER INFORMATION: Linked by -PEG2-
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -
      (PEG2)2-(gamma glutamic acid)3-Palmitoyl group (-(PEG2)2-(gE)3-
      Palm)

<400> SEQUENCE: 13

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 14
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
```

```
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to -(gamma
      glutamic acid)3-stearoyl group (-(gE)3-Stea)
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 14

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 15
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
```

-continued

```
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-stearoyl group (-(gE)4-Stea)

<400> SEQUENCE: 15

Leu Glu Gly Arg Glu Lys Val Arg Ala Xaa Ile Xaa Xaa Glu Gly Xaa
1               5                   10                  15

Ser Thr Trp Ser Xaa Arg Lys Lys Xaa
            20                  25

<210> SEQ ID NO 16
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-stearoyl group (-(gE)4-Stea)
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 16

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
```

```
            20                  25

<210> SEQ ID NO 17
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-plamitoyl group (-(gE)4-Palm)
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 17

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 18
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
```

```
       group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2DGA-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 18

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 19
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
```

```
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2DGA-PEG2DGA-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 19

Leu Glu Gly Arg Glu Lys Val Arg Ala Xaa Ile Xaa Xaa Gly Gly Xaa
1               5                   10                  15

Ser Thr Trp Ser Xaa Arg Lys Xaa Xaa
            20                  25

<210> SEQ ID NO 20
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
```

```
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2DGA-PEG2DGA-PEG2DGA-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 20

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 21
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
``` acid bound on the nitrogen atom of its lateral chain to a -
stearoyl group (-stea)

<400> SEQUENCE: 21

Leu Glu Gly Arg Glu Lys Val Arg Ala Gln Ile Xaa Xaa Glu Gly Xaa
1               5                   10                  15

Ser Thr Trp Ser Xaa Arg Lys Xaa Xaa
            20                  25

<210> SEQ ID NO 22
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -gamma
      glutamic acid-stearoyl group (-gE-Stea)

<400> SEQUENCE: 22

Leu Glu Gly Arg Glu Lys Val Arg Ala Gln Ile Xaa Xaa Glu Gly Xaa
1               5                   10                  15

Ser Thr Trp Ser Xaa Arg Lys Lys Xaa
            20                  25

<210> SEQ ID NO 23
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity

```
<220> FEATURE:
<221> NAME/KEY: VARIANT
<222> LOCATION: 12
<223> OTHER INFORMATION: Xaa in position 12 represents 2-amino-
      isob

```
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-palmitoyl group (-(gE)3-Palm)

<400> SEQUENCE: 24

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 25
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 23, 24
<223> OTHER INFORMATION: Linked by -PEG12-
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-palmitoyl group (-(gE)3-Palm)

<400> SEQUENCE: 25

Leu Glu Gly Arg Glu Lys Val Arg Ala Xaa Ile Xaa Xaa Glu Gly Met
1               5                   10                  15

Ser Thr Trp Ser Xaa Arg Lys Xaa
            20

<210> SEQ ID NO 26
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
```

```
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl (-(gE)3-Palm)

<400> SEQUENCE: 26

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 27
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 9
<223> OTHER INFORMATION: Xaa in position 9 represents 2-amino-isobutyric
      acid (Aib)
<220> FEATURE:
<221> NAME/KEY: VARIANT
<222> LOCATION: 10
```

```
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl group (-(gE)3-Palm)

<400> SEQUENCE: 27

Leu Glu Gly Arg Glu Lys Val Arg Xaa Xaa Ile Xaa Xaa Glu Gly Xaa
1               5                   10                  15

Ser Thr Trp Ser Xaa Arg Lys Xaa Xaa
            20                  25

<210> SEQ ID NO 28
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 9
<223> OTHER INFORMATION: Xaa in position 9 represents 2-amino-isobutyric
      acid (Aib)
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
```

```
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl group (-(gE)3-Palm)

<400> SEQUENCE: 28

Leu Glu Gly Arg Glu Lys Val Arg Xaa Gln Ile Xaa Xaa Glu Gly Xaa
1               5                   10                  15

Ser Thr Trp Ser Xaa Arg Lys Xaa Xaa
            20                  25

<210> SEQ ID NO 29
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents 1-Naphtylalanine
      (1-Nal)
<220> FEATURE:
<221> NAME/KEY: VARIANT
<222> LOCATION: 21
<223> OTHER INFORMATION: Xaa in position 21 represents 2-amino-
```

```
        isobutyric acid (Aib)
<220> FEATURE:
<221> NAME/KEY: VARIANT
<222> LOCATION: 23, 24
<223> OTHER INFORMATION: Linked by -PEG12-
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-palmitoyl group (-(gE)3-Palm)

<400> SEQUENCE: 29

Leu Glu Gly Arg Glu Lys Val Arg Ala Xaa Ile Xaa Xaa Glu Gly Xaa
1               5                   10                  15

Ser Thr Xaa Ser Xaa Arg Lys Xaa
            20

<210> SEQ ID NO 30
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 23, 24
<223> OTHER INFORMATION: Linked by -PEG12-
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-stearoyl group (-(gE)3-Stea)

<400> SEQUENCE: 30

Leu Glu Gly Arg Glu Lys Val Arg Ala Gln Ile Xaa Xaa Glu Gly Xaa
1               5                   10                  15

Ser Thr Trp Ser Xaa Arg Lys Xaa
```

```
<210> SEQ ID NO 31
<211> LENGTH: 25
<212> TYPE: PRT
<213> ORGANISM: Artificial Sequence
<220> FEATURE:
<223> OTHER IN

```
        isobutyric acid (Aib)
<220> FEATURE:
<221> NAME/KEY: VARIANT
<222> LOCATION: 13
<223> OTHER INFORMATION: Xaa in position 13 represents 2-amino-
        isobutyric acid (Aib)
<220> FEATURE:
<221> NAME/KEY: VARIANT
<222> LOCATION: 16
<223> OTHER INFORMATION: Xaa in position 16 represents 2-amino hexanoic
        acid (Norleucine - Nle)
<220> FEATURE:
<221> NAME/KEY: VARIANT
<222> LOCATION: 21
<223> OTHER INFORMATION: Xaa in position 21 represents 2-amino-
        isobutyric acid (Aib)
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
        on its C-terminal extremity
<220> FEATURE:
<221> NAME/KEY: VARIANT
<222> LOCATION: 25
<223> OTHER INFORMATION: Xaa in position 25 represents a lysine amino
        acid bound on the nitrogen atom of its lateral chain to a -(gamma
        glutamic acid)3-stearoyl group (-(gE)3-Stea)

<400> SEQUENCE: 32

Leu Glu Gly Arg Glu Lys Val Arg Ala Xaa Ile Xaa Xaa Glu Gly Xaa
1               5                   10                  15

Ser Thr Trp Ser Xaa Arg Lys Lys Xaa
            20                  25

<210> SEQ ID NO 33
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
        group on its N-terminal extremity
<220> FEATURE:
<221> NAME/KEY: VARIANT
<222> LOCATION: 10
<223> OTHER INFORMATION: Xaa in position 10 represents 2-amino-4-
        acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
        isobutyric acid (Aib)
<220> FEATURE:
<221> NAME/KEY: VARIANT
<222> LOCATION: 13
<223> OTHER INFORMATION: Xaa in position 13 represents 2-amino-
        isobutyric acid (Aib)
<220> FEATURE:
<221> NAME/KEY: VARIANT
<222> LOCATION: 16
<223> OTHER INFORMATION: Xaa in position 16 represents 2-amino hexanoic
        acid (Norleucine - Nle)
<220> FEATURE:
<221> NAME/KEY: VARIANT
<222> LOCATION: 21
<223> OTHER INFORMATION: Xaa in position 21 represents 2-amino-
        isobutyric acid (Aib)
<220> FEATURE:
<221> NAME/KEY: VARIANT
```

```
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 33

Leu Glu Gly Arg Glu Lys Val Arg Ala Xaa Ile Xaa Xaa Glu Gly Xaa
1               5                  10                  15

Ser Thr Trp Ser Xaa Arg Lys Xaa Xaa
            20                  25

<210> SEQ ID NO 34
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 23, 24
<223> OTHER INFORMATION: Linked by -PEG12-
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-stearoyl group (-(gE)3-Stea)
```

<400> SEQUENCE: 34

Leu Glu Gly Arg Glu Lys Val Arg Ala Xaa Ile Xaa Xaa Glu Gly Xaa
1               5

```
<222> LOCATION: 9
<223> OTHER INFORMATION: Xaa in position 9 represents 2-amino-isobutyric
      acid (Aib)
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 36

Leu Glu Gly Arg Glu Lys Val Arg Xaa Xaa Ile Xaa Xaa Glu Gly Xaa
1               5                   10                  15

Ser Thr Trp Ser Xaa Arg Lys Xaa Xaa
            20                  25

<210> SEQ ID NO 37
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 9
<223> OTHER INFORMATION: Xaa in position 9 represents 2-amino-isobutyric
      acid (Aib)
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
```

```
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents 1-Naphtylalanine
      (1-Nal)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 37

Leu Glu Gly Arg Glu Lys Val Arg Xaa Xaa Ile Xaa Xaa Glu Gly Xaa
1               5                   10                  15

Ser Thr Xaa Ser Xaa Arg Lys Xaa Xaa
            20                  25

<210> SEQ ID NO 38
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
```

```
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 23, 24
<223> OTHER INFORMATION: Linked by
      -PEG12-
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-palmitoyl group (-(gE)3-Palm)

<400> SEQUENCE: 38

Leu Glu Gly Arg Glu Lys Val Arg Ala Xaa Ile Xaa Xaa Glu Gly Xaa
1               5                   10                  15

Ser Thr Trp Ser Xaa Arg Lys Xaa
            20

<210> SEQ ID NO 39
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 20
<223> OTHER INFORMATION: Xaa in position 20 represents alpha-Methyl-
      serine (Mse)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
```

```
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-stearoyl group (-(gE)4-Stea)
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 39

Leu Glu Gly Arg Glu Lys Val Arg Ala Xaa Ile Xaa Xaa Glu Gly Xaa
1               5                   10                  15

Ser Thr Trp Xaa Lys Arg Lys Xaa Xaa
            20                  25

<210> SEQ ID NO 40
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 20
<223> OTHER INFORMATION: Xaa in position 20 represents alpha-Methyl-
      serine (Mse)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
``` on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-stearoyl group (-(gE)4-Stea)

<400> SEQUENCE: 40

Leu Glu Gly Arg Glu Lys Val Arg Ala Xaa Ile Xaa Xaa Glu Gly Xaa
1               5                   10                  15

Ser Thr Trp Xaa Xaa Arg Lys Xaa Xaa
            20                  25

<210> SEQ ID NO 41
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 20
<223> OTHER INFORMATION: Xaa in position 20 represents alpha-Methyl-
      serine (Mse)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 41

Leu Glu Gly Arg Glu Lys Val Arg Ala Xaa Ile Xaa Xaa Glu Gly Xaa
1               5                   10                  15

Ser Thr Trp Xaa Xaa Arg Lys Xaa Xaa
            20                  25

<210> SEQ ID NO 42
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
       acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-stearoyl group (-(gE)4-Stea)

<400> SEQUENCE: 42

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 43
<211> LENGTH: 25
<212> TYPE: PRT
<213> ORGANISM: Artificial Sequence

```
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-plamitoyl group (-(gE)4-Palm)

<400> SEQUENCE: 43

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 44
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
```

```
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Palmitoyl group (-(PEG2)3-(gE)3-
      Palm)

<400> SEQUENCE: 44

Leu Glu Gly Arg Glu Lys Val Arg Ala Xaa Ile Xaa Xaa Glu Gly Gln
1               5                   10                  15

Ser Thr Tyr Ser Xaa Arg Lys Xaa Xaa
            20                  25

<210> SEQ ID NO 45
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino
      hexanoic acid (Norleucine - Nle)
<220> FEATURE:
<221> NAME/KEY: VARIANT
<222> LOCATION: 19
<223> OTHER INFORMATION: Xaa in position 19 represents 1-Naphtylalanine
      (1-Nal)
<220> FEATURE:
<221> NAME/KEY: VARIANT
```

```
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 23, 24
<223> OTHER INFORMATION: Linked by -PEG12-
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-stearoyl (-(gE)3-Stea)

<400> SEQUENCE: 45

Leu Glu Gly Arg Glu Lys Val Arg Ala Xaa Ile Xaa Xaa Glu Gly Xaa
1               5                   10                  15

Ser Thr Xaa Ser Xaa Arg Lys Xaa
            20

<210> SEQ ID NO 46
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG12-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
```

```
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 46

Leu Glu Gly Arg Glu Lys Val Arg Ala Xaa Ile Xaa Xaa Glu Gly Xaa
1               5                   10                  15

Ser Thr Tyr Ser Xaa Arg Lys Xaa Xaa
            20                  25

<210> SEQ ID NO 47
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 23, 24
<223> OTHER INFORMATION: Linked by -PEG24-
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)3-palmitoyl group (-(gE)3-Palm)

<400> SEQUENCE: 47

Leu Glu Gly Arg Glu Lys Val Arg Ala Gln Ile Xaa Xaa Glu Gly Met
1               5                   10                  15

Ser Thr Trp Ser Xaa Arg Lys Xaa
            20

<210> SEQ ID NO 48
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
```

```
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24, 25
<223> OTHER INFORMATION: Linked by -PEG28-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 48

Leu Glu Gly Arg Glu Lys Val Arg Ala Xaa Ile Xaa Xaa Glu Gly Xaa
1               5                   10                  15

Ser Thr Trp Ser Xaa Arg Lys Lys Xaa
            20                  25

<210> SEQ ID NO 49
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
```

```
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG28-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 49

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 50
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -PEG2-
      Palmitoyl group (-PEG2-Palm)

<400> SEQUENCE: 50
```

-continued

```
Leu Gly Arg Glu Lys Val Arg Ala Gln Ile Xaa Xaa Glu G

```
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-Stearoyl group (-(PEG2)3-Stea)

<400> SEQUENCE: 52

Leu Glu Gly Arg Glu Lys Val Arg Ala Gln Ile Xaa Xaa Gly Gly Xaa
1               5                   10                  15

Ser Thr Trp Ser Xaa Arg Lys Xaa Xaa
            20                  25

<210> SEQ ID NO 53
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
```

```
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -PEG2-
      (gamma glutamic acid)-Palmitoyl group (-PEG2-gE-Palm)

<400> SEQUENCE: 53

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 54
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 14
<223> OTHER INFORMATION: Xaa in position 14 represents 2-amino-
      isobutyric acid (Aib)
<220> FEATURE:
<221> NAME/KEY: VARIANT
<222> LOCATION: 17
<223> OTHER INFORMATION: Xaa in position 17 represents 2-amino
      hexanoic acid (Norleucine - Nle)
<220> FEATURE:
<221> NAME/KEY: VARIANT
<222> LOCATION: 22
<223> OTHER INFORMATION: Xaa in position 22 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -PEG2-
      (gamma glutamic acid)2-Palmitoyl group (-PEG2-(gE)2-Palm)

<400> SEQUENCE: 54

Glu Leu Glu Gly Arg Glu Lys Val Arg Ala Ala Ile Xaa Xaa Glu Gly
1               5                   10                  15

Xaa Ser Thr Trp Ser Xaa Arg Lys Xaa
            20                  25

<210> SEQ ID NO 55
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
```

-continued

```
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -PEG2-
      (gamma glutamic acid)3-Palmitoyl group (-PEG2-(gE)3-Palm)

<400> SEQUENCE: 55

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 56
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
```

```
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)-Stearoyl group (-(PEG2)2-gE-Stea)

<400> SEQUENCE: 56

Leu Glu Gly Arg Glu Lys Val Arg Ala Gln Ile Xaa Xaa Glu Gly Xaa
1               5                   10                  15

Ser Thr Trp Ser Xaa Arg Lys Lys Xaa
            20                  25

<210> SEQ ID NO 57
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 14
<223> OTHER INFORMATION: Xaa in position 14 represents 2-amino-
      isobutyric acid (Aib)
<220> FEATURE:
<221> NAME/KEY: VARIANT
<222> LOCATION: 17
<223> OTHER INFORMATION: Xaa in position 17 represents 2-amino hexanoic
      acid (Norleucine - Nle)
<220> FEATURE:
<221> NAME/KEY: VARIANT
<222> LOCATION: 22
<223> OTHER INFORMATION: Xaa in position 22 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)2-Palmitoyl group (-(PEG2)2-(gE)2-
      Palm)

<400> SEQUENCE: 57

Glu Leu Glu Gly Arg Glu Lys Val Arg Ala Ala Ile Xaa Xaa Glu Gly
1               5                   10                  15

Xaa Ser Thr Trp Ser Xaa Arg Lys Xaa
            20                  25

<210> SEQ ID NO 58
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
```

```
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -
      (PEG2)2-(gamma glutamic acid)3-Palmitoyl group (-(PEG2)2-(gE)3-
      Palm)

<400> SEQUENCE: 58

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 59
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
```

```
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -
      (PEG2)2-(gamma glutamic acid)3-Palmitoyl group (-(PEG2)2-(gE)3-
      Palm)

<400> SEQUENCE: 59

Leu Glu Gly Arg Glu Lys Val Arg Ala Xaa Ile Xaa Xaa Glu Gly Xaa
1               5                   10                  15

Ser Thr Trp Ser Xaa Arg Lys Xaa
            20

<210> SEQ ID NO 60
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)3-Palmitoyl group (-(PEG2)2-(gE)3-
      Palm)
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 60

Leu Glu Gly Arg Glu Lys Val Arg Ala Xaa Ile Xaa Xaa Glu Gly Xaa
1               5                   10                  15

Ser Thr Trp Ser Xaa Arg Lys Lys Xaa
            20                  25

<210> SEQ ID NO 61
```

```
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino-4-
      acetamido-hexanoic acid (N-epsilon-Acetyl-lysine - K(Ac))
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)3-Palmitoyl group (-(PEG2)2-(gE)3-
      Palm)

<400> SEQUENCE: 61

Leu Glu Gly Arg Glu Lys Val Arg Ala Xaa Ile Xaa Xaa Glu Gly Xaa
1               5                   10                  15

Ser Thr Trp Ser Xaa Arg Lys Lys Xaa
            20                  25

<210> SEQ ID NO 62
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
```

```
<221> NAME/KEY: VARIANT
<222> LOCATION: 13
<223> OTHER INFORMATION: Xaa in position 13 represents 2-amino-
      isobutyric

```
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Palmitoyl group (-(PEG2)3-(gE)3-
      Palm)

<400> SEQUENCE: 63

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 64
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)3-Palmitoyl group (-(PEG2)4-(gE)3-
      Palm)
```

```
<400> SEQUENCE: 64

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 65
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)4-Palmitoyl group (-(PEG2)3-(gE)4-
      Palm)

<400> SEQUENCE: 65

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 66
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
```

```
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -PEG12-
      (gamma glutamic acid)3-Palmitoyl group (-PEG12-(gE)3-Palm)

<400> SEQUENCE: 66

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 67
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
```

```
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -
      (PEG2)2-(gamma glutamic acid)3-Stearoyl group (-(PEG2)2-(gE)3-
      Stea)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 67

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 68
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)3-Stearoyl group (-(PEG2)2-(gE)3-
      Stea)

<400> SEQUENCE: 68

Leu Glu Gly Arg Glu Lys Val Arg Ala Gln Ile Xaa Xaa Glu Gly Glu
1               5                   10                  15

Ser Thr Trp Ser Xaa Arg Lys Lys Xaa
            20                  25

<210> SEQ ID NO 69
<211> LENGTH: 25
```

```
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 9
<223> OTHER INFORMATION: Xaa in position 9 represents 2-amino-isobutyric
      acid (Aib)
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)3-Stearoyl group (-(PEG2)2-(gE)3-
      Stea)

<400> SEQUENCE: 69

Leu Glu Gly Arg Glu Lys Val Arg Xaa Gln Ile Xaa Xaa Glu Gly Xaa
1               5                   10                  15

Ser Thr Trp Ser Xaa Arg Lys Lys Xaa
            20                  25

<210> SEQ ID NO 70
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
```

```
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)3-Stearoyl group (-(PEG2)2-(gE)3-
      Stea)

<400> SEQUENCE: 70

Leu Glu Gly Arg Glu Lys Val Arg Ala Gln Ile Xaa Xaa Glu Gly Gln
1               5                   10                  15

Ser Thr Trp Ser Xaa Arg Lys Lys Xaa
            20                  25

<210> SEQ ID NO 71
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)3-Stearoyl group (-(PEG2)2-(gE)3-
      Stea)

<400> SEQUENCE: 71

Leu Glu Gly Arg Glu Lys Val Arg Ala Gln Ile Xaa Xaa Glu Gly Xaa
1               5                   10                  15

Ser Thr Trp Ser Xaa Arg Lys Lys Xaa
            20                  25

<210> SEQ ID NO 72
```

```
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 23
<223> OTHER INFORMATION: Xaa in position 23 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)3-Stearoyl group (-(PEG2)2-(gE)3-
      Stea)

<400> SEQUENCE: 72

Leu Glu Gly Arg Glu Lys Val Arg Ala Xaa Ile Xaa Xaa Glu Gly Xaa
1               5                   10                  15

Ser Thr Trp Ser Xaa Arg Xaa Lys Xaa
            20                  25

<210> SEQ ID NO 73
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
```

```
<221> NAME/KEY: VARIANT
<222> LOCATION: 12
<223> OTHER INFORMATION: Xaa in position 12 represents 2-amino-
      isob

```
<222> LOCATION: 24
<223> OTHER INFORMATION: Xaa in position 24 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 74

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 75
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 75

Leu Glu Gly Arg Glu Lys Val Arg Ala Gln Ile Xaa Xaa Glu Gly Xaa
1               5                   10                  15

Ser Thr Trp Ser Xaa Arg Lys Lys Xaa
            20                  25

<210> SEQ ID NO 76
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
```

```
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 76

Leu Glu Gly Arg Glu Lys Val Arg Ala Gln Ile Xaa Xaa Glu Gly Xaa
1               5                   10                  15

Ser Thr Trp Thr Xaa Arg Lys Lys Xaa
            20                  25

<210> SEQ ID NO 77
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
```

```
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 77

Leu Glu Gly Arg Glu Lys Val Arg Leu Gln Ile Xaa Xaa Glu Gly Xaa
1               5                   10                  15

Ser Thr Trp Thr Xaa Arg Lys Lys Xaa
            20                  25

<210> SEQ ID NO 78
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 78

Leu Glu Gly Arg Glu Lys Val Arg Ala Xaa Ile Xaa Xaa Glu Gly Xaa
1               5                   10                  15

Ser Thr Tyr Ser Xaa Arg Lys Xaa Xaa
            20                  25
```

```
<210> SEQ ID NO 79
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents 1-Naphtylalanine
      (1-Nal)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 79

Leu Glu Gly Arg Glu Lys Val Arg Ala Xaa Ile Xaa Xaa Glu Gly Xaa
1               5                   10                  15

Ser Thr Xaa Ser Xaa Arg Lys Xaa
            20

<210> SEQ ID NO 80
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 9
<223> OTHER INFORMATION: Xaa in position 9 represents 2-amino-isobutyric
      acid (Aib)
```

```
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents 1-Naphtylalanine
      (1-Nal)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 80

Leu Glu Gly Arg Glu Lys Val Arg Xaa Xaa Ile Xaa Xaa Glu Gly Xaa
1               5                   10                  15

Ser Thr Xaa Ser Xaa Arg Lys Xaa
            20

<210> SEQ ID NO 81
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
```

```
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 81

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 82
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
```

```
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)4-Stearoyl group (-(PEG2)3-(gE)4-
      Stea)

<400> SEQUENCE: 82

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 83
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 83

Leu Glu Gly Arg Glu Lys Val Arg Ala Xaa Ile Xaa Xaa Glu Gly Xaa
1               5                   10                  15

Ser Thr Trp Ser Xaa Arg Lys Xaa
            20

<210> SEQ ID NO 84
```

```
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents 1-Naphtylalanine
      (1-Nal)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to
      a -(PEG2)3-(gamma glutamic acid)3-Stearoyl group (-(PEG2)3-(gE)3-
      Stea)

<400> SEQUENCE: 84

Leu Glu Gly Arg Glu Lys Val Arg Ala Xaa Ile Xaa Xaa Glu Gly Xaa
1               5                   10                  15

Ser Thr Xaa Ser Xaa Arg Lys Xaa Xaa
            20                  25

<210> SEQ ID NO 85
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
```

```
<221> NAME/KEY: VARIANT
<222> LOCATION: 9
<223> OTHER INFORMATION: Xaa in position 9 represents 2-amino-isobutyric
      acid (Aib)
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents 1-Naphtylalanine
      (1-Nal)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 85

Leu Glu Gly Arg Glu Lys Val Arg Xaa Xaa Ile Xaa Xaa Glu Gly Xaa
1               5                  10                  15

Ser Thr Xaa Ser Xaa Arg Lys Xaa Xaa
            20                  25

<210> SEQ ID NO 86
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
```

-continued

```
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 86

Leu Glu Gly Arg Glu Lys Val Arg Ala Xaa Ile Xaa Xaa Glu Gly Xaa
1               5                   10                  15

Ser Thr Trp Ser Xaa Arg Lys Leu Xaa
            20                  25

<210> SEQ ID NO 87
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
       isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents 1-Naphtylalanine
      (1-Nal)
<220> FEATURE:
<221> NAME/KEY: VARIANT
<222> LOCATION: 21
```

<223> OTHER INFORMATION: Xaa in position 21 represents 2-amino-
isobutyric acid (Aib)
<220> FEATURE:
<221> NAME/KEY: VARIANT
<222> LOCATION: 23
<223> OTHER INFORMATION: Xaa in position 23 represents 2-amino-4-
acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
on its C-terminal extremity
<220> FEATURE:
<221> NAME/KEY: VARIANT
<222> LOCATION: 25
<223> OTHER INFORMATION: Xaa in position 25 represents a lysine amino
acid bound on the nitrogen atom of its lateral chain to a -
(PEG2)3-(gamma glutamic acid)3-Stearoyl group (-(PEG2)3-(gE)3-
Stea)

<400> SEQUENCE: 87

Leu Glu Gly Arg Glu Lys Val Arg Ala Xaa Ile Xaa Xaa Glu Gly Xaa
1               5                   10                  15

Ser Thr Xaa Ser Xaa Arg Xaa Leu Xaa
            20              25

<210> SEQ ID NO 88
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
group on its N-terminal extremity
<220> FEATURE:
<221> NAME/KEY: VARIANT
<222> LOCATION: 12
<223> OTHER INFORMATION: Xaa in position 12 represents 2-amino-
isobutyric acid (Aib)
<220> FEATURE:
<221> NAME/KEY: VARIANT
<222> LOCATION: 13
<223> OTHER INFORMATION: Xaa in position 13 represents 2-amino-
isobutyric acid (Aib)
<220> FEATURE:
<221> NAME/KEY: VARIANT
<222> LOCATION: 16
<223> OTHER INFORMATION: Xaa in position 16 represents 2-amino hexanoic
acid (Norleucine - Nle)
<220> FEATURE:
<221> NAME/KEY: VARIANT
<222> LOCATION: 21
<223> OTHER INFORMATION: Xaa in position 21 represents 2-amino-
isobutyric acid (Aib)
<220> FEATURE:
<221> NAME/KEY: VARIANT
<222> LOCATION: 25
<223> OTHER INFORMATION: The peptide is substituted with an -NH2 group
on its C-terminal extremity
<220> FEATURE:
<221> NAME/KEY: VARIANT
<222> LOCATION: 25
<223> OTHER INFORMATION: Xaa in position 25 represents a lysine amino
acid bound on the nitrogen atom of its lateral chain to a -
(PEG2)3-(gamma glutamic acid)4-Stearoyl group (-(PEG2)3-(gE)4-
Stea)

<400> SEQUENCE: 88

Leu Glu Gly Arg Glu Lys Val Arg Ala Gln Ile Xaa Xaa Glu Gly Xaa
1               5                   10                  15

Ser Thr Trp Ser Xaa Arg Lys Lys Xaa

```
                   20                  25

<210> SEQ ID NO 89
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)4-Stearoyl group (-(PEG2)3-(gE)4-
      Stea)

<400> SEQUENCE: 89

Leu Glu Gly Arg Glu Lys Val Arg Ala Xaa Ile Xaa Xaa Glu Gly Xaa
1               5                   10                  15

Ser Thr Trp Ser Xaa Arg Lys Lys Xaa
            20                  25

<210> SEQ ID NO 90
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
```

```
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)3-Stearoyl group (-(PEG2)4-(gE)3-
      Stea)

<400> SEQUENCE: 90

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 91
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
```

```
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)3-Stearoyl group (-(PEG2)4-(gE)3-
      Stea)

<400> SEQUENCE: 91

Leu Glu Gly Arg Glu Lys Val Arg Ala Xaa Ile Xaa Xaa Glu Gly Xaa
1               5                   10                  15

Ser Thr Trp Ser Xaa Arg Lys Lys Xaa
            20                  25

<210> SEQ ID NO 92
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)3-Stearoyl group (-(PEG2)4-(gE)3-
      Stea)

<400> SEQUENCE: 92

Leu Glu Gly Arg Glu Lys Val Arg Ala Gln Ile Xaa Xaa Glu Gly Xaa
1               5                   10                  15

Ser Thr Trp Ser Xaa Arg Lys Lys Xaa
            20                  25

<210> SEQ ID NO 93
<211> LENGTH: 25
```

```
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)5-(gamma glutamic acid)3-Stearoyl group (-(PEG2)5-(gE)3-
      Stea)

<400> SEQUENCE: 93

Leu Glu Gly Arg Glu Lys Val Arg Ala Gln Ile Xaa Xaa Gly Gly Xaa
1               5                   10                  15

Ser Thr Trp Ser Xaa Arg Lys Lys Xaa
            20                  25

<210> SEQ ID NO 94
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
```

```
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2DGA)-(gamma glutamic acid)3-Stearoyl group (-(PEG2DGA)-(gE)3-
      Stea)

<400> SEQUENCE: 94

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 95
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
```

```
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2DGA)2-(gamma glutamic acid)3-Stearoyl group (-(PEG2DGA)2-
      (gE)3-Stea)

<400> SEQUENCE: 95

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 96
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2DGA)3-(gamma glutamic acid)3-Stearoyl group (-(PEG2DGA)3-
      (gE)3-Stea)

<400> SEQUENCE: 96

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
```

<210> SEQ ID NO 97
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac) group on its N-terminal extremity
<220> FEATURE:
<221> NAME/KEY: VARIANT
<222> LOCATION: 12
<223> OTHER INFORMATION: Xaa in position 12 represents 2-amino-isobutyric acid (Aib)
<220> FEATURE:
<221> NAME/KEY: VARIANT
<222> LOCATION: 13
<223> OTHER INFORMATION: Xaa in position 13 represents 2-amino-isobutyric acid (Aib)
<220> FEATURE:
<221> NAME/KEY: VARIANT
<222> LOCATION: 16
<223> OTHER INFORMATION: Xaa in position 16 represents 2-amino hexanoic acid (Norleucine - Nle)
<220> FEATURE:
<221> NAME/KEY: VARIANT
<222> LOCATION: 21
<223> OTHER INFORMATION: Xaa in position 21 represents 2-amino-isobutyric acid (Aib)
<220> FEATURE:
<221> NAME/KEY: VARIANT
<222> LOCATION: 25
<223> OTHER INFORMATION: The peptide is substituted with an -NH2 group on its C-terminal extremity
<220> FEATURE:
<221> NAME/KEY: VARIANT
<222> LOCATION: 25
<223> OTHER INFORMATION: Xaa in position 25 represents a lysine amino acid bound on the nitrogen atom of its lateral chain to a -PEG12-(gamma glutamic acid)3-Stearoyl group (-(PEG12)-(gE)3-Stea)

<400> SEQUENCE: 97

```
Leu Glu Gly Arg Glu Lys Val Arg Ala Gln Ile Xaa Xaa Glu Gly Xaa
1               5                   10                  15

Ser Thr Trp Ser Xaa Arg Lys Lys Xaa
            20                  25
```

<210> SEQ ID NO 98
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac) group on its N-terminal extremity
<220> FEATURE:
<221> NAME/KEY: VARIANT
<222> LOCATION: 12
<223> OTHER INFORMATION: Xaa in position 12 represents 2-amino-isobutyric acid (Aib)
<220> FEATURE:
<221> NAME/KEY: VARIANT
<222> LOCATION: 13
<223> OTHER INFORMATION: Xaa in position 13 represents 2-amino-isobutyric acid (Aib)
<220> FEATURE:
<221> NAME/KEY: VARIANT
<222> LOCATION: 16

```
<223> OTHER INFORMATION: Xaa in position 16 represents 2-amino hexanoic
      acid (Norleucine - Nle)
<220> FEATURE:
<221

```
                    20                  25

<210> SEQ ID NO 100
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -
      (PEG2)2-(gamma glutamic acid)2-PEG2-(gamma glutamic acid)-Stearoyl
      group (-(PEG2)2-(gE)2-PEG2-(gE)-Stea)

<400> SEQUENCE: 100

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 101
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
```

```
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)2-PEG2-(gamma glutamic acid)-
      Stearoyl (-(PEG2)2-(gE)2-PEG2-(gE)-Stea)

<400> SEQUENCE: 101

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 102
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
```

```
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)3-PEG2-(gamma glutamic acid)-Stearoyl
      group (-(PEG2)2-(gE)3-PEG2-(gE)-Stea)

<400> SEQUENCE: 102

Leu Glu Gly Arg Glu Lys Val Arg Ala Xaa Ile Xaa Xaa Glu Gly Xaa
1               5                   10                  15

Ser Thr Trp Ser Xaa Arg Lys Lys Xaa
            20                  25

<210> SEQ ID NO 103
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents 1-Naphtylalanine
      (1-Nal)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)3-PEG2-(gamma glutamic acid)-Stearoyl
      group (-(PEG2)2-(gE)3-PEG2-(gE)-Stea)

<400> SEQUENCE: 103

Leu Glu Gly Arg Glu Lys Val Arg Ala Xaa Ile Xaa Xaa Glu Gly Xaa
1               5                   10                  15

Ser Thr Xaa Ser Xaa Arg Lys Lys Xaa
```

```
                    20                  25

<210> SEQ ID NO 104
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: The peptide is substituted with an -NH2 group
      on its C-terminal extremity
<220> FEATURE:
<221> NAME/KEY: VARIANT
<222> LOCATION: 24
<223> OTHER INFORMATION: Xaa in position 24 represents a lysine amino
      acid bound on the nitrogen atom of its lateral chain to a -(gamma
      glutamic acid)2-(PEG2)2-(gamma glutamic acid)-Stearoyl group
      (-(gE)2-(PEG2)2-(gE)-Stea)

<400> SEQUENCE: 104

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 105
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
```

```
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)2-(PEG2)2-(gamma glutamic acid)-Stearoyl group
      (-(gE)2-(PEG2)2-(gE)-Stea)

<400> SEQUENCE: 105

Leu Glu Gly Arg Glu Lys Val Arg Ala Gln Ile Xaa Xaa Glu Gly Xaa
1               5                   10                  15

Ser Thr Trp Ser Xaa Arg Lys Lys Xaa
            20                  25

<210> SEQ ID NO 106
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)2-(PEG2)3-(gamma glutamic acid)-Stearoyl group
      (-(gE)2-(PEG2)3-(gE)-Stea)

<400> SEQUENCE: 106

Leu Glu Gly Arg Glu Lys Val Arg Ala Gln Ile Xaa Xaa Glu Gly Xaa
1               5                   10                  15
```

Ser Thr Trp Ser Xaa Arg Lys Lys Xaa
            20              25

<210> SEQ ID NO 107
<211> LENGTH: 27
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25, 26
<223> OTHER INFORMATION: Linked by -PEG2-PEG2-PEG2-
<220> FEATURE:
<221> NAME/KEY: VARIANT
<222> LOCATION: 26
<223> OTHER INFORMATION: Xaa in position 26 represents -(gamma glutamic
      acid)3- (-(gE)3-)
<220> FEATURE:
<221> NAME/KEY: VARIANT
<222> LOCATION: 27
<223> OTHER INFORMATION: The peptide is substituted with an -NH2 group
      on its C-terminal extremity
<220> FEATURE:
<221> NAME/KEY: VARIANT
<222> LOCATION: 27
<223> OTHER INFORMATION: Xaa in position 27 represents a lysine amino
      acid bound on the nitrogen atom of its lateral chain to a -gamma
      glutamic acid-palmitoyl group (-gE-Palm)

<400> SEQUENCE: 107

Leu Glu Gly Arg Glu Lys Val Arg Ala Gln Ile Xaa Xaa Glu Gly Xaa
1               5                   10                  15

Ser Thr Trp Ser Xaa Arg Lys Lys Lys Xaa Xaa
            20              25

<210> SEQ ID NO 108
<211> LENGTH: 27
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12

```
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25, 26
<223> OTHER INFORMATION: Linked by -PEG2-PEG2-PEG2-PEG2-
<220> FEATURE:
<221> NAME/KEY: VARIANT
<222> LOCATION: 26
<223> OTHER INFORMATION: Xaa in position 26 represents -(gamma glutamic
      acid)3- (-(gE)3-)
<220> FEATURE:
<221> NAME/KEY: VARIANT
<222> LOCATION: 27
<223> OTHER INFORMATION: The peptide is substituted with an -NH2 group
      on its C-terminal extremity
<220> FEATURE:
<221> NAME/KEY: VARIANT
<222> LOCATION: 27
<223> OTHER INFORMATION: Xaa in position 27 represents a lysine amino
      acid bound on the nitrogen atom of its lateral chain to a -gamma
      glutamic acid-palmitoyl group (-gE-Palm)

<400> SEQUENCE: 108

Leu Glu Gly Arg Glu Lys Val Arg Ala Gln Ile Xaa Xaa Glu Gly Xaa
1               5                   10                  15

Ser Thr Trp Ser Xaa Arg Lys Lys Lys Xaa Xaa
            20                  25

<210> SEQ ID NO 109
<211> LENGTH: 27
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
```

```
<221> NAME/KEY: VARIANT
<222> LOCATION: 25, 26
<223> OTHER INFORMATION: Linked by -PEG2-PEG2-PEG2-
<220> FEATURE:
<221> NAME/KEY: VARIANT
<222> LOCATION: 26
<223> OTHER INFORMATION: Xaa in position 26 represents -(gamma glutamic
      acid)2- (-(gE)2-)
<220> FEATURE:
<221> NAME/KEY: VARIANT
<222> LOCATION: 27
<223> OTHER INFORMATION: 27 peptide is substituted with an -NH2 group on
      its C-terminal extremity
<220> FEATURE:
<221> NAME/KEY: VARIANT
<222> LOCATION: 27
<223> OTHER INFORMATION: Xaa in position 27 represents a lysine amino
      acid bound on the nitrogen atom of its lateral chain to a -gamma
      glutamic acid-palmitoyl group (-gE-Palm)

<400> SEQUENCE: 109

Leu Glu Gly Arg Glu Lys Val Arg Ala Gln Ile Xaa Xaa Glu Gly Xaa
1               5                   10                  15

Ser Thr Trp Ser Xaa Arg Lys Lys Lys Xaa Xaa
            20                  25

<210> SEQ ID NO 110
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24, 25
<223> OTHER INFORMATION: Linked by-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)3- (-(gE)3-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
``` glutamic acid-palmitoyl group (-gE-Palm)

<400> SEQUENCE: 110

Leu Glu Gly Arg Glu Lys Val Arg Ala Gln Ile Xaa Xaa Glu Gly Xaa
1               5                   10                  15

Ser Thr Trp Ser Xaa Arg Lys Lys Xaa Xaa
            20                  25

<210> SEQ ID NO 111
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)5-Stearoyl group (-(PEG2)3-(gE)5-
      Stea)

<400> SEQUENCE: 111

Leu Glu Gly Arg Glu Lys Val Arg Ala Xaa Ile Xaa Xaa Glu Gly Gln
1               5                   10                  15

Ser Thr Trp Ser Xaa Arg Lys Lys Xaa
            20                  25

<210> SEQ ID NO 112
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-

```
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 112

Leu Glu Gly Arg Glu Lys Val Arg Ala Xaa Ile Xaa Xaa Glu Gly Xaa
1               5                   10                  15

Ser Thr Phe Ser Xaa Arg Lys Xaa Xaa
            20                  25

<210> SEQ ID NO 113
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
```

```
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 113

Leu Glu Gly Arg Glu Lys Val Arg Ala Xaa Ile Xaa Xaa Glu Gly Gln
1               5                   10                  15

Ser Thr Trp Ser Xaa Arg Lys Xaa Xaa
            20                  25

<210> SEQ ID NO 114
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
```

```
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl group (-(gE)3-Palm)

<400> SEQUENCE: 114

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 115
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)4-Stearoyl group (-(PEG2)3-(gE)4-
      Stea)

<400> SEQUENCE: 115

Leu Glu Gly Arg Glu Lys Val Arg Ala Xaa Ile Xaa Xaa Glu Gly Gln
1               5                   10                  15

Ser Thr Trp Ser Xaa Arg Lys Lys Xaa
            20                  25

<210> SEQ ID NO 116
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
```

```
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)2- (-(gE)2-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
      glutamic acid-palmitoyl group (-gE-Palm)

<400> SEQUENCE: 116

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa Xaa
            20                  25

<210> SEQ ID NO 117
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
```

```
           isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)2- (-(gE)2-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
      glutamic acid-palmitoyl group (-gE-Palm)

<400> SEQUENCE: 117

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa Xaa
            20                  25

<210> SEQ ID NO 118
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
```

```
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-
<220> FEATURE:
<221> NAME/KEY: VARIANT
<222> LOCATION: 25
<223> OTHER INFORMATION: Xaa in position 25 represents -(gamma glutamic
      acid)2- (-(gE)2-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
      glutamic acid-palmitoyl group (-gE-Palm)

<400> SEQUENCE: 118

Leu Glu Gly Arg Glu Lys Val Arg Ala Gln Ile Xaa Xaa Glu Gly Xaa
1               5                   10                  15

Ser Thr Trp Ser Xaa Arg Lys Xaa Xaa Xaa
            20                  25

<210> SEQ ID NO 119
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-
<220> FEATURE:
```

```
<221> NAME/KEY: VARIANT
<222> LOCATION: 25
<223> OTHER INFORMATION: Xaa in position 25 represents -(gamma glutamic
      acid)2- (-(gE)2-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
      glutamic acid-palmitoyl group (-gE-Palm)

<400> SEQUENCE: 119

Leu Glu Gly Arg Glu Lys Val Arg Ala Gln Ile Xaa Xaa Glu Gly Xaa
1               5                   10                  15

Ser Thr Trp Ser Xaa Arg Lys Xaa Xaa Xaa
            20                  25

<210> SEQ ID NO 120
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Lauroyl group (-(PEG2)3-(gE)3-Lau)

<400> SEQUENCE: 120
```

-continued

```
Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
                20              25

<210> SEQ ID NO 121
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)2- (-(gE)2-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
      glutamic acid-palmitoyl group (-gE-Palm)

<400> SEQUENCE: 121

Leu Glu Gly Arg Glu Lys Val Arg Ala Gln Ile Xaa Xaa Glu Gly Xaa
1               5                   10                  15

Ser Thr Trp Ser Xaa Arg Lys Xaa Xaa Xaa
                20              25

<210> SEQ ID NO 122
<211> LENGTH: 26
<212> TYPE: PRT
<213> ORGANISM: Artificial Sequence
<220> FEATURE:
```

-continued

```
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25, 26
<223> OTHER INFORMATION: Linked by -PEG4-PEG4-
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -(gamma
      glutamic acid)5-stearoyl group (-(gE)5-Stea)

<400> SEQUENCE: 122

Leu Glu Gly Arg Glu Lys Val Arg Ala Gln Ile Xaa Xaa Gly Gly Xaa
1               5                   10                  15

Ser Thr Trp Ser Xaa Arg Lys Lys Lys Xaa
            20                  25

<210> SEQ ID NO 123
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
```

```
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG4-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 123

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 124
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
```

```
<220> FEATURE:
<221> NAME/KEY: VARIANT
<222> LOCATION: 24, 25
<223> OTHER INFORMATION: Linked by -PEG4-PEG4-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-stearoyl group (-(gE)3-Stea)

<400> SEQUENCE: 124

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 125
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents alpha-Methyl-
      tryptophane (Mtr)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-
<220> FEATURE:
<221> NAME/KEY: VARIANT
<222> LOCATION: 25
<223> OTHER INFORMATION: The peptide is substituted with an -NH2 group
```

```
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-plamitoyl group (-(gE)4-Palm)

<400> SEQUENCE: 125

Leu Glu Gly Arg Glu Lys Val Arg Ala Xaa Ile Xaa Xaa Glu Gly Xaa
1               5                   10                  15

Ser Thr Xaa Ser Xaa Arg Lys Xaa Xaa
            20                  25

<210> SEQ ID NO 126
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 22
<223> OTHER INFORMATION: Xaa in position 22 represents Citruline (Cit)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 126

Leu Glu Gly Arg Glu Lys Val Arg Ala Xaa Ile Xaa Xaa Glu Gly Xaa
1               5                   10                  15
```

```
                           Ser Thr Trp Ser Xaa Xaa Ala Xaa Xaa
                                       20              25

<210> SEQ ID NO 127
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 127

Leu Glu Gly Arg Glu Lys Val Arg Ala Xaa Ile Xaa Xaa Glu Gly Xaa
1               5                   10                  15

Ser Thr Trp Ser Xaa Arg Lys Leu Xaa
                20              25

<210> SEQ ID NO 128
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
```

```
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)4-Stearoyl group (-(PEG2)3-(gE)4-
      Stea)

<400> SEQUENCE: 128

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 129
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
```

```
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 22
<223> OTHER INFORMATION: Xaa in position 22 represents Citruline (Cit)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 129

Leu Glu Gly Arg Glu Lys Val Arg Ala Xaa Ile Xaa Xaa Glu Gly Xaa
1               5                   10                  15

Ser Thr Trp Ser Xaa Xaa Lys Xaa Xaa
            20                  25

<210> SEQ ID NO 130
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
```

```
<223> OTHER INFORMATION: The peptide is substituted with an -NH2 group
     on its C-terminal extremity
<220> FEATURE:
<221> NAME/KEY: VARIANT
<222> LOCATION: 25
<223> OTHER INFORMATION: Xaa in position 25 represents a lysine amino
     acid bound on the nitrogen atom of its lateral chain to a -
     (PEG2)4-(gamma glutamic acid)4-Palmitoyl group (-(PEG2)4-(gE)4-
     Palm)

<400> SEQUENCE: 130

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 131
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
     group on its N-terminal extremity
<220> FEATURE:
<221> NAME/KEY: VARIANT
<222> LOCATION: 10
<223> OTHER INFORMATION: Xaa in position 10 represents 2-amino-4-
     acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
     isobutyric acid (Aib)
<220> FEATURE:
<221> NAME/KEY: VARIANT
<222> LOCATION: 13
<223> OTHER INFORMATION: Xaa in position 13 represents 2-amino-
     isobutyric acid (Aib)
<220> FEATURE:
<221> NAME/KEY: VARIANT
<222> LOCATION: 16
<223> OTHER INFORMATION: Xaa in position 16 represents 2-amino hexanoic
     acid (Norleucine - Nle)
<220> FEATURE:
<221> NAME/KEY: VARIANT
<222> LOCATION: 21
<223> OTHER INFORMATION: Xaa in position 21 represents alpha-Methyl-
     lysine (Mly)
<220> FEATURE:
<221> NAME/KEY: VARIANT
<222> LOCATION: 24
<223> OTHER INFORMATION: Xaa in position 24 represents 2-amino-4-
     acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked bys -PEG2-PEG2-PEG2-PEG2-
<220> FEATURE:
<221> NAME/KEY: VARIANT
<222> LOCATION: 25
<223> OTHER INFORMATION: The peptide is substituted with an -NH2 group
     on its C-terminal extremity
<220> FEATURE:
<221> NAME/KEY: VARIANT
<222> LOCATION: 25
<223> OTHER INFORMATION: Xaa in position 25 represents a lysine amino
     acid bound on the nitrogen atom of its lateral chain to a -(gamma
     glutamic acid)4-plamitoyl group (-(gE)4-Palm)

<400> SEQUENCE: 131

Leu Glu Gly Arg Glu Lys Val Arg Ala Xaa Ile Xaa Xaa Glu Gly Xaa
```

Ser Thr Trp Ser Xaa Arg Lys Xaa Xaa
            20              25

<210> SEQ ID NO 132
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
       acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 22
<223> OTHER INFORMATION: Xaa in position 22 represents Citruline (Cit)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)3-Stearoyl group (-(PEG2)4-(gE)3-
      Stea)

<400> SEQUENCE: 132

Leu Glu Gly Arg Glu Lys Val Arg Ala Xaa Ile Xaa Xaa Glu Gly Xaa
1               5                   10                  15

Ser Thr Trp Ser Xaa Xaa Ala Xaa Xaa
            20              25

<210> SEQ ID NO 133
<211> LENGTH: 25
<212> TYPE: PRT
<213> ORGANISM: Artificial Sequence
<220> FEATURE:
<223> OTHER INFORMATION: Peptide analogue of the B-chain of Relaxin-2

```
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 22
<223> OTHER INFORMATION: Xaa in position 22 represents N-omega-methyl-
      arginine (Rme)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 133

Leu Glu Gly Arg Glu Lys Val Arg Ala Xaa Ile Xaa Xaa Glu Gly Xaa
1               5                   10                  15

Ser Thr Trp Ser Xaa Xaa Lys Xaa Xaa
            20                  25

<210> SEQ ID NO 134
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
```

```
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 23
<223> OTHER INFORMATION: Xaa in position 23 represents N-epsilon,N-
      epsilon, N-epsilon-trimethyl-lysine (Tml)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 134

Leu Glu Gly Arg Glu Lys Val Arg Ala Xaa Ile Xaa Xaa Gly Gly Xaa
1               5                   10                  15

Ser Thr Trp Ser Xaa Arg Xaa Xaa Xaa
            20                  25

<210> SEQ ID NO 135
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
```

```
-continued

<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)3-Stearoyl group (-(PEG2)4-(gE)3-
      Stea)

<400> SEQUENCE: 135

Leu Glu Gly Arg Glu Lys Val Arg Ala Xaa Ile Xaa Xaa Glu Gly Xaa
1               5                   10                  15

Ser Thr Trp Ser Xaa Arg Ala Xaa Xaa
            20                  25

<210> SEQ ID NO 136
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
```

```
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)3- (-(gE)3-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
      glutamic acid-palmitoyl group (-gE-Palm)

<400> SEQUENCE: 136

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa Xaa
            20                  25

<210> SEQ ID NO 137
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 22
<223> OTHER INFORMATION: Xaa in position 22 represents N-omega-methyl-
      arginine (Rme)
<220> FEATURE:
<221> NAME/KEY: VARIANT
<222> LOCATION: 23
<223> OTHER INFORMATION: Xaa in position 23 represents N-epsilon,N-
      epsilon, N-epsilon-trimethyl-lysine (Tml)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
```

```
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 137

Leu Glu Gly Arg Glu Lys Val Arg Ala Xaa Ile Xaa Xaa Glu Gly Xaa
1               5                   10                  15

Ser Thr Trp Ser Xaa Xaa Xaa Xaa Xaa
            20                  25

<210> SEQ ID NO 138
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 22
<223> OTHER INFORMATION: Xaa in position 22 represents N-omega-methyl-
      arginine (Rme)
<220> FEATURE:
<221> NAME/KEY: VARIANT
<222> LOCATION: 23
<223> OTHER INFORMATION: Xaa in position 23 represents N-epsilon,N-
      epsilon, N-epsilon-trimethyl-lysine (Tml)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
```

```
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl (-(PEG2)3-(gE)3-Stea)

<400> SEQUENCE: 138

Leu Glu Gly Arg Glu Lys Val Arg Ala Xaa Ile Xaa Xaa Glu Gly Xaa
1               5                   10                  15

Ser Thr Trp Ser Xaa Xaa Xaa Xaa Xaa
            20                  25

<210> SEQ ID NO 139
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)3- (-(gE)3-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
      glutamic acid-palmitoyl group (-gE-Palm)

<400> SEQUENCE: 139

Leu Glu Gly Arg Glu Lys Val Arg Ala Xaa Ile Xaa Xaa Glu Gly Xaa
```

```
1               5                   10                  15
Ser Thr Phe Ser Xaa Ala Ala Xaa Xaa Xaa
            20                  25

<210> SEQ ID NO 140
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)4-Palmitoyl group (-(PEG2)4-(gE)4-
      Palm)
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 140

Leu Glu Gly Arg Glu Lys Val Arg Ala Xaa Ile Xaa Xaa Glu Gly Xaa
1               5                   10                  15

Ser Thr Phe Ser Xaa Arg Lys Xaa Xaa
            20                  25

<210> SEQ ID NO 141
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
```

```
             group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 22
<223> OTHER INFORMATION: Xaa in position 22 represents N-omega-methyl-
      arginine (Rme)
<220> FEATURE:
<221> NAME/KEY: VARIANT
<222> LOCATION: 23
<223> OTHER INFORMATION: Xaa in position 23 represents N-epsilon,N-
      epsilon, N-epsilon-trimethyl-lysine (Tml)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)4-Palmitoyl group (-(PEG2)4-(gE)4-
      Palm)

<400> SEQUENCE: 141

Leu Glu Gly Arg Glu Lys Val Arg Ala Xaa Ile Xaa Xaa Glu Gly Xaa
1               5                   10                  15

Ser Thr Trp Ser Xaa Xaa Xaa Xaa Xaa
            20                  25

<210> SEQ ID NO 142
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
```

```
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents -TTDS-TTDS-
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -(gamma
      glutamic acid)4-plamitoyl group (-(gE)4-Palm)

<400> SEQUENCE: 142

Leu Glu Gly Arg Glu Lys Val Arg Ala Xaa Ile Xaa Xaa Glu Gly Xaa
1               5                   10                  15

Ser Thr Phe Ser Xaa Arg Lys Xaa Xaa Xaa
            20                  25

<210> SEQ ID NO 143
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
```

```
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by-PEG2-PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-plamitoyl group (-(gE)4-Palm)

<400> SEQUENCE: 143

Leu Glu Gly Arg Glu Lys Val Arg Ala Xaa Ile Xaa Xaa Glu Gly Xaa
1               5                   10                  15

Ser Thr Phe Ser Xaa Arg Lys Xaa Xaa
            20                  25

<210> SEQ ID NO 144
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
```

```
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl group (-(gE)3-Palm)

<400> SEQUENCE: 144

Leu Glu Gly Arg Glu Lys Val Arg Ala Xaa Ile Xaa Xaa Glu Gly Xaa
1               5                   10                  15

Ser Thr Phe Ser Xaa Arg Lys Xaa Xaa
            20                  25

<210> SEQ ID NO 145
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 26 represents -(gamma glutamic
      acid)3- (-(gE)3-)
<220> FEATURE:
<221> NAME/KEY: VARIANT
<222> LOCATION: 26
<223> OTHER INFORMATION: The peptide is substituted with an -NH2 group
      on its C-terminal extremity
```

```
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
      glutamic acid-palmitoyl group (-gE-Palm)

<400> SEQUENCE: 145

Leu Glu Gly Arg Glu Lys Val Arg Ala Xaa Ile Xaa Xaa Glu Gly Xaa
1               5                   10                  15

Ser Thr Phe Ser Xaa Arg Lys Xaa Xaa Xaa
            20                  25

<210> SEQ ID NO 146
<211> LENGTH: 27
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents -TTDS-TTDS-
<220> FEATURE:
<221> NAME/KEY: VARIANT
<222> LOCATION: 26
<223> OTHER INFORMATION: Xaa in position 26 represents -(gamma glutamic
      acid)3- (-(gE)3-)
<220> FEATURE:
<221> NAME/KEY: VARIANT
<222> LOCATION: 27
<223> OTHER INFORMATION: The peptide is substituted with an -NH2 group
      on its C-terminal extremity
<220> FEATURE:
<221> NAME/KEY: VARIANT
<222> LOCATION: 27
<223> OTHER INFORMATION: Xaa in position 27 represents a lysine amino
      acid bound on the nitrogen atom of its lateral chain to a -gamma
      glutamic acid-palmitoyl group (-gE-Palm)

<400> SEQUENCE: 146
```

```
Leu Gly Arg Glu Lys Val Arg Ala Xaa Ile Xaa Xaa Glu Gly Xaa
1               5                   10                  15

Ser Thr Phe Ser Xaa Arg Lys Xaa Xaa Xaa
            20                  25
```

<210> SEQ ID NO 147
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac) group on its N-terminal extremity
<220> FEATURE:
<221> NAME/KEY: VARIANT
<222> LOCATION: 10
<223> OTHER INFORMATION: Xaa in position 10 represents 2-amino-4-acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-isobutyric acid (Aib)
<220> FEATURE:
<221> NAME/KEY: VARIANT
<222> LOCATION: 13
<223> OTHER INFORMATION: Xaa in position 13 represents 2-amino-isobutyric acid (Aib)
<220> FEATURE:
<221> NAME/KEY: VARIANT
<222> LOCATION: 16
<223> OTHER INFORMATION: Xaa in position 16 represents 2-amino hexanoic acid (Norleucine - Nle)
<220> FEATURE:
<221> NAME/KEY: VARIANT
<222> LOCATION: 21
<223> OTHER INFORMATION: Xaa in position 21 represents 2-amino-isobutyric acid (Aib)
<220> FEATURE:
<221> NAME/KEY: VARIANT
<222> LOCATION: 24
<223> OTHER INFORMATION: Xaa in position 24 represents 2-amino-4-acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents a lysine amino acid bound on the nitrogen atom of its lateral chain to a -(PEG2)4-(gamma glutamic acid)4-Palmitoyl group (-(PEG2)4-(gE)4-Palm)
<220> FEATURE:
<221> NAME/KEY: VARIANT
<222> LOCATION: 25
<223> OTHER INFORMATION: The peptide is substituted with an -NH2 group on its C-terminal extremity

<400> SEQUENCE: 147

```
Leu Glu Gly Arg Glu Lys Val Arg Ala Xaa Ile Xaa Xaa Glu Gly Xaa
1               5                   10                  15

Ser Thr Phe Ser Xaa Arg Lys Xaa Xaa
            20                  25
```

<210> SEQ ID NO 148
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT

```
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 22
<223> OTHER INFORMATION: Xaa in position 22 represents N-omega,
      N-omega'-dimethyl-arginine (symmetrical) (Rds)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Palmitoyl group (-(PEG2)3-(gE)3-
      Palm)
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 148

Leu Glu Gly Arg Glu Lys Val Arg Ala Xaa Ile Xaa Xaa Glu Gly Xaa
1               5                   10                  15

Ser Thr Trp Ser Xaa Xaa Lys Xaa Xaa
            20                  25

<210> SEQ ID NO 149
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
```

```
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)3- (-(gE)3-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
      glutamic acid-palmitoyl group (-gE-Palm)

<400> SEQUENCE: 149

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa Xaa
            20                  25

<210> SEQ ID NO 150
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
```

```
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-plamitoyl group (-(gE)4-Palm)

<400> SEQUENCE: 150

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa
            20                  25

<210> SEQ ID NO 151
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 22
<223> OTHER INFORMATION: Xaa in position 22 represents N-omega-methyl-
``` arginine (Rme)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)3- (-(gE)3-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -gamma
      glutamic acid-palmitoyl group (-gE-Palm)

<400> SEQUENCE: 151

Leu Glu Gly Arg Glu Lys Val Arg Ala Xaa Ile Xaa Xaa Glu Gly Xaa
1               5                   10                  15

Ser Thr Phe Ser Xaa Xaa Ala Xaa Xaa Xaa
            20                  25

<210> SEQ ID NO 152
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl
      (Ac) group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents alpha-Methyl-
      phenylalanine (Mph)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT

```
<222> LOCATION: 24
<223> OTHER INFORMATION: Xaa in position 24 represents 2-amino-4-
      acetamido-hexanoic acid (N-ep

```
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)3-Palmitoyl group (-(PEG2)4-(gE)3-
      Palm)

<400> SEQUENCE: 153

Leu Glu Gly Arg Glu Lys Val Arg Ala Xaa Ile Xaa Xaa Glu Gly Xaa
1               5                   10                  15

Ser Thr Phe Ser Xaa Arg Lys Xaa Xaa
            20                  25

<210> SEQ ID NO 154
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)4-Palmitoyl group (-(PEG2)4-(gE)4-
      Palm)

<400> SEQUENCE: 154

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa
            20                  25
```

```
<210> SEQ ID NO 155
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 155

Leu Glu Gly Arg Glu Lys Val Arg Ala Xaa Ile Xaa Xaa Glu Gly Xaa
1               5                   10                  15

Ser Thr Trp Ser Xaa Ala Ala Xaa Xaa
            20                  25

<210> SEQ ID NO 156
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
```

```
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a-
      (PEG2DGA)2-(gamma glutamic acid)3-Stearoyl group (-(PEG2DGA)2-
      (gE)3-Stea)

<400> SEQUENCE: 156

Leu Glu Gly Arg Glu Lys Val Arg Ala Xaa Ile Xaa Xaa Glu Gly Xaa
1               5                   10                  15

Ser Thr Trp Ser Xaa Ala Ala Xaa Xaa
            20                  25

<210> SEQ ID NO 157
<211> LENGTH: 27
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
```

```
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents -TTDS-TTDS-
<220> FEATURE:
<221> NAME/KEY: VARIANT
<222> LOCATION: 26
<223> OTHER INFORMATION: Xaa in position 26 represents -(gamma glutamic
      acid)3- (-(gE)3-)
<220> FEATURE:
<221> NAME/KEY: VARIANT
<222> LOCATION: 27
<223> OTHER INFORMATION: The peptide is substituted with an -NH2 group
      on its C-terminal extremity
<220> FEATURE:
<221> NAME/KEY: VARIANT
<222> LOCATION: 27
<223> OTHER INFORMATION: Xaa in position 27 represents a lysine amino
      acid bound on the nitrogen atom of its lateral chain to a -gamma
      glutamic acid-palmitoyl group (-gE-Palm)

<400> SEQUENCE: 157

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa Xaa Xaa
                20                  25

<210> SEQ ID NO 158
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 19
<223> OTHER INFORMATION: Xaa in position 19 represents 5-Hydroxy-
      tryptophane (Wox)
<220> FEATURE:
<221> NAME/KEY: VARIANT
<222> LOCATION: 21
```

```
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 158

Leu Glu Gly Arg Glu Lys Val Arg Ala Xaa Ile Xaa Xaa Glu Gly Xaa
1               5                   10                  15

Ser Thr Xaa Ser Xaa Arg Lys Xaa Xaa
            20                  25

<210> SEQ ID NO 159
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)2- (-(gE)2-)
```

```
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -(gamma
      glutamic acid)2-palmitoyl group (-(gE)2-Palm)

<400> SEQUENCE: 159

Leu Glu Gly Arg Glu Lys Val Arg Ala Xaa Ile Xaa Xaa Glu Gly Xaa
1               5                   10                  15

Ser Thr Phe Ser Xaa Arg Lys Xaa Xaa Xaa
            20                  25

<210> SEQ ID NO 160
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)2- (-(gE)2-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
```

```
<223> OTHER INFORMATION: Xaa in position 26 represents a lysine amino
      acid bound on the nitrogen atom of its lateral chain to a -(gamma
      glutamic acid)2-palmitoyl group (-(gE)2-Palm)

<400> SEQUENCE: 160

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa Xaa
            20                  25

<210> SEQ ID NO 161
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-Lauroyl group (-(gE)4-Lau)

<400> SEQUENCE: 161

Leu Glu Gly Arg Glu Lys Val Arg Ala Xaa Ile Xaa Xaa Glu Gly Gln
1               5                   10                  15

Ser Thr Phe Ser Xaa Arg Ala Xaa Xaa
            20                  25

<210> SEQ ID NO 162
<211> LENGTH: 26
<212> TYPE: PRT
<213> ORGANISM: Artificial Sequence
<220> FEATURE:
```

```
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents -TTDS-TTDS-
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -(gamma
      glutamic acid)4-plamitoyl group (-(gE)4-Palm)

<400> SEQUENCE: 162

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa Xaa
            20                  25

<210> SEQ ID NO 163
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
```

```
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Pentadecanoyl group (-(PEG2)3-
      (gE)3-Penta)

<400> SEQUENCE: 163

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 164
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
```

```
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Heptadecanoyl group (-(PEG2)3-
      (gE)3-Hepta)
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 164

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 165
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)2-(gamma glutamic acid)2-PEG2-(gamma glutamic acid)-
      Palmitoyl group (-(PEG2)2-(gE)2-PEG2-(gE)-Palm)
<220> FEATURE:
<221> NAME/KEY: VARIANT
```

```
<222> LOCATION: 25
<223> OTHER INFORMATION: The peptide is substituted with an -NH2 group
      on its C-terminal extremity

<400> SEQUENCE: 165

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 166
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (TTDS)2-(gamma glutamic acid)3-Palmitoyl group (-(TTDS)2-(gE)3-
      Palm)

<400> SEQUENCE: 166

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 167
<211> LENGTH: 25
<212> TYPE: PRT
```

```
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-Pentadecanoyl group (-(gE)4-Penta)

<400> SEQUENCE: 167

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa
            20                  25

<210> SEQ ID NO 168
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
```

```
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by-PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)2- (-(gE)2-)
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -(gamma
      glutamic acid)2-Pentadecanoyl group (-(gE)2-Penta)
<220> FEATURE:
<221> NAME/KEY: VARIANT
<222> LOCATION: 26
<223> OTHER INFORMATION: The peptide is substituted with an -NH2 group
      on its C-terminal extremity

<400> SEQUENCE: 168

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa Xaa
            20                  25

<210> SEQ ID NO 169
<211> LENGTH: 27
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
```

```
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents -TTDS-TTDS-TTDS-
<220> FEATURE:
<221> NAME/KEY: VARIANT
<222> LOCATION: 26
<223> OTHER INFORMATION: Xaa in position 26 represents -(gamma glutamic
      acid)2- (-(gE)2-)
<220> FEATURE:
<221> NAME/KEY: VARIANT
<222> LOCATION: 27
<223> OTHER INFORMATION: The peptide is substituted with an -NH2 group
      on its C-terminal extremity
<220> FEATURE:
<221> NAME/KEY: VARIANT
<222> LOCATION: 27
<223> OTHER INFORMATION: Xaa in position 27 represents a lysine amino
      acid bound on the nitrogen atom of its lateral chain to a -(gamma
      glutamic acid)2-palmitoyl group (-(gE)2-Palm)

<400> SEQUENCE: 169

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa Xaa Xaa
            20                  25

<210> SEQ ID NO 170
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
```

<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-plamitoyl group (-(gE)4-Palm)

<400> SEQUENCE: 170

Leu Glu Gly Arg Glu Lys Val Arg Ala Xaa Ile Xaa Xaa Glu Gly Gln
1               5                   10                  15

Ser Thr Phe Ser Xaa Arg Ala Xaa Xaa
            20                  25

<210> SEQ ID NO 171
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino
      hexanoic acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Eicosanoyl group ((-PEG2)3-(gE)3-
      Eico)
<220> FEATURE:
<221> NAME/KEY: VARIANT

```
<222> LOCATION: 25
<223> OTHER INFORMATION: The peptide is substituted with an -NH2 group
      on its C-terminal extremity

<400> SEQUENCE: 171

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 172
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-Myristoyl group (-(gE)4-Myr)
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 172

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa
            20                  25
```

```
<210> SEQ ID NO 173
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3- docosanoyl group ((-PEG2)3-(gE)3-
      Doco)
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 173

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 174
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
```

```
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)3-(gamma glutamic acid)3-Stearoyl group (-(PEG2)3-(gE)3-
      Stea)

<400> SEQUENCE: 174

Leu Glu Gly Arg Glu Lys Val Arg Ala Gln Ile Xaa Xaa Glu Gly Xaa
1               5                   10                  15

Ser Thr Trp Ser Xaa Arg Lys Lys Xaa
            20                  25

<210> SEQ ID NO 175
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
```

```
<221> NAME/KEY: VARIANT
<222> LOCATION: 24, 25
<223> OTHER INFORMATION: Linked by -PEG2DGA-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl group (-(gE)3-Palm)

<400> SEQUENCE: 175

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 176
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2DGA-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl group (-(gE)3-Palm)

<400> SEQUENCE: 176

Leu Glu Gly Arg Glu Lys Val Arg Ala Xaa Ile Xaa Xaa Glu Gly Gln
```

```
1               5                   10                  15
Ser Thr Trp Ser Xaa Arg Lys Xaa Xaa
            20                  25

<210> SEQ ID NO 177
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2DGA-PEG2DGA-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl group (-(gE)3-Palm)

<400> SEQUENCE: 177

Leu Glu Gly Arg Glu Lys Val Arg Ala Gln Ile Xaa Xaa Glu Gly Gln
1               5                   10                  15

Ser Thr Trp Ser Xaa Arg Lys Xaa Xaa
            20                  25

<210> SEQ ID NO 178
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
```

<220> FEATURE:
<221> NAME/KEY: VARIANT
<222> LOCATION: 12
<223> OTHER INFORMATION: Xaa in position 12 repres

```
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl group (-(gE)3-Palm)

<400> SEQUENCE: 179

Leu Glu Gly Arg Glu Lys Val Arg Ala Xaa Ile Xaa Xaa Glu Gly Gln
1               5                   10                  15

Ser Thr Tyr Ser Xaa Arg Lys Xaa Xaa
            20                  25

<210> SEQ ID NO 180
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)4-Stearoyl group (-(PEG2)4-(gE)4-
      Stea)

<400> SEQUENCE: 180
```

Leu Glu Gly Arg Glu Lys Val Arg Ala Xaa Ile Xaa Xaa Glu Gly Gln
1               5                   10                  15

Ser Thr Trp Ser Xaa Arg Lys Xaa Xaa
                20                  25

<210> SEQ ID NO 181
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents 2-amino-
      isobutyric acid (Aib)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG8-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl group (-(gE)3-Palm)

<400> SEQUENCE: 181

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
                20                  25

<210> SEQ ID NO 182
<211> LENGTH: 25
<212> TYPE: PRT
<213> ORGANISM: Artificial Sequence
<220> FEATURE:
<223> OTHER INFORMATION: Peptide analogue of the B-chain of Relaxin-2

```
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)4-Pentadecanoyl group (-(gE)4-Penta)

<400> SEQUENCE: 182

Leu Glu Gly Arg Glu Lys Val Arg Ala Xaa Ile Xaa Xaa Glu Gly Gln
1               5                   10                  15

Ser Thr Phe Ser Xaa Arg Ala Xaa Xaa
            20                  25

<210> SEQ ID NO 183
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
```

```
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (TTDS)3-(gamma glutamic acid)3-Palmitoyl group (-(TTDS)3-(gE)3-
      Palm)

<400> SEQUENCE: 183

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa
            20                  25

<210> SEQ ID NO 184
<211> LENGTH: 27
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents -TTDS-TTDS-TTDS-
```

```
<220> FEATURE:
<221> NAME/KEY: VARIANT
<222> LOCATION: 26
<223> OTHER INFORMATION: Xaa in position 26 represents -(gamma glutamic
      acid)2- (-(gE)2-)
<220> FEATURE:
<221> NAME/KEY: VARIANT
<222> LOCATION: 27
<223> OTHER INFORMATION: The peptide is substituted with an -NH2 group
      on its C-terminal extremity
<220> FEATURE:
<221> NAME/KEY: VARIANT
<222> LOCATION: 27
<223> OTHER INFORMATION: Xaa in position 27 represents a lysine amino
      acid bound on the nitrogen atom of its lateral chain to a -(gamma
      glutamic acid)2-Pentadecanoyl group (-(gE)2-Penta)

<400> SEQUENCE: 184

Leu Glu Gly Arg Glu Lys Val Arg Ala Xaa Ile Xaa Xaa Glu Gly Gln
1               5                   10                  15

Ser Thr Phe Ser Xaa Arg Ala Xaa Xaa Xaa Xaa
            20                  25

<210> SEQ ID NO 185
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
      acid)2- (-(gE)2-)
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
```

```
<223>  OTHER INFORMATION: Xaa in position 26 represents a lysine amino
       acid bound on the nitrogen atom of its lateral chain to a -(gamma
       glutamic acid)2-palmitoyl group (-(gE)2-Palm)

<400> SEQUENCE: 185

Leu Glu Gly Arg Glu Lys Val Arg Ala Xaa Ile Xaa Xaa Glu Gly Gln
1               5                   10                  15

Ser Thr Phe Ser Xaa Arg Ala Xaa Xaa Xaa
            20                  25

<210> SEQ ID NO 186
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
       group on its N-terminal extremity
<220> FEATURE:
<221> NAME/KEY: VARIANT
<222> LOCATION: 10
<223> OTHER INFORMATION: Xaa in position 10 represents 2-amino-4-
       acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
       isobutyric acid (Aib)
<220> FEATURE:
<221> NAME/KEY: VARIANT
<222> LOCATION: 13
<223> OTHER INFORMATION: Xaa in position 13 represents 2-amino-
       isobutyric acid (Aib)
<220> FEATURE:
<221> NAME/KEY: VARIANT
<222> LOCATION: 21
<223> OTHER INFORMATION: Xaa in position 21 represents alpha-Methyl-
       lysine (Mly)
<220> FEATURE:
<221> NAME/KEY: VARIANT
<222> LOCATION: 24
<223> OTHER INFORMATION: Xaa in position 24 represents 2-amino-4-
       acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: Xaa in position 25 represents -(gamma glutamic
       acid)2- (-(gE)2-)
<220> FEATURE:
<221> NAME/KEY: VARIANT
<222> LOCATION: 26
<223> OTHER INFORMATION: The peptide is substituted with an -NH2 group
       on its C-terminal extremity
<220> FEATURE:
<221> NAME/KEY: VARIANT
<222> LOCATION: 26
<223> OTHER INFORMATION: Xaa in position 26 represents a lysine amino
       acid bound on the nitrogen atom of its lateral chain to a -(gamma
       glutamic acid)2-Pentadecanoyl group (-(gE)2-Penta)

<400> SEQUENCE: 186

Leu Glu Gly Arg Glu Lys Val Arg Ala Xaa Ile Xaa Xaa Glu Gly Gln
1               5                   10                  15

Ser Thr Phe Ser Xaa Arg Ala Xaa Xaa Xaa
            20                  25
```

```
<210> SEQ ID NO 187
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents -TTDS-TTDS-TTDS-
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a ), -
      (gamma glutamic acid)3-palmitoyl group (-(gE)3-Palm)

<400> SEQUENCE: 187

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa Xaa
            20                  25

<210> SEQ ID NO 188
<211> LENGTH: 26
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
```

```
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents -TTDS-TTDS-TTDS-
<220> FEATURE:
<221> NAME/KEY: VARIANT
<222> LOCATION: 26
<223> OTHER INFORMATION: The peptide is substituted with an -NH2 group
      on its C-terminal extremity
<220> FEATURE:
<221> NAME/KEY: VARIANT
<222> LOCATION: 26
<223> OTHER INFORMATION: Xaa in position 26 represents a lysine amino
      acid bound on the nitrogen atom of its lateral chain to a -(gamma
      glutamic acid)3-Pentadecanoyl group (-(gE)3-Penta)

<400> SEQUENCE: 188

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa Xaa
            20                  25

<210> SEQ ID NO 189
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
```

```
<220> FEATURE:
<221> NAME/KEY: VARIANT
<222> LOCATION: 21
<223> OTHER INFORMATION: Xaa in position 21 represents alpha-Meth

```
<221> NAME/KEY: VARIANT
<222> LOCATION: 25
<223> OTHER INFORMATION: The peptide is substituted with an -NH2 group
      on its C-terminal extremity

<400> SEQUENCE: 190

Leu Glu Gly Arg Glu Lys Val Arg Ala Xaa Ile Xaa Xaa Glu Gly Gln
1               5                   10                  15

Ser Thr Phe Ser Xaa Arg Ala Xaa Xaa
            20                  25

<210> SEQ ID NO 191
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric  acid (Aib)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -
      (PEG2)4-(gamma glutamic acid)4-Palmitoyl group (-(PEG2)4-(gE)4-
      Palm)

<400> SEQUENCE: 191

Leu Glu Gly Arg Glu Lys Val Arg Ala Xaa Ile Xaa Xaa Glu Gly Gln
1               5                   10                  15

Ser Thr Phe Ser Xaa Arg Ala Xaa Xaa
            20                  25

<210> SEQ ID NO 192
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
```

```
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
      isobutyric acid (Aib)
<220> FEATURE:
<221> NAME/KEY: VARIANT
<222> LOCATION: 13
<223> OTHER INFORMATION: Xaa in position 13 represents 2-amino-
      isobutyric acid (Aib)
<220> FEATURE:
<221> NAME/KEY: VARIANT
<222> LOCATION: 16
<223> OTHER INFORMATION: Xaa in position 16 represents 2-amino hexanoic
      acid (Norleucine - Nle)
<220> FEATURE:
<221> NAME/KEY: VARIANT
<222> LOCATION: 21
<223> OTHER INFORMATION: Xaa in position 21 represents alpha-Methyl-
      lysine (Mly)
<220> FEATURE:
<221> NAME/KEY: VARIANT
<222> LOCATION: 24
<223> OTHER INFORMATION: Xaa in position 24 represents 2-amino-4-
      acetamido-hexanoic acid (N-epsilon-Acetyl-lysine - K(Ac))
<220> FEATURE:
<221> NAME/KEY: VARIANT
<222> LOCATION: 24, 25
<223> OTHER INFORMATION: Linked by -PEG2-PEG2-PEG2-PEG2-
<220> FEATURE:
<221> NAME/KEY: VARIANT
<222> LOCATION: 25
<223> OTHER INFORMATION: The peptide is substituted with an -NH2 group
      on its C-terminal extremity
<220> FEATURE:
<221> NAME/KEY: VARIANT
<222> LOCATION: 25
<223> OTHER INFORMATION: Xaa in position 25 represents a lysine amino
      acid bound on the nitrogen atom of its lateral chain to a -(gamma
      glutamic acid)3-palmitoyl group (-(gE)3-Palm)

<400> SEQUENCE: 192

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa
            20                  25

<210> SEQ ID NO 193
<211> LENGTH: 27
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Xaa in position 10 represents 2-amino-4-
      acetamido-hexanoic acid (N-epsilon-Acetyl-lysine - K(Ac))
<220> FEATURE:
<221> NAME/KEY: VARIANT
<222> LOCATION: 12
<223> OTHER INFORMATION: Xaa in position 12 represents 2-amino-
``` isobutyric acid (Aib)
<220> FEATURE:
<221> NAME/KEY: VARIANT
<222> LOCATION: 13
<223> OTHER INFORMATION: Xaa in position 13 represents 2-amino-
    isobutyric acid (Aib)
<220> FEATURE:
<221> NAME/KEY: VARIANT
<222> LOCATION: 16
<223> OTHER INFORMATION: Xaa in position 16 represents 2-amino hexanoic
    acid (Norleucine - Nle)
<220> FEATURE:
<221> NAME/KEY: VARIANT
<222> LOCATION: 21
<223> OTHER INFORMATION: Xaa in position 21 represents alpha-Methyl-
    lysine (Mly)
<220> FEATURE:
<221> NAME/KEY: VARIANT
<222> LOCATION: 24
<223> OTHER INFORMATION: Xaa in position 24 represents 2-amino-4-
    acetamido-hexanoic acid (N-epsilon-Acetyl-lysine - K(Ac))
<220> FEATURE:
<221> NAME/KEY: VARIANT
<222> LOCATION: 25
<223> OTHER INFORMATION: Xaa in position 25 represents -TTDS-TTDS-TTDS-
<220> FEATURE:
<221> NAME/KEY: VARIANT
<222> LOCATION: 26
<223> OTHER INFORMATION: Xaa in position 26 represents -(gamma glutamic
    acid)3- (-(gE)3-)
<220> FEATURE:
<221> NAME/KEY: VARIANT
<222> LOCATION: 27
<223> OTHER INFORMATION: The peptide is substituted with an -NH2 group
    on its C-terminal extremity
<220> FEATURE:
<221> NAME/KEY: VARIANT
<222> LOCATION: 27
<223> OTHER INFORMATION: Xaa in position 27 represents a lysine amino
    acid bound on the nitrogen atom of its lateral chain to a -gamma
    glutamic acid-palmitoyl group (-gE-Palm)

<400> SEQUENCE: 193

Leu Glu Gly Arg Glu Lys Val Arg Ala Xaa Ile Xaa Xaa Glu Gly Xaa
1               5                   10                  15

Ser Thr Phe Ser Xaa Arg Ala Xaa Xaa Xaa Xaa
            20                  25

<210> SEQ ID NO 194
<211> LENGTH: 24
<212> TYPE: PRT
<213> ORGANISM: Artificial Sequence
<220> FEATURE:
<223> OTHER INFORMATION: H2-relaxin chain A
<220> FEATURE:
<221> NAME/KEY: VARIANT
<222> LOCATION: 1
<223> OTHER INFORMATION: The peptide is substituted with a hydrogen atom
    (H) on its N-terminal extremity

<400> SEQUENCE: 194

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 195
<211> LENGTH: 29
<212> TYPE: PRT
<213> ORGANISM: Artificial Sequence
<220> FEATURE:
<223> OTHER INFORMATION: H2-relaxin chain B
<220> FEATURE:

```
<221> NAME/KEY: VARIANT
<222> LOCATION: 1
<223> OTHER INFORMATION: The peptide is substituted with a hydrogen atom
      (H) on its N-terminal extremity

<400> SEQUENCE: 195

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 196
<211> LENGTH: 27
<212> TYPE: PRT
<213> ORGANISM: Artificial Sequence
<220> FEATURE:
<223> OTHER INFORMATION: Peptide analogue of the B-chain of Relaxin 2 -
      comparison example
<220> FEATURE:
<221> NAME/KEY: VARIANT
<222> LOCATION: 1
<223> OTHER INFORMATION: The peptide is substituted with a hydrogen atom
      (H) on its N-terminal extremity
<220> FEATURE:
<221> NAME/KEY: VARIANT
<222> LOCATION: 27
<223> OTHER INFORMATION: The peptide is substituted with an -NH2 group
      on its C-terminal extremity

<400> SEQUENCE: 196

Val Ile Lys Leu Ser Gly Arg Glu Leu Val Arg Ala Gln Ile Ala Ile
1               5                   10                  15

Ser Gly Met Ser Thr Trp Ser Lys Arg Ser Leu
            20                  25

<210> SEQ ID NO 197
<211> LENGTH: 27
<212> TYPE: PRT
<213> ORGANISM: Artificial Sequence
<220> FEATURE:
<223> OTHER INFORMATION: Peptide analogue of the B-chain of Relaxin 2 -
      comparison example
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 27
<223> OTHER INFORMATION: The peptide is substituted with an -NH2 group
      on its C-terminal extremity

<400> SEQUENCE: 197

Val Ile Lys Leu Ser Gly Arg Glu Leu Val Arg Ala Gln Ile Ala Ile
1               5                   10                  15

Ser Gly Met Ser Thr Trp Ser Lys Arg Ser Leu
            20                  25

<210> SEQ ID NO 198
<211> LENGTH: 27
<212> TYPE: PRT
<213> ORGANISM: Artificial Sequence
<220> FEATURE:
<223> OTHER INFORMATION: Peptide analogue of the B-chain of Relaxin 2 -
      comparison example
<220> FEATURE:
<221> NAME/KEY: VARIANT
<222> LOCATION: 1
<223> OTHER INFORMATION: The peptide is substituted with an acetyl (Ac)
``` group on its N-terminal extremity
<220> FEATURE:
<221> NAME/KEY: VARIANT
<222> LOCATION: 27
<223> OTHER INFORMATION: The peptide is substituted with an -NH2 group
      on its C-terminal extremity

<400> SEQUENCE: 198

Val Ile Lys Leu Ser Gly Arg Glu Leu Val Arg Ala Gln Ile Ala Ile
1               5                  10                  15

Ser Gly Met Ser Thr Trp Ser Lys Lys Lys Lys
            20                  25

<210> SEQ ID NO 199
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Peptide is substituted with an acetyl group on
      its N-terminal extremity and may be absent
<220> FEATURE:
<221> NAME/KEY: VARIANT
<222> LOCATION: 2
<223> OTHER INFORMATION: Xaa represents an amino acid selected from the
      group consisting of leucine (Leu), 2-amino-isobutyric acid (Aib),
      N-epsilon-acetyl-lysine (K(Ac)) and alpha-methyl-leucine (Mel)
<220> FEATURE:
<221> NAME/KEY: VARIANT
<222> LOCATION: 7
<223> OTHER INFORMATION: Xaa represents an amino acid selected from the
      group consisting of lysine (Lys), homolysine (Hly), arginine
      (Arg), homoarginine (Har) and ornithine (Orn)
<220> FEATURE:
<221> NAME/KEY: VARIANT
<222> LOCATION: 10
<223> OTHER INFORMATION: Xaa represents an amino acid selected from the
      group consisting of alanine (Ala), 2-amino-isobutyric acid (Aib),
      leucine (Leu), N-epsilon-acetyl-lysine (K(Ac)) and glutamine (Gln)
<220> FEATURE:
<221> NAME/KEY: VARIANT
<222> LOCATION: 11
<223> OTHER INFORMATION: Xaa = represents an amino acid selected from
      the group consisting of glutamine (Gln), N-epsilon-acetyl-lysine
      (K(Ac)), citruline (Cit), alanine (Ala) and 2-amino-isobutyric
      acid (Aib)
<220> FEATURE:
<221> NAME/KEY: VARIANT
<222> LOCATION: 13
<223> OTHER INFORMATION: Xaa represents an amino acid selected from the
      group consisting of alanine (Ala) and 2-amino-isobutyric acid
      (Aib)
<220> FEATURE:
<221> NAME/KEY: VARIANT
<222> LOCATION: 14
<223> OTHER INFORMATION: Xaa represents an amino acid selected from the
      group consisting of isoleucine (Ile) and 2-amino-isobutyric acid
      (Aib)
<220> FEATURE:
<221> NAME/KEY: VARIANT
<222> LOCATION: 17
<223> OTHER INFORMATION: Xaa represents an amino acid selected from the
      group consisting of methionine (Met), norleucine (Nle), leucine
      (Leu), alanine (Ala), glutamine (Gln), N-epsilon-acetyl-lysine
      (K(Ac)) and glutamic acid (Glu)
<220> FEATURE:
<221> NAME/KEY: VARIANT
<222> LOCATION: 19
<223> OTHER INFORMATION: Xaa represents an amino acid selected from the
      group consisting of threonine (Thr), lysine (Lys), arginine (Arg)
      and glutamine (Gln)
<220> FEATURE:
<221> NAME/KEY: VARIANT
<222> LOCATION: 20

```
<223> OTHER INFORMATION: Xaa represents an amino acid selected from the
      group consisting of tryptophan, 5-fluoro-tryptophan, 5-chloro-
      tryptophan, 5-methoxy-tryptophan, tyrosine, phenylalanine, 4-
      fluoro-phenylalanine,
<220> FEATURE:
<221> NAME/KEY: VARIANT
<222> LOCATION: 20
<223> OTHER INFORMATION: ...1-naphtylalanine, 2-naphtylalanine, alpha-
      methyl-tryptophane, alpha-methyl-phenylalanine and 5-hydroxy-
      tryptophane (Wox).
<220> FEATURE:
<221> NAME/KEY: VARIANT
<222> LOCATION: 21
<223> OTHER INFORMATION: Xaa represents an amino acid selected from the
      group consisting of serine (Ser), threonine (Thr), alpha-methyl-
      serine (Mse), N-epsilon-acetyl-lysine (K(Ac)) and valine (Val)
<220> FEATURE:
<221> NAME/KEY: VARIANT
<222> LOCATION: 22
<223> OTHER INFORMATION: Xaa represents an amino acid selected from the
      group consisting of lysine (Lys), 2-amino-isobutyric acid (Aib),
      alpha-methyl-lysine (Mly), arginine (Arg) and alpha-methyl-
      arginine (Mar)
<220> FEATURE:
<221> NAME/KEY: VARIANT
<222> LOCATION: 23
<223> OTHER INFORMATION: Xaa represents an amino acid selected from the
      group consisting of arginine (Arg), N-omega-methyl-arginine (Rme),
      alanine (Ala), N-omega,N-omega-dimethyl-arginine (Rds,
      symmetrical dimethyl arginine) and citruline (Cit)
<220> FEATURE:
<221> NAME/KEY: VARIANT
<222> LOCATION: 23
<223> OTHER INFORMATION: Modified by the moiety
      (X32).sub.b-(X33).sub.c-(K).sub.d-(X35).sub.e-(gE).sub.f-X.sub.37-
      C.sub.ter as described in Formula I of the specification.

<400> SEQUENCE: 199

Glu Xaa Glu Gly Arg Glu Xaa Val Arg Xaa Xaa Ile Xaa Xaa Glu Gly
1               5                   10                  15

Xaa Ser Xaa Xaa Xaa Xaa Xaa
            20

<210> SEQ ID NO 200
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Peptide is substituted with an acetyl group on
      its N-terminal extremity and may be absent
<220> FEATURE:
<221> NAME/KEY: VARIANT
<222> LOCATION: 10
<223> OTHER INFORMATION: Xaa represents an amino acid selected from the
      group consisting of alanine, 2-amino-isobutyric acid and leucine
<220> FEATURE:
<221> NAME/KEY: VARIANT
<222> LOCATION: 11
<223> OTHER INFORMATION: Xaa represents an amino acid selected from the
      group consisting of glutamine, N-epsilon-acetyl-lysine and alanine
<220> FEATURE:
<221> NAME/KEY: VARIANT
<222> LOCATION: 13, 14
<223> OTHER INFORMATION: Xaa = 2-amino-isobutyric acid
<220> FEATURE:
<221> NAME/KEY: VARIANT
<222> LOCATION: 17
<223> OTHER INFORMATION: Xaa = represents an amino acid selected from
      the group consisting of methionine, norleucine, glutamine,
      N-epsilon-acetyl-lysine and glutamic acid
<220> FEATURE:
<221> NAME/KEY: VARIANT
```

```
<222> LOCATION: 20
<223> OTHER INFORMATION: Xaa = represents an amino acid selected from
      the group consisting of tryptophan, 1-naphtylalanine,
      phenylalanine, tyrosine,
<220> FEATURE:
<221> NAME/KEY: VARIANT
<222> LOCATION: 20
<223> OTHER INFORMATION: ...alpha-methyl-tryptophane, alpha-methyl-
      phenylalanine and 5-hydroxy-tryptophane
<220> FEATURE:
<221> NAME/KEY: VARIANT
<222> LOCATION: 21
<223> OTHER INFORMATION: Xaa represents an amino acid selected from the
      group consisting of serine, threonine and alpha-methyl-serine
<220> FEATURE:
<221> NAME/KEY: VARIANT
<222> LOCATION: 22
<223> OTHER INFORMATION: Xaa represents an amino acid selected from the
      group consisting of lysine, 2-amino-isobutyric acid and alpha-
      methyl-lysine
<220> FEATURE:
<221> NAME/KEY: VARIANT
<222> LOCATION: 23
<223> OTHER INFORMATION: Xaa represents an amino acid selected from the
      group consisting of arginine, N-omega-methyl-arginine, alanine,
      N-omega,N-omega-dimethyl-arginine and citruline
<220> FEATURE:
<221> NAME/KEY: VARIANT
<222> LOCATION: 23
<223> OTHER INFORMATION: Modified by the moiety
      (X32).sub.b-(X33).sub.c-(K).sub.d-(X35).sub.e-(gE).sub.f-X.sub.37-
      C.sub.ter as described in Formula Ia of the specification.

<400> SEQUENCE: 200

Glu Leu Glu Gly Arg Glu Lys Val Arg Xaa Xaa Ile Xaa Xaa Glu Gly
1               5                   10                  15

Xaa Ser Thr Xaa Xaa Xaa Xaa
            20

<210> SEQ ID NO 201
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3, 4, 6, 7
<223> OTHER INFORMATION: Xaa = Any Amino Acid
<220> FEATURE:
<221> NAME/KEY: VARIANT
<222> LOCATION: 8
<223> OTHER INFORMATION: Xaa = Ile or Val

<400> SEQUENCE: 201

Arg Xaa Xaa Xaa Arg Xaa Xaa Xaa
1               5
```

UNITED STATES PATENT AND TRADEMARK OFFICE
CERTIFICATE OF CORRECTION

PATENT NO. : 10,988,523 B2
APPLICATION NO. : 16/264547
DATED : April 27, 2021
INVENTOR(S) : Brasseur et al.

It is certified that error appears in the above-identified patent and that said Letters Patent is hereby corrected as shown below:

In the Claims

Column 383, Claim 1, Line 57, delete "X30-R-" and insert -- X30- X31- --, therefor.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*